US005874276A

United States Patent [19]
Fowler et al.

[11] Patent Number: 5,874,276
[45] Date of Patent: Feb. 23, 1999

[54] CELLULASE ENZYMES AND SYSTEMS FOR THEIR EXPRESSIONS

[75] Inventors: Timothy Fowler, Belmont; Kathleen A. Clarkson; Michael Ward, both of San Francisco; Katherine D. Collier, Redwood City; Edmund Larenas, San Carlos, all of Calif.

[73] Assignee: Genencor International, Inc., Rochester, N.Y.

[21] Appl. No.: 448,873

[22] Filed: May 24, 1995

Related U.S. Application Data

[62] Division of Ser. No. 169,948, Dec. 17, 1993.

[51] Int. Cl.$^6$ .................................................. C12N 9/42
[52] U.S. Cl. ................................................ 435/209
[58] Field of Search ............................................ 435/209

[56] References Cited

U.S. PATENT DOCUMENTS

| | | | |
|---|---|---|---|
| 4,762,788 | 8/1988 | Warzywoda et al. | 435/209 |
| 5,137,819 | 8/1992 | Kilburn et al. | 435/179 |
| 5,202,247 | 4/1993 | Kilburn et al. | 435/195 |
| 5,223,409 | 6/1993 | Ladner et al. | 435/69.7 |
| 5,298,405 | 3/1994 | Nevalainen et al. | 435/209 |

FOREIGN PATENT DOCUMENTS

| | | |
|---|---|---|
| 0 137 280 | 4/1985 | European Pat. Off. |
| 0 549 062 | 6/1993 | European Pat. Off. |
| 85/04672 | 10/1985 | WIPO |
| WO 90/09436 | 8/1990 | WIPO |
| WO 91/04673 | 4/1991 | WIPO |
| WO 91/10732 | 7/1991 | WIPO |
| 91/17244 | 11/1991 | WIPO |
| WO 91/18090 | 11/1991 | WIPO |
| WO 92/06184 | 4/1992 | WIPO |
| WO 92/06209 | 4/1992 | WIPO |
| 93/05226 | 3/1993 | WIPO |
| 93/21331 | 10/1993 | WIPO |
| WO 93/20714 | 10/1993 | WIPO |
| 94/07983 | 4/1994 | WIPO |

OTHER PUBLICATIONS

*Aho, et al, Monoclonal antibodies against core and cellulose–binding domains of *Trichoderma reesei* cellobiohydrolases I and II and endoglucananse I Eur. J. Biochem 200:643–649 (1991).

*Aho, et al. "The conserved terminal region of *Trichoderma reesei* cellulases forms a strong, antigenic epitope for polyclonal antibodies" Biochimica Biophysica Acta 1087(2):137–141 (1990).

*Aho, et al. "Structural and functional analysis of *Trichoderma reesei* endoglucanase I expressed in yeast *Saccaromyces cerevisiae*" FEBS Letters 291(1):45–49 (1991).

*Claeyssens et al. "Structure–function relationships of cellulolytic proteins from *Trichoderma reesei*" *Trichoderma Reesei* Cellulases, eds. Kubicek et al. pp. 1–11 (1989).

*Claeyssens et al. "Structure–Activity Relationships in Cellulolytic Enzymes" Enzyme Syst. Lignocellul. Degrad. Ed. Michael P. Coughlan, pp. 37–49 (1989).

*Din et al., "Non–Hydrolytic Distruption of Cellulose–Fibres By the Binding Domain of a Bacterial Cellulase" Bio/Technology 9:1096–1099 (Nov. 1991).

*Durand et al. "Classical and Molecular Genetics Applied to *Trichoderma reesei* for the Selection of Improved Cellulotytic Industrial Strains" Biochemistry and Genetics of Cellulose Degradation, Academic Press Limited pp. 135–151 (1988).

*Francisco et al. "Specific Adhesion and Hydrolosis of Cellulose by Intact *Escherichia coli* Expressing Surface Anchored Cellulase or Cellulose Binding Domains" Bio/Technology 11:491–495 (Apr. 1993).

*Gilkes et al., "Domains in Microbial β–1,4–Glycanases:Sequence Conservation, Function and Enzyme Families" Microbiological Reviews 55(2):303–315 (Jun. 1991).

*Gilkes et al. "The Adsorption of a Bacterial Cellulase and Its Two Isolated Domains to Crystalline Cellulose" J. Biological Chem. 267(10):6743–6749 (Apr. 1992).

*Greenwood et al., "Cellulose–binding domains: potential for purification of complex proteins" Protein Engineering 5(4):361–365 (1992).

*Hakansson et al., "Purification and Characterization of a Low Molecular Weight 1,4–β–Glucan Glucanohydrolase from the Cellulolytic Fungus *Trichoderma Viride* OM 9414" Biochimica et Biophysica Acta 524:385–392 (1978).

*Hann et al., "The Signal Recognition Particle in *S. Cerevisiae*" Cell 67:131–144 (Oct. 1991).

*Klyosov, "Cellulases of the Third Generation" Biochemistry and Genetics of Cellulose Degradation Eds. J.P. Aubert, Academic Press Limited, FEMS Symposium No. 43, pp. 87–99 (1988).

*Landry et al. "Recognition of nascent polypeptides for targeting and folding" TIBS 16:159–163 (Apr. 1991).

*Offord et al., "Preparative Purification of *Trichoderma reesei* Native and Core Cellobiohydrolase I by Electrophoresis and Chromatofocusing" Applied Biochem. And Biotech. 28/29:377–386 (1991).

*Okada, "Comparisons of Primary, Secondary and Tertiary Structures of Xylanase of *Bacillus pumilus* and Cellulase of *Aspergillus acleatus*", Micro. Util, Renewable Resource (1991).

*Nakari et al., "Structure and Expression of the TEF1α Gene of Trichoderma" Abstract, 1st European Conf. of Fungal Genetics, University of Nottingham, Nottingham, England (Aug. 1992).

(List continued on next page.)

*Primary Examiner*—Charles L. Patterson, Jr.
*Attorney, Agent, or Firm*—Genencor International, Inc.

[57] ABSTRACT

The present invention relates to the cloning and high level expression of novel truncated cellulase proteins or derivatives thereof in the filamentous fungus *Trichoderma longibrachiatum*. Further aspects of the present invention relate to fungal transformants that express the novel truncated cellulases and derivatives, and expression vectors comprising the DNA gene fragments or variants thereof that code for the truncated cellulases derived from *Trichoderma longibrachiatum* using genetic engineering techniques.

3 Claims, 22 Drawing Sheets

OTHER PUBLICATIONS

*Nakari, et al., "New Trichoderma Promoters for Production of Hydrolytic Enzymes on Glucose Medium" Foundation for Biotech. and Industr. Fermentaion Res. 8:239–246 (1993).

*Ong et al., "The cellulose–binding domains of cellulases: tools for biotechnology" Trends Biotechnol 7(9):239–243 (1989).

*Saarilahti, et al., "CelS: a novel endoglucasese identified from *Erwinia carotovara* subsp. *Carotovara*" Gene 90:9–14 (1990).

*Saloheimo, et al., "Small endoglucasase from *Trichoderma reese*, cloned by expression in yeast" *Trichoderma Reesei* Cellulases and Other Hydrolases, Proceedings of the Tricel93 Symposium Espoo, Finland, pp.: 139–146 (Jun. 1993).

*Takkinen, et al., "An Active single–chain antibody containing a cellulase linker domain is secreted by *Escherichia coli*" Protein engineering 4(7):837–841 (1991).

*Teeri et al., "Homologous domains in *Trichoderma reesei* cellulolytic enzymes: gene sequence and expression of cellobiohydrolase II" Gene 51:43–52 (1987).

*Schülein, "Cellulases of *Trichoderma reesei*" Methods in Enzymology 160:234–242 (1988).

*Schülein et al., "*Humicola insolens* Alkaline Cellulases" *Trichoderma Reesei* Cellulases and Other Hydrolases, Proceedings of the Tricel93 Symposium Espoo, Finland, pp.: 109–116 (Jun. 1993).

*Sprey et al., "Isolation and properties of a low molecular mass endoglucanase from *Trichoderma reesei*" FEMS Microbiol. Letters 92:253–258 (1992).

*Stahlberg et al., "A binding–site–deficient, catalytically active, core protein of endoglucanase III from the culture filtrate of *Trichoderma reesei*" Eur. J. Biochem 173:179–183 (1988).

*Tomme et al., "Studies of the celluloytic system of *Trichoderma reesei* QM 9414" Eur. J. Biochem. 170:575–581 (1988).

*Ulker et al., "Characterization of an Unglycosylated Low Molecular Weight 1,4–b–glucan–glucanohydrolase of *Trichoderma reesei*" FEMS Microbiology Letters 69:215–219 (1990).

*Ward et al., "Cloning, Sequence and Preliminary Structural Analysis of a Small, High pI Endoglucanase (EGIII) from *Trichoderma reesei*" *Trichoderma Reesei* Cellulases and Other Hydrolases, Proceedings of the Tricel93 Symposium Espoo, Finland, pp.: 153–158 (Jun. 1993).

*Wood, "Properties of Cellulolytic Enzyme Systems" Biochem. Soc. Trans. 13(2):407–410 (1985).

*Bedford, M., "Feed Enzymes in Barley–Based Diets" *J. or the Science of Food and Agriculture* 63(1):107–108 (1993).

```
                CTCCACACCCGGTGCCGTGCGCGGAAGCTGCTCCACCAGCTCCGGTGTCC
                ┼────┼────┼────┼────┼────┼────┼────┼────┼────┼─── 1600
   Ser Thr Pro Gly Ala Val Arg Gly Ser Cys Ser Thr Ser Ser Gly Val
                CTGCTCAGGTCGAATCTCAGTCTCCCAACGCCAAGGTCACCTTCTCCAAC
                ┼────┼────┼────┼────┼────┼────┼────┼────┼────┼─── 1650
 Pro Ala Gln Val Glu Ser Gln Ser Pro Asn Ala Lys Val Thr Phe Ser Asn
                ATCAAGTTCGGACCCATTGGCAGCACCGGCAACCCTAGCGGCGGCAACCC
                ┼────┼────┼────┼────┼────┼────┼────┼────┼────┼─── 1700
    Ile Lys Phe Gly Pro Ile Gly Ser Thr Gly Asn Pro Ser Gly Gly Asn Pro
                TCCCGGCGGAAACCGTGGCACCACCACCACCCGCCGCCCAGCCACTACCA
                ┼────┼────┼────┼────┼────┼────┼────┼────┼────┼─── 1750
      Pro Gly Gly Asn Arg Gly Thr Thr Thr Thr Arg Arg Pro Ala Thr Thr
                CTGGAAGCTCTCCCGGACCTACCCAGTCTCACTACGGCCAGTGCGGCGGT
                ┼────┼────┼────┼────┼────┼────┼────┼────┼────┼─── 1800
Thr Gly Ser Ser Pro Gly Pro Thr Gln Ser His Tyr Gly Gln Cys Gly Gly
                ATTGGCTACAGCGGCCCCACGGTCTGCGCCAGCGGCACAACTTGCCAGGT
                ┼────┼────┼────┼────┼────┼────┼────┼────┼────┼─── 1850
     Ile Gly Tyr Ser Gly Pro Thr Val Cys Ala Ser Gly Thr Thr Cys Gln Val
                CCTGAACCCTTACTACTCTCAGTGCCTGTAAAGCTCCGTGCGAAAGCCTG
                ┼────┼────┼────┼────┼────┼────┼────┼────┼────┼─── 1900
     Leu Asn Pro Tyr Tyr Ser Gln Cys Leu •
                ACGCACCGGTAGATTCTTGGTGAGCCCGTATCATGACGGCGGCGGGAGCT
                ┼────┼────┼────┼────┼────┼────┼────┼────┼────┼─── 1950
                ACATGGCCCCGGGTGATTTATTTTTTTTGTATCTACTTCTGACCCTTTTC
                ┼────┼────┼────┼────┼────┼────┼────┼────┼────┼─── 2000
                AAATATACGGTCAACTCATCTTTCACTGGAGATGCGGCCTGCTTGGTATT
                ┼────┼────┼────┼────┼────┼────┼────┼────┼────┼─── 2050
                GCGATGTTGTCAGCTTGGCAAATTGTGGCTTTCGAAAACACAAAACGATT
                ┼────┼────┼────┼────┼────┼────┼────┼────┼────┼─── 2100
                CCTTAGTAGCCATGCATTTTAAGATAACGGAATAGAAGAAAGAGGAAATT
                ┼────┼────┼────┼────┼────┼────┼────┼────┼────┼─── 2150
                AAAAAAAAAAAAAAAACAAACATCCCGTTCATAACCCGTAGAATCGCCGC
                ┼────┼────┼────┼────┼────┼────┼────┼────┼────┼─── 2200
                TCTTCGTGTATCCCAGTACCA
                ┼────┼────┼────┼───→ 2221
```

```
AAGCTTAGCCAAGAACAATAGCCGATAAAGATAGCCTCATTAAACGGAAT
                                                   50
GAGCTAGTAGGCAAAGTCAGCGAATGTGTATATATAAAGGTTCGAGGTCC
                                                   100
GTGCCTCCCTCATGCTCTCCCCATCTACTCATCAACTCAGATCCTCCAGG
                                                   150
AGACTTGTACACCATNTTTTGAGGCACAGAAACCCAATAGTCAACCGCGG
                                                   200
ACTGGCATCATGTATCGGAAGTTGGCCGTCATCTCGGCCTTCTTGGCCAC
                                                   250
```
          Met Tyr Arg Lys Leu Ala Val Ile Ser Ala Phe Leu Ala Thr
```
AGCTCGTGCTCAGTCGGCCTGCACTCTCCAATCGGAGACTCACCCGCCTC
                                                   300
```
Ala Arg Ala Gln Ser Ala Cys Thr Leu Gln Ser Glu Thr His Pro Pro
```
TGACATGGCAGAAATGCTCGTTTGGTGGCACTTGCACTCAACAGACAGGC
                                                   350
```
Leu Thr Trp Gln Lys Cys Ser Ser Gly Gly Thr Cys Thr Gln Gln Thr Gly
```
TCCGTGGTCATCGACGCCAACTGGCGCTGGACTCACGCTACGAACAGCAG
                                                   400
```
Ser Val Val Ile Asp Ala Asn Trp Arg Trp Thr His Ala Thr Asn Ser Ser
```
CACGAACTGCTACGATGGCAACACTTGGAGCTCGACCCTATGTCCTGACA
                                                   450
```
Thr Asn Cys Tyr Asp Gly Asn Thr Trp Ser Ser Thr Leu Cys Pro Asp
```
ACGAGACCTGCGCGAAGAACTGCTGTCTGGACGGTGCCGCCTACGCGTCC
                                                   500
```
Asn Glu Thr Cys Ala Lys Asn Cys Cys Leu Asp Gly Ala Ala Tyr Ala Ser
```
ACGTACGGAGTTACCACGAGCGGTAACAGCCTCTCCATTGGCTTTGTCAC
                                                   550
```
Thr Tyr Gly Val Thr Thr Ser Gly Asn Ser Leu Ser Ile Gly Phe Val Thr
```
CCAGTCTGCGCAGAAGAACGTTGGCGCTCGCCTTTACCTTATGGCGAGCG
                                                   600
```
Gln Ser Ala Gln Lys Asn Val Gly Ala Arg Leu Tyr Leu Met Ala Ser
```
ACACGACCTACCAGGAATTCACCCTGCTTGGCAACGAGTTCTCTTTCGAT
                                                   650
```
Asp Thr Thr Tyr Gln Glu Phe Thr Leu Leu Gly Asn Glu Phe Ser Phe Asp
```
GTTGATGTTTCGCAGCTGCCGTAAGTGACTTACCATGAACCCCTGACGTA
                                                   700
```
Val Asp Val Ser Gln Leu Pro
```
TCTTCTTGTGGGCTCCCAGCTGACTGGCCAATTTAAGGTGCGGCTTGAAC
                                                   750
```
                                           Cys Gly Leu Asn
```
GGAGCTCTCTACTTCGTGTCCATGGACGCGGATGGTGGCGTGAGCAAGTA
                                                   800
```
Gly Ala Leu Tyr Phe Val Ser Met Asp Ala Asp Gly Gly Val Ser Lys Tyr

FIG._1A

```
                TCCCACCAACACCGCTGGCGCCAAGTACGGCACGGGGTACTGTGACAGCC
                                                                    850
      Pro Thr Asn Thr Ala Gly Ala Lys Tyr Gly Thr Gly Tyr Cys Asp Ser
                AGTGTCCCCGCGATCTGAAGTTCATCAATGGCCAGGCCAACGTTGAGGGC
                                                                    900
      Gln Cys Pro Arg Asp Leu Lys Phe Ile Asn Gly Gln Ala Asn Val Glu Gly
                TGGGAGCCGTCATCCAACAACGCAAACACGGGCATTGGAGGACACGGAAG
                                                                    950
      Trp Glu Pro Ser Ser Asn Asn Ala Asn Thr Gly Ile Gly Gly His Gly Ser
                CTGCTGCTCTGAGATGGATATCTGGGAGGCCAACTCCATCTCCGAGGCTC
                                                                    1000
       Cys Cys Ser Glu Met Asp Ile Trp Glu Ala Asn Ser Ile Ser Glu Ala
                TTACCCCCCACCCTTGCACGACTGTCGGCCAGGAGATCTGCGAGGGTGAT
                                                                    1050
    Leu Thr Pro His Pro Cys Thr Thr Val Gly Gln Glu Ile Cys Glu Gly Asp
                GGGTGCGGCGGAACTTACTCCGATAACAGATATGGCGGCACTTGCGATCC
                                                                    1100
       Gly Cys Gly Gly Thr Tyr Ser Asp Asn Arg Tyr Gly Gly Thr Cys Asp Pro
                CGATGGCTGCGACTGGAACCCATACCGCCTGGGCAACACCAGCTTCTACG
                                                                    1150
       Asp Gly Cys Asp Trp Asn Pro Tyr Arg Leu Gly Asn Thr Ser Phe Tyr
                GCCCTGGCTCAAGCTTTACCCTCGATACCACCAAGAAATTGACCGTTGTC
                                                                    1200
    Gly Pro Gly Ser Ser Phe Thr Leu Asp Thr Thr Lys Lys Leu Thr Val Val
                ACCCAGTTCGAGACGTCGGGTGCCATCAACCGATACTATGTCCAGAATGG
                                                                    1250
      Thr Gln Phe Glu Thr Ser Gly Ala Ile Asn Arg Tyr Tyr Val Gln Asn Gly
                CGTCACTTTCCAGCAGCCCAACGCCGAGCTTGGTAGTTACTCTGGCAACG
                                                                    1300
       Val Thr Phe Gln Gln Pro Asn Ala Glu Leu Gly Ser Tyr Ser Gly Asn
                AGCTCAACGATGATTACTGCACAGCTGAGGAGGCAGAATTCGGCGGATCC
                                                                    1350
    Glu Leu Asn Asp Asp Tyr Cys Thr Ala Glu Glu Ala Glu Phe Gly Gly Ser
                TCTTTCTCAGACAAGGGCGGCCTGACTCAGTTCAAGAAGGCTACCTCTGG
                                                                    1400
     Ser Phe Ser Asp Lys Gly Gly Leu Thr Gln Phe Lys Lys Ala Thr Ser Gly
                CGGCATGGTTCTGGTCATGAGTCTGTGGGATGATGTGAGTTTGATGGACA
                                                                    1450
      Gly Met Val Leu Val Met Ser Leu Trp Asp Asp
                AACATGCGCGTTGACAAAGAGTCAAGCAGCTGACTGAGATGTTACAGTAC
                                                                    1500
                                                               Tyr
                TACGCCAACATGCTGTGGCTGGACTCCACCTACCCGACAAACGAGACCTC
                                                                    1550
     Tyr Ala Asn Met Leu Trp Leu Asp Ser Thr Tyr Pro Thr Asn Glu Thr Ser
```

FIG._1B

```
AGCCCAGTAGCGTGTTTGAATCAGTTCACAATCTCTCCTAAACACAGTCC
                                                    3850
GACACTAGGTAGGTACGTTGTAATAGCAACTCAAACATGTAATTCGTTTC
                                                    3900
AAGGCAGGAACATTTTATAAACTTCCCTGCGATTTAATCAATAAAGATCC
                                                    3950
TAGTCCAATCGTATACTACCTACCTAGCTAAGGTAGGTAGGTAGTTCGTG
                                                    4000
GGAACCTGGTCGCTAATTCACGCAACCCACTTTGCGCTCTTCGCCTGGCC
                                                    4050
GTCGTTGAAGGTAAAGCAGTTGTACCCATCACCTAACTCAACCGACACCG
                                                    4100
TTGATCTGCTCAAGGCAGTTTTC
                       → 4123
```

FIG._2E

| FIG._2A |
|---------|
| FIG._2B |
| FIG._2C |
| FIG._2D |
| FIG._2E |

FIG._2

```
GAATTCTAGGCTAGGTATGCGAGGCACGCGGATCTAGGGCAGACTGGGCA
                                                  50
TTGCATAGCTATGGTGTAGTAGAACTCCCGTCAACGGCTATTCTCACCTA
                                                  100
GACTTTCCCCTTCGAACTGACAAGTTGTTATATTGCCTGTGTACCAAGCG
                                                  150
CTAATGTGGACAGGATTAATGCCAGAGTTCATTAGCCTCAAGTAGAGCCT
                                                  200
ATTTCCTCGCCGGAAAGTCATCTCTCTTATTGCATTTCTGCCTTCCACTA
                                                  250
ACTCAGGGTGCAGCGCAACACTACACGCAACATATCACATTTATTAGCCG
                                                  300
TGCAACAAGGCTATTCTACGAAAAATGCTACACTCCACATGTTAAAGGCG
                                                  350
CATTCAACCAGCTTCTTTATTGGGTAATATACAGCCAGGCGGGGATGAAG
                                                  400
CTCATTAGCCGCCACTCAAGGCTATACAATGTTGCCAACTCTCCGGGCTT
                                                  450
TATCCTGTGCTCCCGAATACCACATCGTGATGATGCTTCAGCGCACGGAA
                                                  500
GTCACAGACACCGCCTGTATAAAAGGGGGACTGTGACCCTGTATGAGGCG
                                                  550
CAACATGGTCTCACAGCAGCTCACCTGAAGAGGCTTGTAAGATCACCCTC
                                                  600
TGTGTATTGCACCATGATTGTCGGCATTCTCACCACGCTGGCTACGCTGG
                                                  650
              Met Ile Val Gly Ile Leu Thr Thr Leu Ala Thr Leu
CCACACTCGCAGCTAGTGTGCCTCTAGAGGAGCGGCAAGCTTGCTCAAGC
                                                  700
Ala Thr Leu Ala Ala Ser Val Pro Leu Glu Glu Arg Gln Ala Cys Ser Ser
GTCTGGTAATTATGTGAACCCTCTCAAGAGACCCAAATACTGAGATATGT
                                                  750
Val Trp
CAAGGGGCCAATGTGGTGGCCAGAATTGGTCGGGTCCGACTTGCTGTGCT
                                                  800
        Gly Gln Cys Gly Gly Gln Asn Trp Ser Gly Pro Thr Cys Cys Ala
TCCGGAAGCACATGCGTCTACTCCAACGACTATTACTCCCAGTGTCTTCC
                                                  850
Ser Gly Ser Thr Cys Val Tyr Ser Asn Asp Tyr Tyr Ser Gln Cys Leu Pro
CGGCGCTGCAAGCTCAAGCTCGTCCACGCGCGCCGCGTCGACGACTTCTC
                                                  900
Gly Ala Ala Ser Ser Ser Ser Ser Thr Arg Ala Ala Ser Thr Thr Ser
GAGTATCCCCCACAACATCCCGGTCGAGCTCCGCGACGCCTCCACCTGGT
                                                  950
Arg Val Ser Pro Thr Thr Ser Arg Ser Ser Ser Ala Thr Pro Pro Pro Gly
```

FIG._2A

```
TCTACTACTACCAGAGTACCTCCAGTCGGATCGGGAACCGCTACGTATTC
                                                    1000
 Ser Thr Thr Thr Arg Val Pro Pro Val Gly Ser Gly Thr Ala Thr Tyr Ser
AGGCAACCCTTTTGTTGGGGTCACTCCTTGGGCCAATGCATATTACGCCT
                                                    1050
  Gly Asn Pro Phe Val Gly Val Thr Pro Trp Ala Asn Ala Tyr Tyr Ala
CTGAAGTTAGCAGCCTCGCTATTCCTAGCTTGACTGGAGCCATGGCCACT
                                                    1100
 Ser Glu Val Ser Ser Leu Ala Ile Pro Ser Leu Thr Gly Ala Met Ala Thr
GCTGCAGCAGCTGTCGCAAAGGTTCCCTCTTTTATGTGGCTGTAGGTCCT
                                                    1150
  Ala Ala Ala Ala Val Ala Lys Val Pro Ser Phe Met Trp Leu
CCCGGAACCAAGGCAATCTGTTACTGAAGGCTCATCATTCACTGCAGAGA
                                                    1200
                                                      Asp
TACTCTTGACAAGACCCCTCTCATGGAGCAAACCTTGGCCGACATCCGCA
                                                    1250
   Thr Leu Asp Lys Thr Pro Leu Met Glu Gln Thr Leu Ala Asp Ile Arg
CCGCCAACAAGAATGGCGGTAACTATGCCGGACAGTTTGTGGTGATAGAC
                                                    1300
 Thr Ala Asn Lys Asn Gly Gly Asn Tyr Ala Gly Gln Phe Val Val Ile Asp
TTGCCGGATCGCGATTGCGCTGCCCTTGCCTCGAATGGCGAATACTCTAT
                                                    1350
  Leu Pro Asp Arg Asp Cys Ala Ala Leu Ala Ser Asn Gly Glu Tyr Ser Ile
TGCCGATGGTGGCGTCGCCAAATATAAGAACTATATCGACACCATTCGTC
                                                    1400
   Ala Asp Gly Gly Val Ala Lys Tyr Lys Asn Tyr Ile Asp Thr Ile Arg
AAATTGTCGTGGAATATTCCGATATCCGGACCCTCCTGGTTATTGGTATG
                                                    1450
  Gln Ile Val Val Glu Tyr Ser Asp Ile Arg Thr Leu Leu Val Ile
AGTTTAAACACCTGCCTCCCCCCCCCCTTCCCTTCCTTTCCCGCCGGCAT
                                                    1500

CTTGTCGTTGTGCTAACTATTGTTCCCTCTTCCAGAGCCTGACTCTCTTG
                                                    1550
                                   Glu Pro Asp Ser Leu
CCAACCTGGTGACCAACCTCGGTACTCCAAAGTGTGCCAATGCTCAGTCA
                                                    1600
 Ala Asn Leu Val Thr Asn Leu Gly Thr Pro Lys Cys Ala Asn Ala Gln Ser
GCCTACCTTGAGTGCATCAACTACGCCGTCACACAGCTGAACCTTCCAAA
                                                    1650
  Ala Tyr Leu Glu Cys Ile Asn Tyr Ala Val Thr Gln Leu Asn Leu Pro Asn
TGTTGCGATGTATTTGGACGCTGGCCATGCAGGATGGCTTGGCTGGCCGG
                                                    1700
  Val Ala Met Tyr Leu Asp Ala Gly His Ala Gly Trp Leu Gly Trp Pro
```

FIG._2B

```
                  CAAACCAAGACCCGGCCGCTCAGCTATTTGCAAATGTTTACAAGAATGCA
                  ─────────────────────────────────────────────────── 1750
    Ala Asn Gln Asp Pro Ala Ala Gln Leu Phe Ala Asn Val Tyr Lys Asn Ala
                  TCGTCTCCGAGAGCTCTTCGCGGATTGGCAACCAATGTCGCCAACTACAA
                  ─────────────────────────────────────────────────── 1800
    Ser Ser Pro Arg Ala Leu Arg Gly Leu Ala Thr Asn Val Ala Asn Tyr Asn
                  CGGGTGGAACATTACCAGCCCCCCATCGTACACGCAAGGCAACGCTGTCT
                  ─────────────────────────────────────────────────── 1850
      Gly Trp Asn Ile Thr Ser Pro Pro Ser Tyr Thr Gln Gly Asn Ala Val
                  ACAACGAGAAGCTGTACATCCACGCTATTGGACCTCTTCTTGCCAATCAC
                  ─────────────────────────────────────────────────── 1900
    Tyr Asn Glu Lys Leu Tyr Ile His Ala Ile Gly Pro Leu Leu Ala Asn His
                  GGCTGGTCCAACGCCTTCTTCATCACTGATCAAGGTCGATCGGGAAAGCA
                  ─────────────────────────────────────────────────── 1950
     Gly Trp Ser Asn Ala Phe Phe Ile Thr Asp Gln Gly Arg Ser Gly Lys Gln
                  GCCTACCGGACAGCAACAGTGGGGAGACTGGTGCAATGTGATCGGCACCG
                  ─────────────────────────────────────────────────── 2000
         Pro Thr Gly Gln Gln Gln Trp Gly Asp Trp Cys Asn Val Ile Gly Thr
                  GATTTGGTATTCGCCCATCCGCAAACACTGGGGACTCGTTGCTGGATTCG
                  ─────────────────────────────────────────────────── 2050
    Gly Phe Gly Ile Arg Pro Ser Ala Asn Thr Gly Asp Ser Leu Leu Asp Ser
                  TTTGTCTGGGTCAAGCCAGGCGGCGAGTGTGACGGCACCAGCGACAGCAG
                  ─────────────────────────────────────────────────── 2100
     Phe Val Trp Val Lys Pro Gly Gly Glu Cys Asp Gly Thr Ser Asp Ser Ser
                  TGCGCCACGATTTGACTCCCACTGTGCGCTCCCAGATGCCTTGCAACCGG
                  ─────────────────────────────────────────────────── 2150
       Ala Pro Arg Phe Asp Ser His Cys Ala Leu Pro Asp Ala Leu Gln Pro
                  CGCCTCAAGCTGGTGCTTGGTTCCAAGCCTACTTTGTGCAGCTTCTCACA
                  ─────────────────────────────────────────────────── 2200
    Ala Pro Gln Ala Gly Ala Trp Phe Gln Ala Tyr Phe Val Gln Leu Leu Thr
                  AACGCAAACCCATCGTTCCTGTAAGGCTTTCGTGACCGGGCTTCAAACAA
                  ─────────────────────────────────────────────────── 2250
    Asn Ala Asn Pro Ser Phe Leu
                  TGATGTGCGATGGTGTGGTTCCCGGTTGGCGGAGTCTTTGTCTACTTTGG
                  ─────────────────────────────────────────────────── 2300
                  TTGTCTGTCGCAGGTCGGTAGACCGCAAATGAGCAACTGATGGATTGTTG
                  ─────────────────────────────────────────────────── 2350
                  CCAGCGATACTATAATTCACATGGATGGTCTTTGCGATCAGTAGCTAGTG
                  ─────────────────────────────────────────────────── 2400
                  AGAGAGAGAGAACATCTATCCACAATGTCGAGTGTCTATTAGACATACTC
                  ─────────────────────────────────────────────────── 2450
                  CGAGAATAAAGTCAACTGTGTCTGTGATCTAAAGATCGATTCGGCAGTCG
                  ─────────────────────────────────────────────────── 2500
                  AGTAGCGTATAACAACTCCGAGTACCAGCAAAAGCACGTCGTGACAGGAG
                  ─────────────────────────────────────────────────── 2550
                  CAGGCTTTGCCAACTGCGCAACCTTGCTTGAATGAGGATACACGGGGTGC
                  ─────────────────────────────────────────────────── 2600
```

FIG._2C

```
AACATGGCTGTACTGATCCATCGCAACCAAAATTTCTGTTTATAGATCAA
                                                   2650
GCTGGTAGATTCCAATTACTCCACCTCTTGCGCTTCTCCATGACATGTAA
                                                   2700
GTGCACGTAGGAAACCATACCCAAATTGCCTACAGCTGCGGAGCATGAGC
                                                   2750
CTATGGCGATCAGTCTGGTCATGTTAACCAGCCTGTGCTCTGACGTTAAT
                                                   2800
GCAGAATAGAAAGCCGCGGTTGCAATGCAAATGATGATGCCTTTGCAGAA
                                                   2850
ATGGCTTGCTCGCTGACTGATACCAGTAACAACTTTGCTTGGCCGTCTAG
                                                   2900
CGCTGTTGATTGTATTCATCACAACCTCGTCTCCCTCCTTTGGGTTGAGC
                                                   2950
TCTTTGGATGGCTTTCCAAACGTTAATAGCGCGTTTTCTCCACAAAGTA
                                                   3000
TTCGTATGGACGCGCTTTTGGCTGTATTGCGTGAGCTACCAGCAGCCCAA
                                                   3050
TTGGCGAAGTCTTGAGCCGCACTCGCATAGAATAATTGATTGCGCATTTG
                                                   3100
ATGCGATTTTTGAGCGGCTGTTTCAGGCGACATTTCGCCGCCTTTATTTG
                                                   3150
CTCCATTATATCATCGATGGCATGTCCAATAGCCCGGTGATAGTCTTGTC
                                                   3200
GAATATGGCTGTCGTGGATAACCCATCGGCAGCAGATGATAATGATTCCG
                                                   3250
CAGCACAAGCTCGTATGTGGGTAGCAGAAGAACTGAGCGAGATCTTCGAG
                                                   3300
GGCGTAACTCTGCATATCCGATTGGCCTGCTGCCACATGTCATTTTGCTT
                                                   3350
CGGTTTCTTTTCTGTTGAGTTCTTGTATTTGGGTGAAAGTAACATGGTGT
                                                   3400
ATGACGAGAGACATTGGTGGTAAGAAAAAATTTCACCTCCTCTTAGTGCA
                                                   3450
GGACTGACTCTCAAAATCTATATGCAAATGTGTCGTGTAACACCCTTCGC
                                                   3500
ATGAGCGCTGACCGTACCCTACCATTTCGCCCCACTCATGATAGCAGAAG
                                                   3550
AGACATATTAATTCGGCAATGCTACGAAAGTCTGCAGGCTATGCTTAAAT
                                                   3600
AAACGCTTGCCACAGAAGCCGACAGTTTATTGTTACTACTTACTATACTG
                                                   3650
TATTATTGTTGCTCACATAAGGCGGTGAACCATTGGTTCACACGACGCCT
                                                   3700
GACGAGGTAAATTACTCTCTCGTAGGGCTGCCAAGGTAGGTCCCAACCCC
                                                   3750
GTATCCTCGGTCGAGGGTGCGAGGTTCTTTGGTCCTTCCCTCTTTGGTAA
                                                   3800
```

FIG._2D

```
CCCCATGCCTGACGGGAGTGATTTTGAGATGCTAACCGCTAAAATACAGA
                                                  1600
                                               Tyr
CTACTCGCAATGCCTTTAGAGCGTTGACTTGCCTCTGGTCTGTCCAGACG
                                                  1650
Tyr Ser Gln Cys Leu
GGGGCACGATAGAATGCGGGCACGCAGGGA
                             → 1680
```

```
TGTGTTGAAATCCAACTTATAAAGACAACAACCGCAAACTTTGTCTTGTG
                                                    50
CCATCAGATTGTTGCCAAGCACCGTCCCCCCCCCTATCTTAGTCCTTCT
                                                    100
TGTTGTCCCAAAATGGCGCCCTCAGTTACACTGCCGTTGACCACGGCCAT
                                                    150
                    Met Ala Pro Ser Val Thr Leu Pro Leu Thr Thr Ala Ile
CCTGGCCATTGCCCGGCTCGTCGCCGCCCAGCAACCGGGTACCAGCACCC
                                                    200
Leu Ala Ile Ala Arg Leu Val Ala Ala Gln Gln Pro Gly Thr Ser Thr
CCGAGGTCCATCCCAAGTTGACAACCTACAAGTGTACAAAGTCCGGGGGG
                                                    250
Pro Glu Val His Pro Lys Leu Thr Thr Tyr Lys Cys Thr Lys Ser Gly Gly
TGCGTGGCCCAGGACACCTCGGTGGTCCTTGACTGGAACTACCGCTGGAT
                                                    300
Cys Val Ala Gln Asp Thr Ser Val Val Leu Asp Trp Asn Tyr Arg Trp Met
GCACGACGCAAACTACAACTCGTGCACCGTCAACGGCGGCGTCAACACCA
                                                    350
    His Asp Ala Asn Tyr Asn Ser Cys Thr Val Asn Gly Gly Val Asn Thr
CGCTCTGCCCTGACGAGGCGACCTGTGGCAAGAACTGCTTCATCGAGGGC
                                                    400
Thr Leu Cys Pro Asp Glu Ala Thr Cys Gly Lys Asn Cys Phe Ile Glu Gly
GTCGACTACGCCGCCTCGGGCGTCACGACCTCGGGCAGCAGCCTCACCAT
                                                    450
Val Asp Tyr Ala Ala Ser Gly Val Thr Thr Ser Gly Ser Ser Leu Thr Met
GAACCAGTACATGCCCAGCAGCTCTGGCGGCTACAGCAGCGTCTCTCCTC
                                                    500
   Asn Gln Tyr Met Pro Ser Ser Ser Gly Gly Tyr Ser Ser Val Ser Pro
GGCTGTATCTCCTGGACTCTGACGGTGAGTACGTGATGCTGAAGCTCAAC
                                                    550
Arg Leu Tyr Leu Leu Asp Ser Asp Gly Glu Tyr Val Met Leu Lys Leu Asn
GGCCAGGAGCTGAGCTTCGACGTCGACCTCTCTGCTCTGCCGTGTGGAGA
                                                    600
Gly Gln Glu Leu Ser Phe Asp Val Asp Leu Ser Ala Leu Pro Cys Gly Glu
GAACGGCTCGCTCTACCTGTCTCAGATGGACGAGAACGGGGGCGCCAACC
                                                    650
Asn Gly Ser Leu Tyr Leu Ser Gln Met Asp Glu Asn Gly Gly Ala Asn
AGTATAACACGGCCGGTGCCAACTACGGGAGCGGCTACTGCGATGCTCAG
                                                    700
Gln Tyr Asn Thr Ala Gly Ala Asn Tyr Gly Ser Gly Tyr Cys Asp Ala Gln
TGCCCCGTCCAGACATGGAGGAACGGCACCCTCAACACTAGCCACCAGGG
                                                    750
Cys Pro Val Gln Thr Trp Arg Asn Gly Thr Leu Asn Thr Ser His Gln Gly
CTTCTGCTGCAACGAGATGGATATCCTGGAGGGCAACTCGAGGGCGAATG
                                                    800
Phe Cys Cys Asn Glu Met Asp Ile Leu Glu Gly Asn Ser Arg Ala Asn
```

FIG._3A

```
CCTTGACCCCTCACTCTTGCACGGCCACGGCCTGCGACTCTGCCGGTTGC
                                                    850
Ala Leu Thr Pro His Ser Cys Thr Ala Thr Ala Cys Asp Ser Ala Gly Cys
GGCTTCAACCCCTATGGCAGCGGCTACAAAAGGTGAGCCTGATGCCACTA
                                                    900
Gly Phe Asn Pro Tyr Gly Ser Gly Tyr Lys Ser
CTACCCCTTTCCTGGCGCTCTCGCGGTTTTCCATGCTGACATGGTTTTCC
                                                    950

AGCTACTACGGCCCCGGAGATACCGTTGACACCTCCAAGACCTTCACCAT
                                                    1000
    Tyr Tyr Gly Pro Gly Asp Thr Val Asp Thr Ser Lys Thr Phe Thr Ile
CATCACCCAGTTCAACACGGACAACGGCTCGCCCTCGGGCAACCTTGTGA
                                                    1050
Ile Thr Gln Phe Asn Thr Asp Asn Gly Ser Pro Ser Gly Asn Leu Val
GCATCACCCGCAAGTACCAGCAAAACGGCGTCGACATCCCCAGCGCCCAG
                                                    1100
Ser Ile Thr Arg Lys Tyr Gln Gln Asn Gly Val Asp Ile Pro Ser Ala Gln
CCCGGCGGCGACACCATCTCGTCCTGCCCGTCCGCCTCAGCCTACGGCGG
                                                    1150
Pro Gly Gly Asp Thr Ile Ser Ser Cys Pro Ser Ala Ser Ala Tyr Gly Gly
CCTCGCCACCATGGGCAAGGCCCTGAGCAGCGGCATGGTGCTCGTGTTCA
                                                    1200
Leu Ala Thr Met Gly Lys Ala Leu Ser Ser Gly Met Val Leu Val Phe
GCATTTGGAACGACAACAGCCAGTACATGAACTGGCTCGACAGCGGCAAC
                                                    1250
Ser Ile Trp Asn Asp Asn Ser Gln Tyr Met Asn Trp Leu Asp Ser Gly Asn
GCCGGCCCCTGCAGCAGCACCGAGGGCAACCCATCCAACATCCTGGCCAA
                                                    1300
Ala Gly Pro Cys Ser Ser Thr Glu Gly Asn Pro Ser Asn Ile Leu Ala Asn
CAACCCCAACACGCACGTCGTCTTCTCCAACATCCGCTGGGGAGACATTG
                                                    1350
Asn Pro Asn Thr His Val Val Phe Ser Asn Ile Arg Trp Gly Asp Ile
GGTCTACTACGAACTCGACTGCGCCCCCGCCCCCGCCTGCGTCCAGCACG
                                                    1400
Gly Ser Thr Thr Asn Ser Thr Ala Pro Pro Pro Pro Pro Ala Ser Ser Thr
ACGTTTTCGACTACACCGAGGAGCTCGACGACTTCGAGCAGCCCGAGCTG
                                                    1450
Thr Phe Ser Thr Thr Pro Arg Ser Ser Thr Thr Ser Ser Ser Pro Ser Cys
CACGCAGACTCACTGGGGGCAGTGCGGTGGCATTGGGTACAGCGGGTGCA
                                                    1500
Thr Gln Thr His Trp Gly Gln Cys Gly Gly Ile Gly Tyr Ser Gly Cys
AGACGTGCACGTCGGGCACTACGTGCCAGTATAGCAACGACTGTTCGTAT
                                                    1550
Lys Thr Cys Thr Ser Gly Thr Thr Cys Gln Tyr Ser Asn Asp
```

*FIG._3B*

```
ATAGCACGTATGTCCTGACGGAAACACCGACTAGCAGTGGTAACTCATGG
                                                    1650
Asp Ser Thr Tyr Val Leu Thr Glu Thr Pro Thr Ser Ser Gly Asn Ser Trp
ACGGACACATCCTTGGTCAGCTCGTGTCTCGCAAGAAAGTAGCACTCTGA
                                                    1700
Thr Asp Thr Ser Leu Val Ser Ser Cys Leu Ala Arg Lys
GCTGAATGCAGAAGCCTCGCCAACGTTTGTATCTCGCTATCAAACATAGT
                                                    1750
AGCTACTCTATGAGGCTGTCTGTTCTCGATTTCAGCTTTATATAGTTTCA
                                                    1800
TCAAACAGTACATATTCCCTCTGTGGCCACGCAAAAAAAAAAAAAAAAA
                                                    1849
```

```
TGCCATTTCTGACCTGGATAGGTTTTCCTATGGTCATTCCTATAAGAGAC
                                                    50
ACGCTCTTTCGTCGGCCCGTAGATATCAGATTGGTATTCAGTCGCACAGA
                                                    100
CGAAGGTGAGTTGATCCTCCAACATGAGTTCTATGAGCCCCCCCCTTGCC
                                                    150
CCCCCCCGTTCACCTTGACCTGCAATGAGAATCCCACCTTTTACAAGAGC
                                                    200
ATCAAGAAGTATTAATGGCGCTGAATAGCCTCTGCTCGATAATATCTCCC
                                                    250
CGTCATCGACAATGAACAAGTCCGTGGCTCCATTGCTGCTTGCAGCGTCC
                                                    300
           Met Asn Lys Ser Val Ala Pro Leu Leu Leu Ala Ala Ser
ATACTATATGGCGGCGCCGTCGCACAGCAGACTGTCTGGGGCCAGTGTGG
                                                    350
 Ile Leu Tyr Gly Gly Ala Val Ala Gln Gln Thr Val Trp Gly Gln Cys Gly
AGGTATTGGTTGGAGCGGACCTACGAATTGTGCTCCTGGCTCAGCTTGTT
                                                    400
    Gly Ile Gly Trp Ser Gly Pro Thr Asn Cys Ala Pro Gly Ser Ala Cys
CGACCCTCAATCCTTATTATGCGCAATGTATTCCGGGAGCCACTACTATC
                                                    450
Ser Thr Leu Asn Pro Tyr Tyr Ala Gln Cys Ile Pro Gly Ala Thr Thr Ile
ACCACTTCGACCCGGCCACCATCCGGTCCAACCACCACCACCAGGGCTAC
                                                    500
Thr Thr Ser Thr Arg Pro Pro Ser Gly Pro Thr Thr Thr Thr Arg Ala Thr
CTCAACAAGCTCATCAACTCCACCCACGAGCTCTGGGGTCCGATTTGCCG
                                                    550
    Ser Thr Ser Ser Ser Thr Pro Pro Thr Ser Ser Gly Val Arg Phe Ala
GCGTTAACATCGCGGGTTTTGACTTTGGCTGTACCACAGAGTGAGTACCC
                                                    600
Gly Val Asn Ile Ala Gly Phe Asp Phe Gly Cys Thr Thr Asp
TTGTTTCCTGGTGTTGCTGGCTGGTTGGGCGGGTATACAGCGAAGCGGAC
                                                    650
GCAAGAACACCGCCGGTCCGCCACCATCAAGATGTGGGTGGTAAGCGGCG
                                                    700
GTGTTTTGTACAACTACCTGACAGCTCACTCAGGAAATGAGAATTAATGG
                                                    750
AAGTCTTGTTACAGTGGCACTTGCGTTACCTCGAAGGTTTATCCTCCGTT
                                                    800
                    Gly Thr Cys Val Thr Ser Lys Val Tyr Pro Pro Leu
GAAGAACTTCACCGGCTCAAACAACTACCCCGATGGCATCGGCCAGATGC
                                                    850
Lys Asn Phe Thr Gly Ser Asn Asn Tyr Pro Asp Gly Ile Gly Gln Met
```

FIG._4A

```
AGCACTTCGTCAACGAGGACGGGATGACTATTTTCCGCTTACCTGTCGGA
                                                  900
Gln His Phe Val Asn Glu Asp Gly Met Thr Ile Phe Arg Leu Pro Val Gly
TGGCAGTACCTCGTCAACAACAATTTGGGCGGCAATCTTGATTCCACGAG
                                                  950
Trp Gln Tyr Leu Val Asn Asn Asn Leu Gly Gly Asn Leu Asp Ser Thr Ser
CATTTCCAAGTATGATCAGCTTGTTCAGGGGTGCCTGTCTCTGGGCGCAT
                                                  1000
     Ile Ser Lys Tyr Asp Gln Leu Val Gln Gly Cys Leu Ser Leu Gly Ala
ACTGCATCGTCGACATCCACAATTATGCTCGATGGAACGGTGGGATCATT
                                                  1050
Tyr Cys Ile Val Asp Ile His Asn Tyr Ala Arg Trp Asn Gly Gly Ile Ile
GGTCAGGGCGGCCCTACTAATGCTCAATTCACGAGCCTTTGGTCGCAGTT
                                                  1100
Gly Gln Gly Gly Pro Thr Asn Ala Gln Phe Thr Ser Leu Trp Ser Gln Leu
GGCATCAAAGTACGCATCTCAGTCGAGGGTGTGGTTCGGCATCATGAATG
                                                  1150
     Ala Ser Lys Tyr Ala Ser Gln Ser Arg Val Trp Phe Gly Ile Met Asn
AGCCCCACGACGTGAACATCAACACCTGGGCTGCCACGGTCCAAGAGGTT
                                                  1200
Glu Pro His Asp Val Asn Ile Asn Thr Trp Ala Ala Thr Val Gln Glu Val
GTAACCGCAATCCGCAACGCTGGTGCTACGTCGCAATTCATCTCTTTGCC
                                                  1250
Val Thr Ala Ile Arg Asn Ala Gly Ala Thr Ser Gln Phe Ile Ser Leu Pro
TGGAAATGATTGGCAATCTGCTGGGGCTTTCATATCCGATGGCAGTGCAG
                                                  1300
  Gly Asn Asp Trp Gln Ser Ala Gly Ala Phe Ile Ser Asp Gly Ser Ala
CCGCCCTGTCTCAAGTCACGAACCCGGATGGGTCAACAACGAATCTGATT
                                                  1350
Ala Ala Leu Ser Gln Val Thr Asn Pro Asp Gly Ser Thr Thr Asn Leu Ile
TTTGACGTGCACAAATACTTGGACTCAGACAACTCCGGTACTCACGCCGA
                                                  1400
Phe Asp Val His Lys Tyr Leu Asp Ser Asp Asn Ser Gly Thr His Ala Glu
ATGTACTACAAATAACATTGACGGCGCCTTTTCTCCGCTTGCCACTTGGC
                                                  1450
 Cys Thr Thr Asn Asn Ile Asp Gly Ala Phe Ser Pro Leu Ala Thr Trp
TCCGACAGAACAATCGCCAGGCTATCCTGACAGAAACCGGTGGTGGCAAC
                                                  1500
Leu Arg Gln Asn Asn Arg Gln Ala Ile Leu Thr Glu Thr Gly Gly Gly Asn
GTTCAGTCCTGCATACAAGACATGTGCCAGCAAATCCAATATCTCAACCA
                                                  1550
Val Gln Ser Cys Ile Gln Asp Met Cys Gln Gln Ile Gln Tyr Leu Asn Gln
GAACTCAGATGTCTATCTTGGCTATGTTGGTTGGGGTGCCGGATCATTTG
                                                  1600
Asn Ser Asp Val Tyr Leu Gly Tyr Val Gly Trp Gly Ala Gly Ser Phe
```

FIG._4B

```
ACATGTCTTGAGGCTTGGCAAATACGGCGATATTGGGCCGATTGGGTCCT
                                                   650
             Leu Gly Lys Tyr Gly Asp Ile Gly Pro Ile Gly Ser

CACAGGGAACAGTCAACGTCGGTGGCCAGAGCTGGACGCTCTACTATGGC
                                                   700
Ser Gln Gly Thr Val Asn Val Gly Gly Gln Ser Trp Thr Leu Tyr Tyr Gly

TACAACGGAGCCATGCAAGTCTATTCCTTTGTGGCCCAGACCAACACTAC
                                                   750
Tyr Asn Gly Ala Met Gln Val Tyr Ser Phe Val Ala Gln Thr Asn Thr Thr

CAACTACAGCGGAGATGTCAAGAACTTCTTCAATTATCTCCGAGACAATA
                                                   800
Asn Tyr Ser Gly Asp Val Lys Asn Phe Phe Asn Tyr Leu Arg Asp Asn

AAGGATACAACGCTGCAGGCCAATATGTTCTTAGTAAGTCACCCTCACTG
                                                   850
Lys Gly Tyr Asn Ala Ala Gly Gln Tyr Val Leu

TGACTGGGCTGAGTTTGTTGCAACGTTTGCTAACAAAACCTTCGTATAGG
                                                   900

CTACCAATTTGGTACCGAGCCCTTCACGGGCAGTGGAACTCTGAACGTCG
                                                   950
Ser Tyr Gln Phe Gly Thr Glu Pro Phe Thr Gly Ser Gly Thr Leu Asn Val

CATCCTGGACCGCATCTATCAACTAAAACCTGGAAACGTGAGATGTGGTG
                                                   1000
Ala Ser Trp Thr Ala Ser Ile Asn* * *

GGCATACGTTATTGAGCGAGGGAAAAAAAGCATTGGATCCATTGAAGATG
                                                   1050
```

```
GGGTGGTCTGGATGAAACGTCTTGGCCAAATCGTGATCGATTGATACTCG
|----|----|----|----|----|----|----|----|----|----| 50

CATCTATAAGATGGCACAGATCGACTCTTGATTCACAGACATCCGTCAGC
|----|----|----|----|----|----|----|----|----|----| 100

CCTCAAGCCGTTTGCAAGTCCACAAACACAAGCACAAGCATAGCGTCGCA
|----|----|----|----|----|----|----|----|----|----| 150

ATGAAGTTCCTTCAAGTCCTCCCTGCCCTCATACCGGCCGCCCTGGCCCA
|----|----|----|----|----|----|----|----|----|----| 200
Met Lys Phe Leu Gln Val Leu Pro Ala Leu Ile Pro Ala Ala Leu Ala Gln
                                                                ↑
AACCAGCTGTGACCAGTGGGCAACCTTCACTGGCAACGGCTACACAGTCA
|----|----|----|----|----|----|----|----|----|----| 250
Thr Ser Cys Asp Gln Trp Ala Thr Phe Thr Gly Asn Gly Tyr Thr Val

GCAACAACCTTTGGGGAGCATCAGCCGGCTCTGGATTTGGCTGCGTGACG
|----|----|----|----|----|----|----|----|----|----| 300
Ser Asn Asn Leu Trp Gly Ala Ser Ala Gly Ser Gly Phe Gly Cys Val Thr

GCGGTATCGCTCAGCGGCGGGGCCTCCTGGCACGCAGACTGGCAGTGGTC
|----|----|----|----|----|----|----|----|----|----| 350
Ala Val Ser Leu Ser Gly Gly Ala Ser Trp His Ala Asp Trp Gln Trp Ser

CGGCGGCCAGAACAACGTCAAGTCGTACCAGAACTCTCAGATTGCCATTC
|----|----|----|----|----|----|----|----|----|----| 400
Gly Gly Gln Asn Asn Val Lys Ser Tyr Gln Asn Ser Gln Ile Ala Ile

CCCAGAAGAGGACCGTCAACAGCATCAGCAGCATGCCCACCACTGCCAGC
|----|----|----|----|----|----|----|----|----|----| 450
Pro Gln Lys Arg Thr Val Asn Ser Ile Ser Ser Met Pro Thr Thr Ala Ser

TGGAGCTACAGCGGGAGCAACATCCGCGCTAATGTTGCGTATGACTTGTT
|----|----|----|----|----|----|----|----|----|----| 500
Trp Ser Tyr Ser Gly Ser Asn Ile Arg Ala Asn Val Ala Tyr Asp Leu Phe

CACCGCAGCCAACCCGAATCATGTCACGTACTCGGGAGACTACGAACTCA
|----|----|----|----|----|----|----|----|----|----| 550
Thr Ala Ala Asn Pro Asn His Val Thr Tyr Ser Gly Asp Tyr Glu Leu

TGATCTGGTAAGCCATAAGAAGTGACCCTCCTTGATAGTTTCGACTAACA
|----|----|----|----|----|----|----|----|----|----| 600
Met Ile Trp
```

| FIG._6A |
|---|
| FIG._6B |

FIG._6A

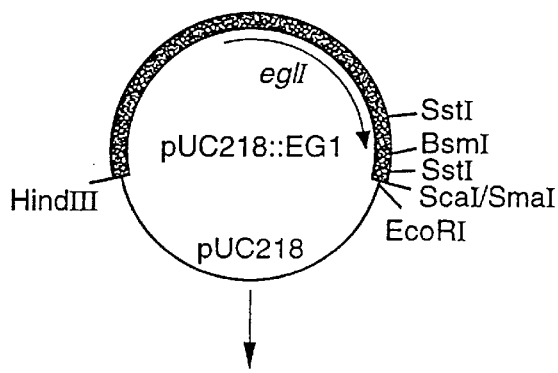

- Digest with BsmI and EcoRI
- Isolate 300bp BsmI/EcoRI Fragment
- Digest pUC218 with SstI and EcoRI
- Ligate pUC218 SstI/EcoRI and BsmI/EcoRI fragment with the following synthetic oligonucleotides  (SEQ. ID NO:37)

```
    CGTAGAGCGTTGACTTGCCTGTGGTCTGTCCAGACGGGGGACGATAGAATGCG
    TCGAGCATCTCGCAACTGAACGGACACCAGACAGGTCTGCCCCCTGCTATCTTAC
SstI                                                      BsmI
```

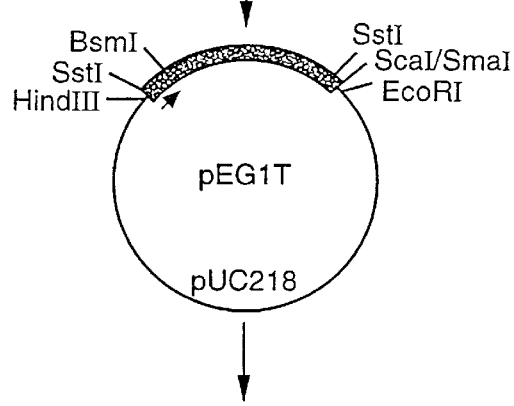

Digest pEG1T with HindIII and BsmI and Isolate vector fragment
Digest pUC218::EG1 with HindIII and SstI and Isolate 2.3 kb EG1 fragment
Ligate pEG1T HindIII/BsmI and 2.3 Kb HindIII/SstI with the following synthetic oligonucleotides (SEQ. ID NO:37)

```
    CGTAGAGCGTTGACTTGCCTGTGGTCTGTCCAGACGGGGGACGATAGAATGCG
    TCGAGCATCTCGCAACTGAACGGACACCAGACAGGTCTGCCCCCTGCTATCTTAC
SstI                                                      BsmI
```

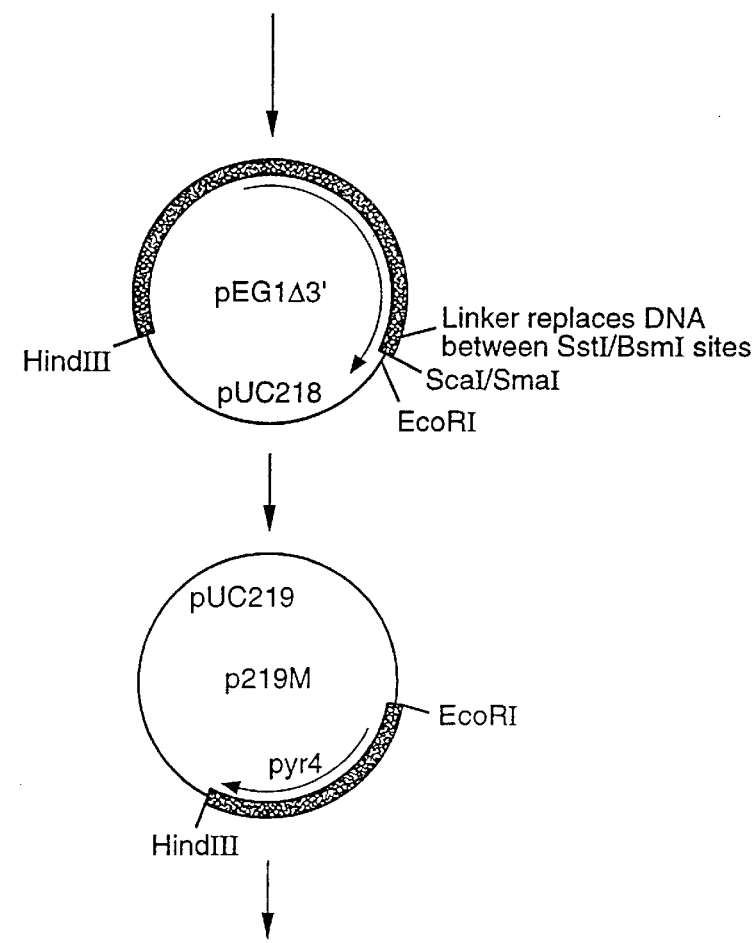
- Digest p219M with EcoRI and HindIII
- Isolate 1.6Kb EcoRI/HindIII *pyr4* gene fragment
- Digest pUC18 with EcoRI SstI and dephosphorylate the ends with calf alkaline phosphotase
- Isolate the HindIII/EcoRI EG1 fragment from pEG1Δ3'
- Ligate together pUC18 EcoRI, EcoRI/HindIII *pyr4* gene fragment and HindIII/EcoRI EG1 fragment
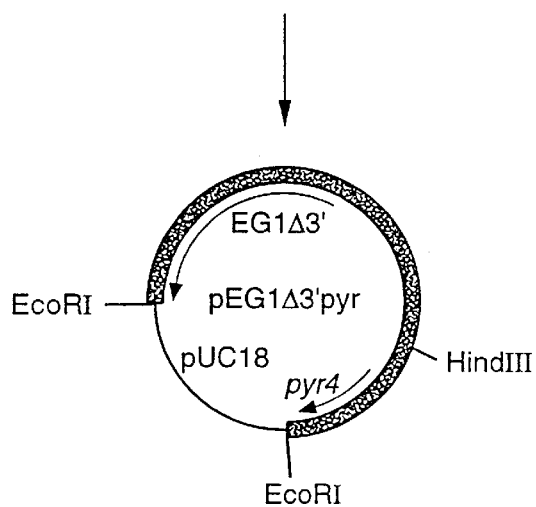
FIG._6B

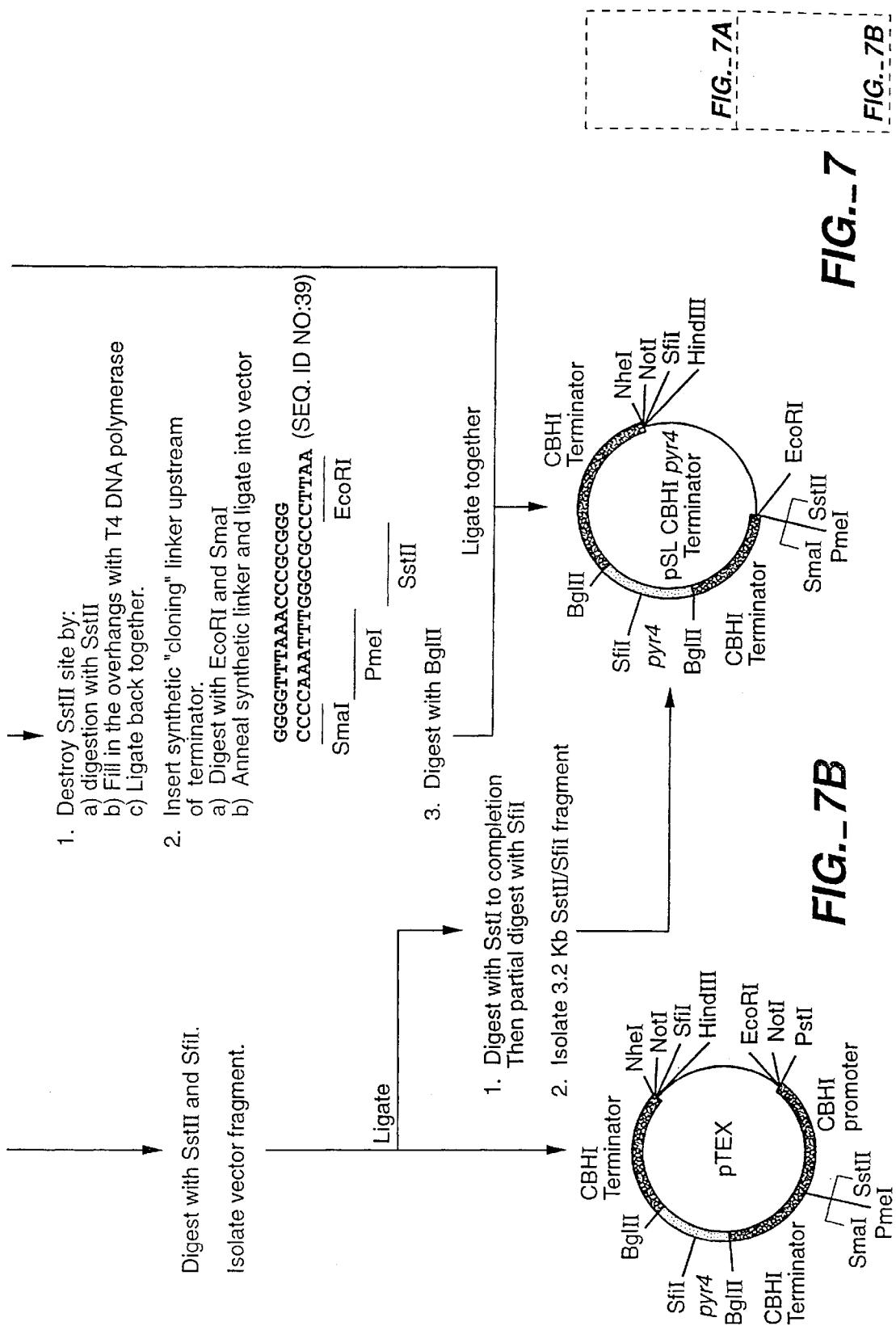

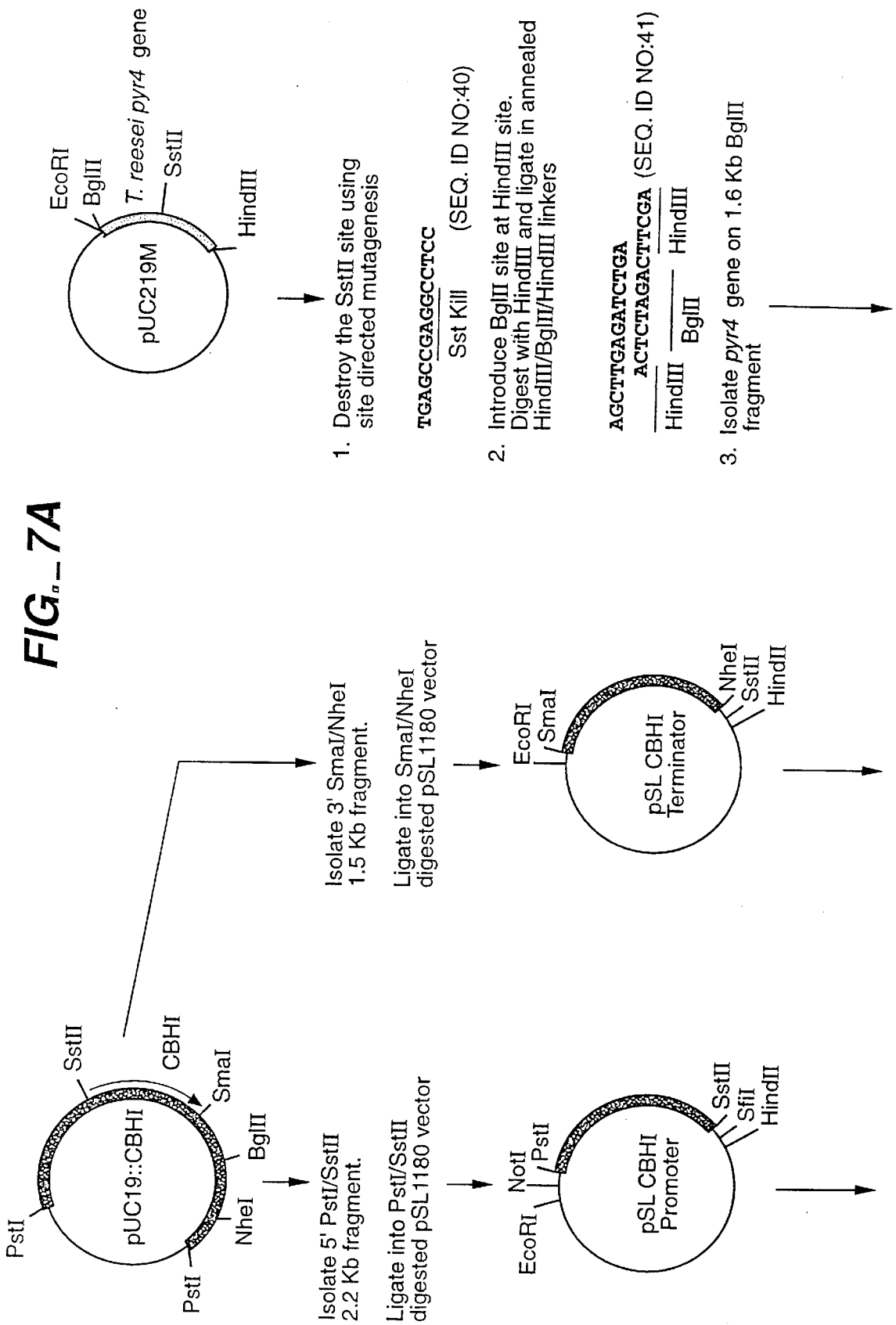
FIG._7A

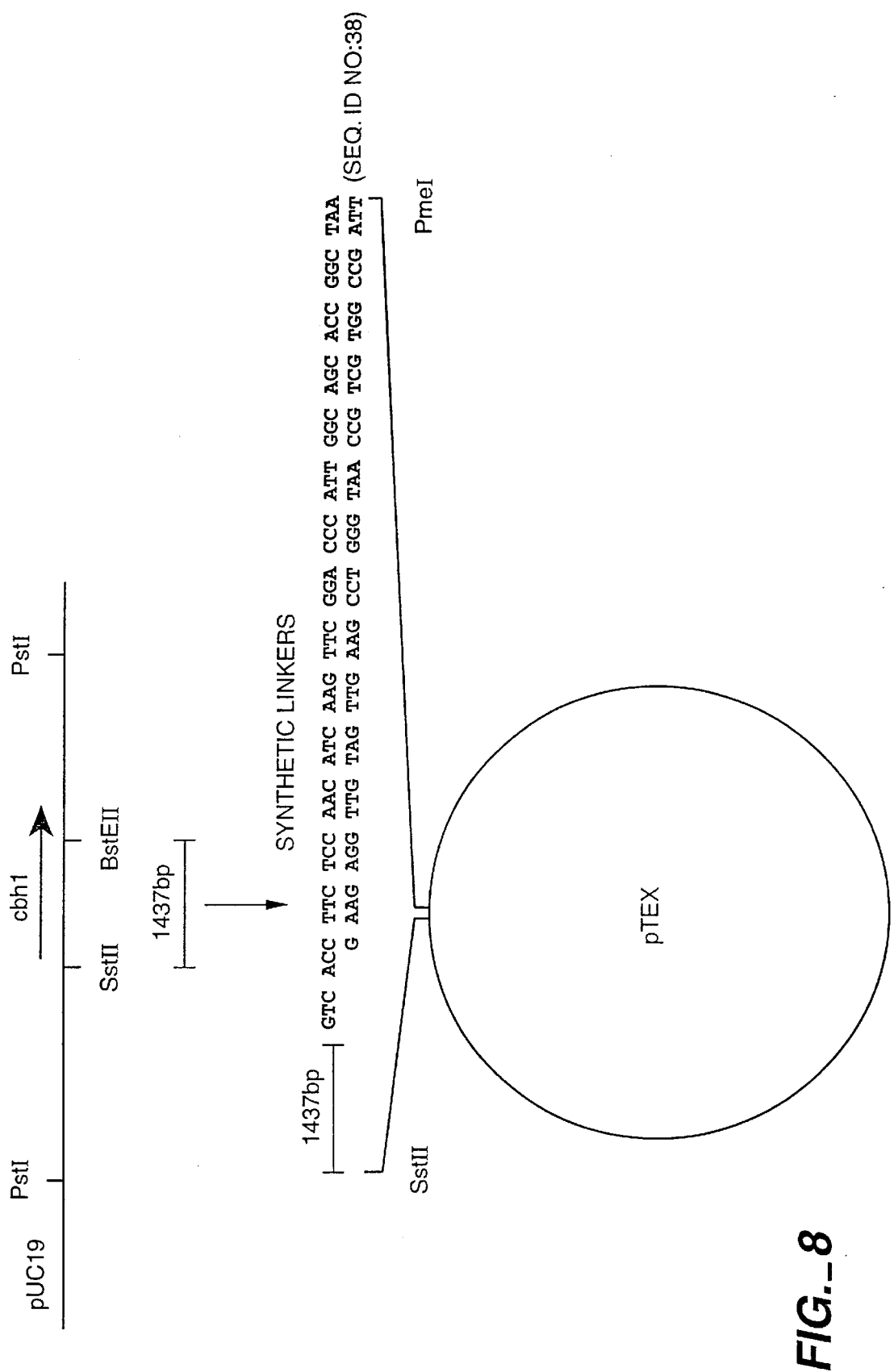
FIG._8

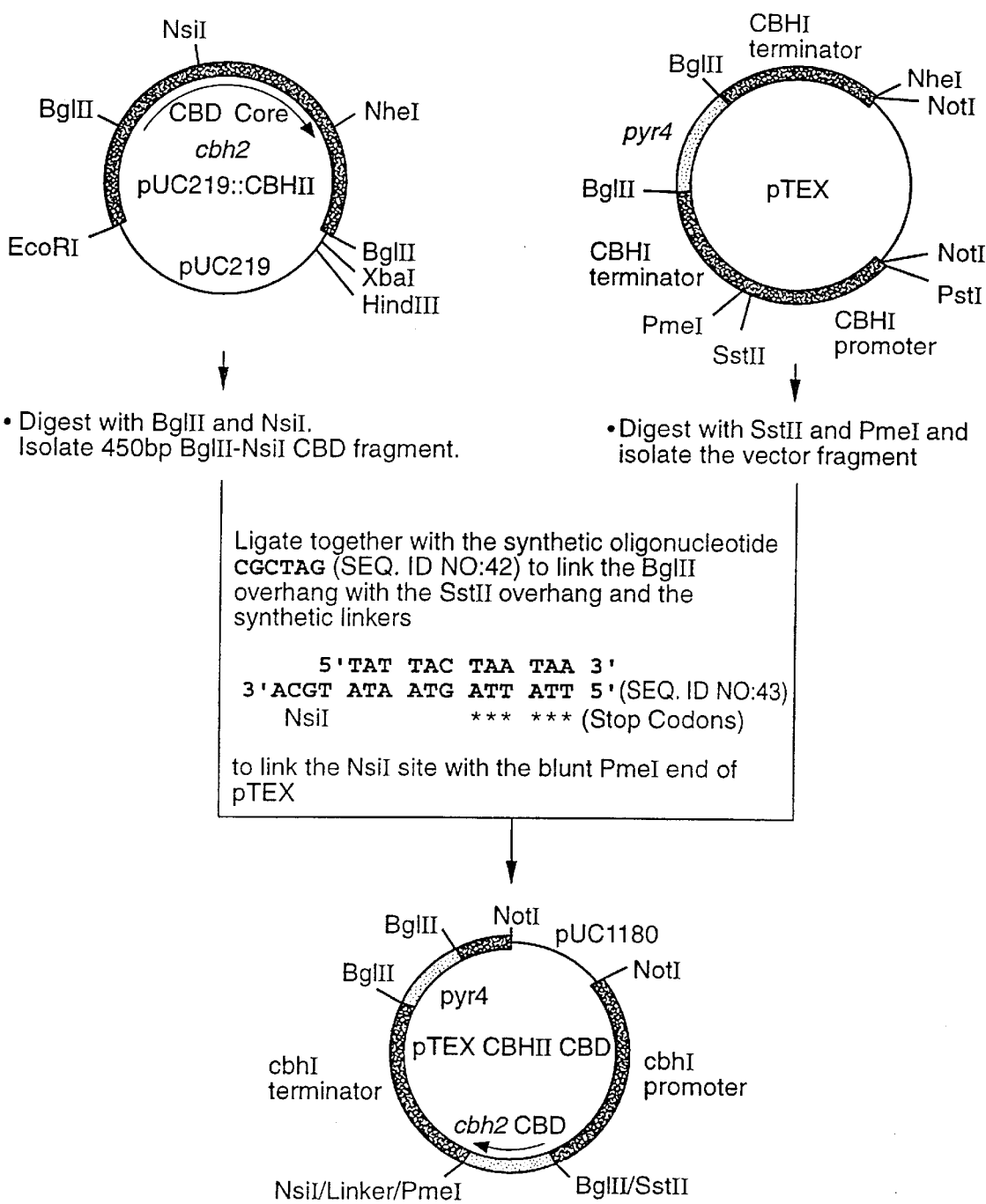
FIG._9

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..93

( x i ) SEQUENCE DESCRIPTION: SEQ ID NO:1:

```
GGC  CAG  TGC  GGC  GGT  ATT  GGC  TAC  AGC  GGC  CCC  ACG  GTC  TGC  GCC  AGC        48
Gly  Gln  Cys  Gly  Gly  Ile  Gly  Tyr  Ser  Gly  Pro  Thr  Val  Cys  Ala  Ser
 1                    5                        10                        15

GGC  ACA  ACT  TGC  CAG  GTC  CTG  AAC  CCT  TAC  TAC  TCT  CAG  TGC  CTG             93
Gly  Thr  Thr  Cys  Gln  Val  Leu  Asn  Pro  Tyr  Tyr  Ser  Gln  Cys  Leu
                 20                        25                        30
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gly  Gln  Cys  Gly  Gly  Ile  Gly  Tyr  Ser  Gly  Pro  Thr  Val  Cys  Ala  Ser
 1                    5                        10                        15

Gly  Thr  Thr  Cys  Gln  Val  Leu  Asn  Pro  Tyr  Tyr  Ser  Gln  Cys  Leu
                 20                        25                        30
```

( 2 ) INFORMATION FOR SEQ ID NO:3:

( i ) SEQUENCE CHARACTERISTICS:
        ( A ) LENGTH: 166 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(1..20, 70..166)

( x i ) SEQUENCE DESCRIPTION: SEQ ID NO:3:

```
CAA GCT TGC TCA AGC GTC    TG   GTAATTATGT GAACCCTCTC AAGAGACCCA          50
Gln Ala Cys Ser Ser Val   Trp
 1               5
```

```
AATACTGAGA TATGTCAAG G GGC CAA TGT GGT GGC CAG AAT TGG TCG GGT           100
                       Gly Gln Cys Gly Gly Gln Asn Trp Ser Gly
                                    10                  15
```

```
CCG ACT TGC TGT GCT TCC GGA AGC ACA TGC GTC TAC TCC AAC GAC TAT         148
Pro Thr Cys Cys Ala Ser Gly Ser Thr Cys Val Tyr Ser Asn Asp Tyr
            20              25                  30
```

```
TAC TCC CAG TGT CTT CCC                                                  166
Tyr Ser Gln Cys Leu Pro
        35
```

( 2 ) INFORMATION FOR SEQ ID NO:4:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Gln Ala Cys Ser Ser Val Trp Gly Gln Cys Gly Gly Gln Asn Trp Ser
 1               5                  10                  15

Gly Pro Thr Cys Cys Ala Ser Gly Ser Thr Cys Val Tyr Ser Asn Asp
                20                  25                  30

Tyr Tyr Ser Gln Cys Leu Pro
                35
```

( 2 ) INFORMATION FOR SEQ ID NO:5:

( i ) SEQUENCE CHARACTERISTICS:
        ( A ) LENGTH: 156 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(1..82, 140..156)

( x i ) SEQUENCE DESCRIPTION: SEQ ID NO:5:

```
CAC TGG GGG CAG TGC GGT GGC ATT GGG TAC AGC GGG TGC AAG ACG TGC          48
His Trp Gly Gln Cys Gly Gly Ile Gly Tyr Ser Gly Cys Lys Thr Cys
 1               5                  10                  15
```

```
ACG TCG GGC ACT ACG TGC CAG TAT AGC AAC GAC   T GTTCGTATCC                92
Thr Ser Gly Thr Thr Cys Gln Tyr Ser Asn Asp
            20                  25
```

```
CCATGCCTGA CGGGAGTGAT TTTGAGATGC TAACCGCTAA AATACAG   AC TAC TCG         147
                                                     Tyr Tyr Ser
                                                              30
```

```
CAA TGC CTT                                                              156
Gln Cys Leu
```

( 2 ) INFORMATION FOR SEQ ID NO:6:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| His | Trp | Gly | Gln | Cys | Gly | Gly | Ile | Gly | Tyr | Ser | Gly | Cys | Lys | Thr | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Ser | Gly | Thr | Thr | Cys | Gln | Tyr | Ser | Asn | Asp | Tyr | Tyr | Ser | Gln | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Leu ( 2 ) INFORMATION FOR SEQ ID NO:7:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..108

( x i ) SEQUENCE DESCRIPTION: SEQ ID NO:7:

| CAG | CAG | ACT | GTC | TGG | GGC | CAG | TGT | GGA | GGT | ATT | GGT | TGG | AGC | GGA | CCT | 48 |
|-----|-----|-----|-----|-----|-----|-----|-----|-----|-----|-----|-----|-----|-----|-----|-----|----|
| Gln | Gln | Thr | Val | Trp | Gly | Gln | Cys | Gly | Gly | Ile | Gly | Trp | Ser | Gly | Pro |   |
| 1   |     |     |     | 5   |     |     |     |     | 10  |     |     |     |     | 15  |     |   |

| ACG | AAT | TGT | GCT | CCT | GGC | TCA | GCT | TGT | TCG | ACC | CTC | AAT | CCT | TAT | TAT | 96 |
|-----|-----|-----|-----|-----|-----|-----|-----|-----|-----|-----|-----|-----|-----|-----|-----|----|
| Thr | Asn | Cys | Ala | Pro | Gly | Ser | Ala | Cys | Ser | Thr | Leu | Asn | Pro | Tyr | Tyr |    |
|     |     |     | 20  |     |     |     |     | 25  |     |     |     |     | 30  |     |     |    |

| GCG | CAA | TGT | ATT | 108 |
|-----|-----|-----|-----|-----|
| Ala | Gln | Cys | Ile |     |
|     |     | 35  |     |     |

( 2 ) INFORMATION FOR SEQ ID NO:8:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Gln | Gln | Thr | Val | Trp | Gly | Gln | Cys | Gly | Gly | Ile | Gly | Trp | Ser | Gly | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Asn | Cys | Ala | Pro | Gly | Ser | Ala | Cys | Ser | Thr | Leu | Asn | Pro | Tyr | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Gln | Cys | Ile |
|-----|-----|-----|-----|
|     |     | 35  |     |

( 2 ) INFORMATION FOR SEQ ID NO:9:

( i ) SEQUENCE CHARACTERISTICS:
        ( A ) LENGTH: 1453 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(1..410, 478..1174, 1238..1453)

( x i ) SEQUENCE DESCRIPTION: SEQ ID NO:9:

| CAG | TCG | GCC | TGC | ACT | CTC | CAA | TCG | GAG | ACT | CAC | CCG | CCT | CTG | ACA | TGG | 48 |
|-----|-----|-----|-----|-----|-----|-----|-----|-----|-----|-----|-----|-----|-----|-----|-----|----|
| Gln | Ser | Ala | Cys | Thr | Leu | Gln | Ser | Glu | Thr | His | Pro | Pro | Leu | Thr | Trp |    |

```
                1                           5                                          10                                        15
CAG   AAA   TGC   TCG   TCT   GGT   GGC   ACT   TGC   ACT   CAA   CAG   ACA   GGC   TCC   GTG         96
Gln   Lys   Cys   Ser   Ser   Gly   Gly   Thr   Cys   Thr   Gln   Gln   Thr   Gly   Ser   Val
                  20                        25                              30

GTC   ATC   GAC   GCC   AAC   TGG   CGC   TGG   ACT   CAC   GCT   ACG   AAC   AGC   AGC   ACG        144
Val   Ile   Asp   Ala   Asn   Trp   Arg   Trp   Thr   His   Ala   Thr   Asn   Ser   Ser   Thr
            35                        40                              45

AAC   TGC   TAC   GAT   GGC   AAC   ACT   TGG   AGC   TCG   ACC   CTA   TGT   CCT   GAC   AAC        192
Asn   Cys   Tyr   Asp   Gly   Asn   Thr   Trp   Ser   Ser   Thr   Leu   Cys   Pro   Asp   Asn
            50                        55                              60

GAG   ACC   TGC   GCG   AAG   AAC   TGC   TGT   CTG   GAC   GGT   GCC   GCC   TAC   GCG   TCC        240
Glu   Thr   Cys   Ala   Lys   Asn   Cys   Cys   Leu   Asp   Gly   Ala   Ala   Tyr   Ala   Ser
65                      70                        75                              80

ACG   TAC   GGA   GTT   ACC   ACG   AGC   GGT   AAC   AGC   CTC   TCC   ATT   GGC   TTT   GTC        288
Thr   Tyr   Gly   Val   Thr   Thr   Ser   Gly   Asn   Ser   Leu   Ser   Ile   Gly   Phe   Val
                        85                        90                              95

ACC   CAG   TCT   GCG   CAG   AAG   AAC   GTT   GGC   GCT   CGC   CTT   TAC   CTT   ATG   GCG        336
Thr   Gln   Ser   Ala   Gln   Lys   Asn   Val   Gly   Ala   Arg   Leu   Tyr   Leu   Met   Ala
                  100                       105                             110

AGC   GAC   ACG   ACC   TAC   CAG   GAA   TTC   ACC   CTG   CTT   GGC   AAC   GAG   TTC   TCT        384
Ser   Asp   Thr   Thr   Tyr   Gln   Glu   Phe   Thr   Leu   Leu   Gly   Asn   Glu   Phe   Ser
            115                       120                             125

TTC   GAT   GTT   GAT   GTT   TCG   CAG   CTG      CC    GTAAGTGACT    TACCATGAAC                    430
Phe   Asp   Val   Asp   Val   Ser   Gln   Leu      Pro
130                                 135

CCCTGACGTA   TCTTCTTGTG   GGCTCCCAGC   TGACTGGCCA   ATTTAAG  G   TGC   GGC                           484
                                                                 Cys   Gly

TTG   AAC   GGA   GCT   CTC   TAC   TTC   GTG   TCC   ATG   GAC   GCG   GAT   GGT   GGC   GTG        532
Leu   Asn   Gly   Ala   Leu   Tyr   Phe   Val   Ser   Met   Asp   Ala   Asp   Gly   Gly   Val
140                       145                       150                             155

AGC   AAG   TAT   CCC   ACC   AAC   ACC   GCT   GGC   GCC   AAG   TAC   GGC   ACG   GGG   TAC  580
      Ser   Lys   Tyr   Pro   Thr   Asn   Thr   Ala   Gly   Ala   Lys   Tyr   Gly   Thr   Gly   Tyr
                        160                       165                             170

TGT   GAC   AGC   CAG   TGT   CCC   CGC   GAT   CTG   AAG   TTC   ATC   AAT   GGC   CAG   GCC        628
Cys   Asp   Ser   Gln   Cys   Pro   Arg   Asp   Leu   Lys   Phe   Ile   Asn   Gly   Gln   Ala
                  175                       180                             185

AAC   GTT   GAG   GGC   TGG   GAG   CCG   TCA   TCC   AAC   AAC   GCA   AAC   ACG   GGC   ATT        676
Asn   Val   Glu   Gly   Trp   Glu   Pro   Ser   Ser   Asn   Asn   Ala   Asn   Thr   Gly   Ile
            190                       195                             200

GGA   GGA   CAC   GGA   AGC   TGC   TGC   TCT   GAG   ATG   GAT   ATC   TGG   GAG   GCC   AAC        724
Gly   Gly   His   Gly   Ser   Cys   Cys   Ser   Glu   Met   Asp   Ile   Trp   Glu   Ala   Asn
      205                       210                             215

TCC   ATC   TCC   GAG   GCT   CTT   ACC   CCC   CAC   CCT   TGC   ACG   ACT   GTC   GGC   CAG        772
Ser   Ile   Ser   Glu   Ala   Leu   Thr   Pro   His   Pro   Cys   Thr   Thr   Val   Gly   Gln
220                       225                       230                             235

GAG   ATC   TGC   GAG   GGT   GAT   GGG   TGC   GGC   GGA   ACT   TAC   TCC   GAT   AAC   AGA        820
Glu   Ile   Cys   Glu   Gly   Asp   Gly   Cys   Gly   Gly   Thr   Tyr   Ser   Asp   Asn   Arg
                        240                       245                             250

TAT   GGC   GGC   ACT   TGC   GAT   CCC   GAT   GGC   TGC   GAC   TGG   AAC   CCA   TAC   CGC        868
Tyr   Gly   Gly   Thr   Cys   Asp   Pro   Asp   Gly   Cys   Asp   Trp   Asn   Pro   Tyr   Arg
                  255                       260                             265

CTG   GGC   AAC   ACC   AGC   TTC   TAC   GGC   CCT   GGC   TCA   AGC   TTT   ACC   CTC   GAT        916
Leu   Gly   Asn   Thr   Ser   Phe   Tyr   Gly   Pro   Gly   Ser   Ser   Phe   Thr   Leu   Asp
            270                       275                             280

ACC   ACC   AAG   AAA   TTG   ACC   GTT   GTC   ACC   CAG   TTC   GAG   ACG   TCG   GGT   GCC        964
Thr   Thr   Lys   Lys   Leu   Thr   Val   Val   Thr   Gln   Phe   Glu   Thr   Ser   Gly   Ala
            285                       290                             295

ATC   AAC   CGA   TAC   TAT   GTC   CAG   AAT   GGC   GTC   ACT   TTC   CAG   CAG   CCC   AAC       1012
Ile   Asn   Arg   Tyr   Tyr   Val   Gln   Asn   Gly   Val   Thr   Phe   Gln   Gln   Pro   Asn
300                       305                       310                             315
```

```
GCC  GAG  CTT  GGT  AGT  TAC  TCT  GGC  AAC  GAG  CTC  AAC  GAT  GAT  TAC  TGC      1060
Ala  Glu  Leu  Gly  Ser  Tyr  Ser  Gly  Asn  Glu  Leu  Asn  Asp  Asp  Tyr  Cys
                    320                      325                     330

ACA  GCT  GAG  GAG  GCA  GAA  TTC  GGC  GGA  TCC  TCT  TTC  TCA  GAC  AAG  GGC      1108
Thr  Ala  Glu  Glu  Ala  Glu  Phe  Gly  Gly  Ser  Ser  Phe  Ser  Asp  Lys  Gly
               335                      340                     345

GGC  CTG  ACT  CAG  TTC  AAG  AAG  GCT  ACC  TCT  GGC  GGC  ATG  GTT  CTG  GTC      1156
Gly  Leu  Thr  Gln  Phe  Lys  Lys  Ala  Thr  Ser  Gly  Gly  Met  Val  Leu  Val
          350                      355                     360

ATG  AGT  CTG  TGG  GAT  GAT  GTGAGTTTGA TGGACAAACA TGCGCGTTGA                       1204
Met  Ser  Leu  Trp  Asp  Asp
     365

CAAAGAGTCA AGCAGCTGAC TGAGATGTTA CAG  TAC  TAC  GCC  AAC  ATG  CTG  TGG              1258
                                     Tyr  Tyr  Ala  Asn  Met  Leu  Trp
                                                    370                375

CTG  GAC  TCC  ACC  TAC  CCG  ACA  AAC  GAG  ACC  TCC  TCC  ACA  CCC  GGT  GCC      1306
Leu  Asp  Ser  Thr  Tyr  Pro  Thr  Asn  Glu  Thr  Ser  Ser  Thr  Pro  Gly  Ala
               380                      385                     390

GTG  CGC  GGA  AGC  TGC  TCC  ACC  AGC  TCC  GGT  GTC  CCT  GCT  CAG  GTC  GAA      1354
Val  Arg  Gly  Ser  Cys  Ser  Thr  Ser  Ser  Gly  Val  Pro  Ala  Gln  Val  Glu
               395                      400                     405

TCT  CAG  TCT  CCC  AAC  GCC  AAG  GTC  ACC  TTC  TCC  AAC  ATC  AAG  TTC  GGA      1402
Ser  Gln  Ser  Pro  Asn  Ala  Lys  Val  Thr  Phe  Ser  Asn  Ile  Lys  Phe  Gly
          410                      415                     420

CCC  ATT  GGC  AGC  ACC  GGC  AAC  CCT  AGC  GGC  GGC  AAC  CCT  CCC  GGC  GGA      1450
Pro  Ile  Gly  Ser  Thr  Gly  Asn  Pro  Ser  Gly  Gly  Asn  Pro  Pro  Gly  Gly
425                      430                      435                     440

AAC                                                                                  1453
Asn
```

( 2 ) INFORMATION FOR SEQ ID NO:10:

( i ) SEQUENCE CHARACTERISTICS:
    ( A ) LENGTH: 441 amino acids
    ( B ) TYPE: amino acid
    ( D ) TOPOLOGY: linear ( i i ) MOLECULE TYPE: protein ( x i ) SEQUENCE DESCRIPTION: SEQ ID NO:10:

```
Gln  Ser  Ala  Cys  Thr  Leu  Gln  Ser  Glu  His  Pro  Pro  Leu  Thr  Trp
 1                  5                     10                          15

Gln  Lys  Cys  Ser  Ser  Gly  Gly  Thr  Cys  Thr  Gln  Gln  Thr  Gly  Ser  Val
                20                      25                      30

Val  Ile  Asp  Ala  Asn  Trp  Arg  Trp  Thr  His  Ala  Thr  Asn  Ser  Ser  Thr
                35                      40                      45

Asn  Cys  Tyr  Asp  Gly  Asn  Thr  Trp  Ser  Ser  Thr  Leu  Cys  Pro  Asp  Asn
          50                      55                      60

Glu  Thr  Cys  Ala  Lys  Asn  Cys  Cys  Leu  Asp  Gly  Ala  Ala  Tyr  Ala  Ser
 65                      70                      75                      80

Thr  Tyr  Gly  Val  Thr  Thr  Ser  Gly  Asn  Ser  Leu  Ser  Ile  Gly  Phe  Val
                    85                      90                      95

Thr  Gln  Ser  Ala  Gln  Lys  Asn  Val  Gly  Ala  Arg  Leu  Tyr  Leu  Met  Ala
               100                     105                     110

Ser  Asp  Thr  Thr  Tyr  Gln  Glu  Phe  Thr  Leu  Leu  Gly  Asn  Glu  Phe  Ser
          115                     120                     125

Phe  Asp  Val  Asp  Val  Ser  Gln  Leu  Pro  Cys  Gly  Leu  Asn  Gly  Ala  Leu
          130                     135                     140

Tyr  Phe  Val  Ser  Met  Asp  Ala  Asp  Gly  Gly  Val  Ser  Lys  Tyr  Pro  Thr
```

| 145 | | | | | 150 | | | | | 155 | | | | | 160 |
|---|---|---|---|---|---|---|---|---|---|---|---|---|---|---|---|
| Asn | Thr | Ala | Gly | Ala | Lys | Tyr | Gly | Thr | Tyr | Cys | Asp | Ser | Gln | Cys | |
| | | | | 165 | | | | | 170 | | | | 175 | | |

Pro Arg Asp Leu Lys Phe Ile Asn Gly Gln Ala Asn Val Glu Gly Trp
                180                    185                    190

Glu Pro Ser Ser Asn Asn Ala Asn Thr Gly Ile Gly Gly His Gly Ser
        195                    200                    205

Cys Cys Ser Glu Met Asp Ile Trp Glu Ala Asn Ser Ile Ser Glu Ala
    210                    215                    220

Leu Thr Pro His Pro Cys Thr Thr Val Gly Gln Glu Ile Cys Glu Gly
225                    230                    235                    240

Asp Gly Cys Gly Gly Thr Tyr Ser Asp Asn Arg Tyr Gly Gly Thr Cys
                245                    250                    255

Asp Pro Asp Gly Cys Asp Trp Asn Pro Tyr Arg Leu Gly Asn Thr Ser
                260                    265                    270

Phe Tyr Gly Pro Gly Ser Ser Phe Thr Leu Asp Thr Thr Lys Lys Leu
            275                    280                    285

Thr Val Val Thr Gln Phe Glu Thr Ser Gly Ala Ile Asn Arg Tyr Tyr
        290                    295                    300

Val Gln Asn Gly Val Thr Phe Gln Gln Pro Asn Ala Glu Leu Gly Ser
305                    310                    315                    320

Tyr Ser Gly Asn Glu Leu Asn Asp Asp Tyr Cys Thr Ala Glu Glu Ala
                325                    330                    335

Glu Phe Gly Gly Ser Ser Phe Ser Asp Lys Gly Gly Leu Thr Gln Phe
            340                    345                    350

Lys Lys Ala Thr Ser Gly Gly Met Val Leu Val Met Ser Leu Trp Asp
            355                    360                    365

Asp Tyr Tyr Ala Asn Met Leu Trp Leu Asp Ser Thr Tyr Pro Thr Asn
        370                    375                    380

Glu Thr Ser Ser Thr Pro Gly Ala Val Arg Gly Ser Cys Ser Thr Ser
385                    390                    395                    400

Ser Gly Val Pro Ala Gln Val Glu Ser Gln Ser Pro Asn Ala Lys Val
                405                    410                    415

Thr Phe Ser Asn Ile Lys Phe Gly Pro Ile Gly Ser Thr Gly Asn Pro
            420                    425                    430

Ser Gly Gly Asn Pro Pro Gly Gly Asn
            435                    440

(2) INFORMATION FOR SEQ ID NO:11:

(i) SEQUENCE CHARACTERISTICS:
        (A) LENGTH: 1241 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..161, 218..465, 556..1241)

(xi) SEQUENCE DESCRIPTION: SEQ ID NO:11:

TCG GGA ACC GCT ACG TAT TCA GGC AAC CCT TTT GTT GGG GTC ACT CCT       48
Ser Gly Thr Ala Thr Tyr Ser Gly Asn Pro Phe Val Gly Val Thr Pro
 1               5                  10                  15

TGG GCC AAT GCA TAT TAC GCC TCT GAA GTT AGC AGC CTC GCT ATT CCT       96
Trp Ala Asn Ala Tyr Tyr Ala Ser Glu Val Ser Ser Leu Ala Ile Pro
            20                  25                  30

| | | | | | | | | | | | | | | | | |
|---|---|---|---|---|---|---|---|---|---|---|---|---|---|---|---|---|
| AGC | TTG | ACT | GGA | GCC | ATG | GCC | ACT | GCT | GCA | GCA | GCT | GTC | GCA | AAG | GTT | 144 |
| Ser | Leu | Thr | Gly | Ala | Met | Ala | Thr | Ala | Ala | Ala | Ala | Val | Ala | Lys | Val | |
| | | 35 | | | | 40 | | | | 45 | | | | | | |

| | | | | | | | | | |
|---|---|---|---|---|---|---|---|---|---|
| CCC | TCT | TTT | ATG | TGG | CT | GTAGGTCCTC | CCGGAACCAA | GGCAATCTGT | 191 |
| Pro | Ser | Phe | Met | Trp | Leu | | | | |
| | 50 | | | | | | | | |

| | | | | | | | | |
|---|---|---|---|---|---|---|---|---|
| TACTGAAGGC | TCATCATTCA | CTGCAG | A | GAT | ACT | CTT | GAC | AAG | ACC | CCT | CTC | 242 |

```
AGC TTG ACT GGA GCC ATG GCC ACT GCT GCA GCA GCT GTC GCA AAG GTT         144
Ser Leu Thr Gly Ala Met Ala Thr Ala Ala Ala Ala Val Ala Lys Val
         35                  40                  45

CCC TCT TTT ATG TGG  CT  GTAGGTCCTC CCGGAACCAA GGCAATCTGT               191
Pro Ser Phe Met Trp Leu
    50

TACTGAAGGC TCATCATTCA CTGCAG A GAT ACT CTT GAC AAG ACC CCT CTC          242
                               Asp Thr Leu Asp Lys Thr Pro Leu
                                55                  60

ATG GAG CAA ACC TTG GCC GAC ATC CGC ACC GCC AAC AAG AAT GGC GGT         290
Met Glu Gln Thr Leu Ala Asp Ile Arg Thr Ala Asn Lys Asn Gly Gly
         65                  70                  75

AAC TAT GCC GGA CAG TTT GTG GTG ATA GAC TTG CCG GAT CGC GAT TGC         338
Asn Tyr Ala Gly Gln Phe Val Val Ile Asp Leu Pro Asp Arg Asp Cys
         80                  85                  90

GCT GCC CTT GCC TCG AAT GGC GAA TAC TCT ATT GCC GAT GGT GGC GTC         386
Ala Ala Leu Ala Ser Asn Gly Glu Tyr Ser Ile Ala Asp Gly Gly Val
 95                 100                 105                 110

GCC AAA TAT AAG AAC TAT ATC GAC ACC ATT CGT CAA ATT GTC GTG GAA         434
Ala Lys Tyr Lys Asn Tyr Ile Asp Thr Ile Arg Gln Ile Val Val Glu
                115                 120                 125

TAT TCC GAT ATC CGG ACC CTC CTG GTT ATT  G GTATGAGTTT AAACACCTGC        485
Tyr Ser Asp Ile Arg Thr Leu Leu Val Ile
                130                 135

CTCCCCCCCC CCTTCCCTTC CTTTCCCGCC GGCATCTTGT CGTTGTGCTA ACTATTGTTC       545

CCTCTTCCAG  AG CCT GAC TCT CTT GCC AAC CTG GTG ACC AAC CTC GGT         593
               Glu Pro Asp Ser Leu Ala Asn Leu Val Thr Asn Leu Gly
                                140                 145

ACT CCA AAG TGT GCC AAT GCT CAG TCA GCC TAC CTT GAG TGC ATC AAC         641
Thr Pro Lys Cys Ala Asn Ala Gln Ser Ala Tyr Leu Glu Cys Ile Asn
150                 155                 160                 165

TAC GCC GTC ACA CAG CTG AAC CTT CCA AAT GTT GCG ATG TAT TTG GAC         689
Tyr Ala Val Thr Gln Leu Asn Leu Pro Asn Val Ala Met Tyr Leu Asp
                170                 175                 180

GCT GGC CAT GCA GGA TGG CTT GGC TGG CCG GCA AAC CAA GAC CCG GCC         737
Ala Gly His Ala Gly Trp Leu Gly Trp Pro Ala Asn Gln Asp Pro Ala
                185                 190                 195

GCT CAG CTA TTT GCA AAT GTT TAC AAG AAT GCA TCG TCT CCG AGA GCT         785
Ala Gln Leu Phe Ala Asn Val Tyr Lys Asn Ala Ser Ser Pro Arg Ala
        200                 205                 210

CTT CGC GGA TTG GCA ACC AAT GTC GCC AAC TAC AAC GGG TGG AAC ATT         833
Leu Arg Gly Leu Ala Thr Asn Val Ala Asn Tyr Asn Gly Trp Asn Ile
215                 220                 225

ACC AGC CCC CCA TCG TAC ACG CAA GGC AAC GCT GTC TAC AAC GAG AAG         881
Thr Ser Pro Pro Ser Tyr Thr Gln Gly Asn Ala Val Tyr Asn Glu Lys
230                 235                 240                 245

CTG TAC ATC CAC GCT ATT GGA CCT CTT CTT GCC AAT CAC GGC TGG TCC         929
Leu Tyr Ile His Ala Ile Gly Pro Leu Leu Ala Asn His Gly Trp Ser
                250                 255                 260

AAC GCC TTC TTC ATC ACT GAT CAA GGT CGA TCG GGA AAG CAG CCT ACC         977
Asn Ala Phe Phe Ile Thr Asp Gln Gly Arg Ser Gly Lys Gln Pro Thr
                265                 270                 275

GGA CAG CAA CAG TGG GGA GAC TGG TGC AAT GTG ATC GGC ACC GGA TTT        1025
Gly Gln Gln Gln Trp Gly Asp Trp Cys Asn Val Ile Gly Thr Gly Phe
                280                 285                 290

GGT ATT CGC CCA TCC GCA AAC ACT GGG GAC TCG TTG CTG GAT TCG TTT        1073
Gly Ile Arg Pro Ser Ala Asn Thr Gly Asp Ser Leu Leu Asp Ser Phe
295                 300                 305

GTC TGG GTC AAG CCA GGC GGC GAG TGT GAC GGC ACC AGC GAC AGC AGT        1121
```

-continued

| | | | | | | | | | | | | | | | |
|---|---|---|---|---|---|---|---|---|---|---|---|---|---|---|---|
| Val | Trp | Val | Lys | Pro | Gly | Gly | Glu | Cys | Asp | Gly | Thr | Ser | Asp | Ser | Ser |
| 310 | | | | 315 | | | | 320 | | | | | 325 | | |

| GCG | CCA | CGA | TTT | GAC | TCC | CAC | TGT | GCG | CTC | CCA | GAT | GCC | TTG | CAA | CCG | 1169 |
|---|---|---|---|---|---|---|---|---|---|---|---|---|---|---|---|---|
| Ala | Pro | Arg | Phe | Asp | Ser | His | Cys | Ala | Leu | Pro | Asp | Ala | Leu | Gln | Pro | |
| | | | | 330 | | | | 335 | | | | | 340 | | | |

| GCG | CCT | CAA | GCT | GGT | GCT | TGG | TTC | CAA | GCC | TAC | TTT | GTG | CAG | CTT | CTC | 1217 |
|---|---|---|---|---|---|---|---|---|---|---|---|---|---|---|---|---|
| Ala | Pro | Gln | Ala | Gly | Ala | Trp | Phe | Gln | Ala | Tyr | Phe | Val | Gln | Leu | Leu | |
| | | | 345 | | | | | 350 | | | | | 355 | | | |

| ACA | AAC | GCA | AAC | CCA | TCG | TTC | CTG | 1241 |
|---|---|---|---|---|---|---|---|---|
| Thr | Asn | Ala | Asn | Pro | Ser | Phe | Leu | |
| | | 360 | | | | | 365 | |

( 2 ) INFORMATION FOR SEQ ID NO:12:

( i ) SEQUENCE CHARACTERISTICS:
        ( A ) LENGTH: 365 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Ser | Gly | Thr | Ala | Thr | Tyr | Ser | Gly | Asn | Pro | Phe | Val | Gly | Val | Thr | Pro |
|---|---|---|---|---|---|---|---|---|---|---|---|---|---|---|---|
| 1 | | | | 5 | | | | | 10 | | | | | 15 | |

| Trp | Ala | Asn | Ala | Tyr | Tyr | Ala | Ser | Glu | Val | Ser | Ser | Leu | Ala | Ile | Pro |
|---|---|---|---|---|---|---|---|---|---|---|---|---|---|---|---|
| | | | 20 | | | | | 25 | | | | | 30 | | |

| Ser | Leu | Thr | Gly | Ala | Met | Ala | Thr | Ala | Ala | Ala | Val | Ala | Lys | Val |
|---|---|---|---|---|---|---|---|---|---|---|---|---|---|---|
| | | 35 | | | | 40 | | | | | 45 | | | |

| Pro | Ser | Phe | Met | Trp | Leu | Asp | Thr | Leu | Asp | Lys | Thr | Pro | Leu | Met | Glu |
|---|---|---|---|---|---|---|---|---|---|---|---|---|---|---|---|
| | 50 | | | | | 55 | | | | 60 | | | | | |

| Gln | Thr | Leu | Ala | Asp | Ile | Arg | Thr | Ala | Asn | Lys | Asn | Gly | Gly | Asn | Tyr |
|---|---|---|---|---|---|---|---|---|---|---|---|---|---|---|---|
| 65 | | | | | 70 | | | | | 75 | | | | | 80 |

| Ala | Gly | Gln | Phe | Val | Val | Ile | Asp | Leu | Pro | Asp | Arg | Asp | Cys | Ala | Ala |
|---|---|---|---|---|---|---|---|---|---|---|---|---|---|---|---|
| | | | | 85 | | | | | 90 | | | | | 95 | |

| Leu | Ala | Ser | Asn | Gly | Glu | Tyr | Ser | Ile | Ala | Asp | Gly | Gly | Val | Ala | Lys |
|---|---|---|---|---|---|---|---|---|---|---|---|---|---|---|---|
| | | | 100 | | | | 105 | | | | | 110 | | | |

| Tyr | Lys | Asn | Tyr | Ile | Asp | Thr | Ile | Arg | Gln | Ile | Val | Val | Glu | Tyr | Ser |
|---|---|---|---|---|---|---|---|---|---|---|---|---|---|---|---|
| | | 115 | | | | | 120 | | | | | 125 | | | |

| Asp | Ile | Arg | Thr | Leu | Leu | Val | Ile | Glu | Pro | Asp | Ser | Leu | Ala | Asn | Leu |
|---|---|---|---|---|---|---|---|---|---|---|---|---|---|---|---|
| | 130 | | | | | 135 | | | | | 140 | | | | |

| Val | Thr | Asn | Leu | Gly | Thr | Pro | Lys | Cys | Ala | Asn | Ala | Gln | Ser | Ala | Tyr |
|---|---|---|---|---|---|---|---|---|---|---|---|---|---|---|---|
| 145 | | | | | 150 | | | | | 155 | | | | | 160 |

| Leu | Glu | Cys | Ile | Asn | Tyr | Ala | Val | Thr | Gln | Leu | Asn | Leu | Pro | Asn | Val |
|---|---|---|---|---|---|---|---|---|---|---|---|---|---|---|---|
| | | | | 165 | | | | | 170 | | | | | 175 | |

| Ala | Met | Tyr | Leu | Asp | Ala | Gly | His | Ala | Gly | Trp | Leu | Gly | Trp | Pro | Ala |
|---|---|---|---|---|---|---|---|---|---|---|---|---|---|---|---|
| | | | 180 | | | | | 185 | | | | | 190 | | |

| Asn | Gln | Asp | Pro | Ala | Ala | Gln | Leu | Phe | Ala | Asn | Val | Tyr | Lys | Asn | Ala |
|---|---|---|---|---|---|---|---|---|---|---|---|---|---|---|---|
| | | 195 | | | | | 200 | | | | | 205 | | | |

| Ser | Ser | Pro | Arg | Ala | Leu | Arg | Gly | Leu | Ala | Thr | Asn | Val | Ala | Asn | Tyr |
|---|---|---|---|---|---|---|---|---|---|---|---|---|---|---|---|
| | 210 | | | | | 215 | | | | | 220 | | | | |

| Asn | Gly | Trp | Asn | Ile | Thr | Ser | Pro | Pro | Ser | Tyr | Thr | Gln | Gly | Asn | Ala |
|---|---|---|---|---|---|---|---|---|---|---|---|---|---|---|---|
| 225 | | | | | 230 | | | | | 235 | | | | | 240 |

| Val | Tyr | Asn | Glu | Lys | Leu | Tyr | Ile | His | Ala | Ile | Gly | Pro | Leu | Leu | Ala |
|---|---|---|---|---|---|---|---|---|---|---|---|---|---|---|---|
| | | | | 245 | | | | | 250 | | | | | 255 | |

| Asn | His | Gly | Trp | Ser | Asn | Ala | Phe | Phe | Ile | Thr | Asp | Gln | Gly | Arg | Ser |
|---|---|---|---|---|---|---|---|---|---|---|---|---|---|---|---|
| | | | | 260 | | | | | 265 | | | | | 270 | |

| Gly | Lys | Gln | Pro | Thr | Gly | Gln | Gln | Gln | Trp | Gly | Asp | Trp | Cys | Asn | Val |
|---|---|---|---|---|---|---|---|---|---|---|---|---|---|---|---|
| | | | 275 | | | | | 280 | | | | | 285 | | |

```
Ile  Gly  Thr  Gly  Phe  Gly  Ile  Arg  Pro  Ser  Ala  Asn  Thr  Gly  Asp  Ser
     290                 295                 300

Leu  Leu  Asp  Ser  Phe  Val  Trp  Val  Lys  Pro  Gly  Gly  Glu  Cys  Asp  Gly
305                      310                 315                           320

Thr  Ser  Asp  Ser  Ser  Ala  Pro  Arg  Phe  Asp  Ser  His  Cys  Ala  Leu  Pro
                    325                      330                 335

Asp  Ala  Leu  Gln  Pro  Ala  Pro  Gln  Ala  Gly  Ala  Trp  Phe  Gln  Ala  Tyr
               340                      345                      350

Phe  Val  Gln  Leu  Leu  Thr  Asn  Ala  Asn  Pro  Ser  Phe  Leu
          355                      360                 365
```

( 2 ) INFORMATION FOR SEQ ID NO:13:

( i ) SEQUENCE CHARACTERISTICS:
        ( A ) LENGTH: 1201 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(1..704, 775..1201)

( x i ) SEQUENCE DESCRIPTION: SEQ ID NO:13:

```
CAG  CAA  CCG  GGT  ACC  AGC  ACC  CCC  GAG  GTC  CAT  CCC  AAG  TTG  ACA  ACC     48
Gln  Gln  Pro  Gly  Thr  Ser  Thr  Pro  Glu  Val  His  Pro  Lys  Leu  Thr  Thr
 1                  5                       10                      15

TAC  AAG  TGT  ACA  AAG  TCC  GGG  GGG  TGC  GTG  GCC  CAG  GAC  ACC  TCG  GTG     96
Tyr  Lys  Cys  Thr  Lys  Ser  Gly  Gly  Cys  Val  Ala  Gln  Asp  Thr  Ser  Val
               20                       25                      30

GTC  CTT  GAC  TGG  AAC  TAC  CGC  TGG  ATG  CAC  GAC  GCA  AAC  TAC  AAC  TCG    144
Val  Leu  Asp  Trp  Asn  Tyr  Arg  Trp  Met  His  Asp  Ala  Asn  Tyr  Asn  Ser
          35                       40                      45

TGC  ACC  GTC  AAC  GGC  GGC  GTC  AAC  ACC  ACG  CTC  TGC  CCT  GAC  GAG  GCG    192
Cys  Thr  Val  Asn  Gly  Gly  Val  Asn  Thr  Thr  Leu  Cys  Pro  Asp  Glu  Ala
     50                       55                      60

ACC  TGT  GGC  AAG  AAC  TGC  TTC  ATC  GAG  GGC  GTC  GAC  TAC  GCC  GCC  TCG    240
Thr  Cys  Gly  Lys  Asn  Cys  Phe  Ile  Glu  Gly  Val  Asp  Tyr  Ala  Ala  Ser
65                       70                      75                       80

GGC  GTC  ACG  ACC  TCG  GGC  AGC  AGC  CTC  ACC  ATG  AAC  CAG  TAC  ATG  CCC    288
Gly  Val  Thr  Thr  Ser  Gly  Ser  Ser  Leu  Thr  Met  Asn  Gln  Tyr  Met  Pro
                    85                       90                      95

AGC  AGC  TCT  GGC  GGC  TAC  AGC  AGC  GTC  TCT  CCT  CGG  CTG  TAT  CTC  CTG    336
Ser  Ser  Ser  Gly  Gly  Tyr  Ser  Ser  Val  Ser  Pro  Arg  Leu  Tyr  Leu  Leu
               100                      105                     110

GAC  TCT  GAC  GGT  GAG  TAC  GTG  ATG  CTG  AAG  CTC  AAC  GGC  CAG  GAG  CTG    384
Asp  Ser  Asp  Gly  Glu  Tyr  Val  Met  Leu  Lys  Leu  Asn  Gly  Gln  Glu  Leu
          115                      120                     125

AGC  TTC  GAC  GTC  GAC  CTC  TCT  GCT  CTG  CCG  TGT  GGA  GAG  AAC  GGC  TCG    432
Ser  Phe  Asp  Val  Asp  Leu  Ser  Ala  Leu  Pro  Cys  Gly  Glu  Asn  Gly  Ser
     130                      135                     140

CTC  TAC  CTG  TCT  CAG  ATG  GAC  GAG  AAC  GGG  GGC  GCC  AAC  CAG  TAT  AAC    480
Leu  Tyr  Leu  Ser  Gln  Met  Asp  Glu  Asn  Gly  Gly  Ala  Asn  Gln  Tyr  Asn
145                      150                     155                      160

ACG  GCC  GGT  GCC  AAC  TAC  GGG  AGC  GGC  TAC  TGC  GAT  GCT  CAG  TGC  CCC    528
Thr  Ala  Gly  Ala  Asn  Tyr  Gly  Ser  Gly  Tyr  Cys  Asp  Ala  Gln  Cys  Pro
                    165                      170                     175

GTC  CAG  ACA  TGG  AGG  AAC  GGC  ACC  CTC  AAC  ACT  AGC  CAC  CAG  GGC  TTC    576
Val  Gln  Thr  Trp  Arg  Asn  Gly  Thr  Leu  Asn  Thr  Ser  His  Gln  Gly  Phe
               180                      185                     190
```

-continued

```
TGC TGC AAC GAG ATG GAT ATC CTG GAG GGC AAC TCG AGG GCG AAT GCC      624
Cys Cys Asn Glu Met Asp Ile Leu Glu Gly Asn Ser Arg Ala Asn Ala
        195                 200                 205

TTG ACC CCT CAC TCT TGC ACG GCC ACG GCC TGC GAC TCT GCC GGT TGC      672
Leu Thr Pro His Ser Cys Thr Ala Thr Ala Cys Asp Ser Ala Gly Cys
    210                 215                 220

GGC TTC AAC CCC TAT GGC AGC GGC TAC AAA AG  GTGAGCCTGA               714
Gly Phe Asn Pro Tyr Gly Ser Gly Tyr Lys Ser
225                 230                 235

TGCCACTACT ACCCCTTTCC TGGCGCTCTC GCGGTTTTCC ATGCTGACAT GGTTTTCCAG    774

C TAC TAC GGC CCC GGA GAT ACC GTT GAC ACC TCC AAG ACC TTC ACC        820
  Tyr Tyr Gly Pro Gly Asp Thr Val Asp Thr Ser Lys Thr Phe Thr
                  240                 245                 250

ATC ATC ACC CAG TTC AAC ACG GAC AAC GGC TCG CCC TCG GGC AAC CTT      868
Ile Ile Thr Gln Phe Asn Thr Asp Asn Gly Ser Pro Ser Gly Asn Leu
                255                 260                 265

GTG AGC ATC ACC CGC AAG TAC CAG CAA AAC GGC GTC GAC ATC CCC AGC      916
Val Ser Ile Thr Arg Lys Tyr Gln Gln Asn Gly Val Asp Ile Pro Ser
            270                 275                 280

GCC CAG CCC GGC GGC GAC ACC ATC TCG TCC TGC CCG TCC GCC TCA GCC  964
    Ala Gln Pro Gly Gly Asp Thr Ile Ser Ser Cys Pro Ser Ala Ser Ala
        285                 290                 295

TAC GGC GGC CTC GCC ACC ATG GGC AAG GCC CTG AGC AGC GGC ATG GTG     1012
Tyr Gly Gly Leu Ala Thr Met Gly Lys Ala Leu Ser Ser Gly Met Val
300                 305                 310

CTC GTG TTC AGC ATT TGG AAC GAC AAC AGC CAG TAC ATG AAC TGG CTC     1060
Leu Val Phe Ser Ile Trp Asn Asp Asn Ser Gln Tyr Met Asn Trp Leu
315                 320                 325                 330

GAC AGC GGC AAC GCC GGC CCC TGC AGC AGC ACC GAG GGC AAC CCA TCC     1108
Asp Ser Gly Asn Ala Gly Pro Cys Ser Ser Thr Glu Gly Asn Pro Ser
                335                 340                 345

AAC ATC CTG GCC AAC AAC CCC AAC ACG CAC GTC GTC TTC TCC AAC ATC     1156
Asn Ile Leu Ala Asn Asn Pro Asn Thr His Val Val Phe Ser Asn Ile
            350                 355                 360

CGC TGG GGA GAC ATT GGG TCT ACT ACG AAC TCG ACT GCG CCC CCG         1201
Arg Trp Gly Asp Ile Gly Ser Thr Thr Asn Ser Thr Ala Pro Pro
        365                 370                 375
```

( 2 ) INFORMATION FOR SEQ ID NO:14:

( i ) SEQUENCE CHARACTERISTICS:
        ( A ) LENGTH: 377 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
                20                  25                  30

Val Leu Asp Trp Asn Tyr Arg Trp Met His Asp Ala Asn Tyr Asn Ser
            35                  40                  45

Cys Thr Val Asn Gly Gly Val Asn Thr Thr Leu Cys Pro Asp Glu Ala
        50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Met Asn Gln Tyr Met Pro
                85                  90                  95
```

| Ser | Ser | Ser | Gly | Tyr | Ser | Ser | Val | Ser | Pro | Arg | Leu | Tyr | Leu | Leu |
|-----|-----|-----|-----|-----|-----|-----|-----|-----|-----|-----|-----|-----|-----|-----|
|     |     |     | 100 |     |     |     | 105 |     |     |     | 110 |     |     |     |

| Asp | Ser | Asp | Gly | Glu | Tyr | Val | Met | Leu | Lys | Leu | Asn | Gly | Gln | Glu | Leu |
|-----|-----|-----|-----|-----|-----|-----|-----|-----|-----|-----|-----|-----|-----|-----|-----|
|     |     | 115 |     |     |     | 120 |     |     |     |     | 125 |     |     |     |     |

| Ser | Phe | Asp | Val | Asp | Leu | Ser | Ala | Leu | Pro | Cys | Gly | Glu | Asn | Gly | Ser |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Leu | Tyr | Leu | Ser | Gln | Met | Asp | Glu | Asn | Gly | Gly | Ala | Asn | Gln | Tyr | Asn |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Thr | Ala | Gly | Ala | Asn | Tyr | Gly | Ser | Gly | Tyr | Cys | Asp | Ala | Gln | Cys | Pro |
|-----|-----|-----|-----|-----|-----|-----|-----|-----|-----|-----|-----|-----|-----|-----|-----|
|     |     |     |     | 165 |     |     |     |     | 170 |     |     |     | 175 |     |     |

| Val | Gln | Thr | Trp | Arg | Asn | Gly | Thr | Leu | Asn | Thr | Ser | His | Gln | Gly | Phe |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Cys | Cys | Asn | Glu | Met | Asp | Ile | Leu | Glu | Gly | Asn | Ser | Arg | Ala | Asn | Ala |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Leu | Thr | Pro | His | Ser | Cys | Thr | Ala | Thr | Ala | Cys | Asp | Ser | Ala | Gly | Cys |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gly | Phe | Asn | Pro | Tyr | Gly | Ser | Gly | Tyr | Lys | Ser | Tyr | Tyr | Gly | Pro | Gly |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Asp | Thr | Val | Asp | Thr | Ser | Lys | Thr | Phe | Thr | Ile | Ile | Thr | Gln | Phe | Asn |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Thr | Asp | Asn | Gly | Ser | Pro | Ser | Gly | Asn | Leu | Val | Ser | Ile | Thr | Arg | Lys |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Tyr | Gln | Gln | Asn | Gly | Val | Asp | Ile | Pro | Ser | Ala | Gln | Pro | Gly | Gly | Asp |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Thr | Ile | Ser | Ser | Cys | Pro | Ser | Ala | Ser | Ala | Tyr | Gly | Gly | Leu | Ala | Thr |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Met | Gly | Lys | Ala | Leu | Ser | Ser | Gly | Met | Val | Leu | Val | Phe | Ser | Ile | Trp |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Asn | Asp | Asn | Ser | Gln | Tyr | Met | Asn | Trp | Leu | Asp | Ser | Gly | Asn | Ala | Gly |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Pro | Cys | Ser | Ser | Thr | Glu | Gly | Asn | Pro | Ser | Asn | Ile | Leu | Ala | Asn | Asn |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Pro | Asn | Thr | His | Val | Val | Phe | Ser | Asn | Ile | Arg | Trp | Gly | Asp | Ile | Gly |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Ser | Thr | Thr | Asn | Ser | Thr | Ala | Pro | Pro |
|-----|-----|-----|-----|-----|-----|-----|-----|-----|
|     | 370 |     |     |     |     | 375 |     |     |

( 2 ) INFORMATION FOR SEQ ID NO:15:

( i ) SEQUENCE CHARACTERISTICS:
        ( A ) LENGTH: 1155 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(1..56, 231..1155)

( x i ) SEQUENCE DESCRIPTION: SEQ ID NO:15:

```
GGG  GTC  CGA  TTT  GCC  GGC  GTT  AAC  ATC  GCG  GGT  TTT  GAC  TTT  GGC  TGT       48
Gly  Val  Arg  Phe  Ala  Gly  Val  Asn  Ile  Ala  Gly  Phe  Asp  Phe  Gly  Cys
 1                   5                        10                       15

ACC  ACA   GA   GTGAGTACCC TTGTTTCCTG GTGTTGCTGG CTGGTTGGGC                          96
Thr  Thr  Asp

GGGTATACAG CGAAGCGGAC GCAAGAACAC CGCCGGTCCG CCACCATCAA GATGTGGGTG                    156
```

```
GTAAGCGGCG GTGTTTTGTA CAACTACCTG ACAGCTCACT CAGGAAATGA GAATTAATGG          216

AAGTCTTGTT ACAG T GGC ACT TGC GTT ACC TCG AAG GTT TAT CCT CCG              264
                  Gly Thr Cys Val Thr Ser Lys Val Tyr Pro Pro
                   20              25              30

TTG AAG AAC TTC ACC GGC TCA AAC AAC TAC CCC GAT GGC ATC GGC CAG           312
Leu Lys Asn Phe Thr Gly Ser Asn Asn Tyr Pro Asp Gly Ile Gly Gln
             35              40              45

ATG CAG CAC TTC GTC AAC GAG GAC GGG ATG ACT ATT TTC CGC TTA CCT           360
Met Gln His Phe Val Asn Glu Asp Gly Met Thr Ile Phe Arg Leu Pro
             50              55              60

GTC GGA TGG CAG TAC CTC GTC AAC AAC AAT TTG GGC GGC AAT CTT GAT           408
Val Gly Trp Gln Tyr Leu Val Asn Asn Asn Leu Gly Gly Asn Leu Asp
         65              70              75

TCC ACG AGC ATT TCC AAG TAT GAT CAG CTT GTT CAG GGG TGC CTG TCT           456
Ser Thr Ser Ile Ser Lys Tyr Asp Gln Leu Val Gln Gly Cys Leu Ser
         80              85              90

CTG GGC GCA TAC TGC ATC GTC GAC ATC CAC AAT TAT GCT CGA TGG AAC           504
Leu Gly Ala Tyr Cys Ile Val Asp Ile His Asn Tyr Ala Arg Trp Asn
 95             100             105             110

GGT GGG ATC ATT GGT CAG GGC GGC CCT ACT AAT GCT CAA TTC ACG AGC           552
Gly Gly Ile Ile Gly Gln Gly Gly Pro Thr Asn Ala Gln Phe Thr Ser
            115             120             125

CTT TGG TCG CAG TTG GCA TCA AAG TAC GCA TCT CAG TCG AGG GTG TGG           600
Leu Trp Ser Gln Leu Ala Ser Lys Tyr Ala Ser Gln Ser Arg Val Trp
            130             135             140

TTC GGC ATC ATG AAT GAG CCC CAC GAC GTG AAC ATC AAC ACC TGG GCT           648
Phe Gly Ile Met Asn Glu Pro His Asp Val Asn Ile Asn Thr Trp Ala
            145             150             155

GCC ACG GTC CAA GAG GTT GTA ACC GCA ATC CGC AAC GCT GGT GCT ACG           696
Ala Thr Val Gln Glu Val Val Thr Ala Ile Arg Asn Ala Gly Ala Thr
    160             165             170

TCG CAA TTC ATC TCT TTG CCT GGA AAT GAT TGG CAA TCT GCT GGG GCT           744
Ser Gln Phe Ile Ser Leu Pro Gly Asn Asp Trp Gln Ser Ala Gly Ala
175             180             185             190

TTC ATA TCC GAT GGC AGT GCA GCC GCC CTG TCT CAA GTC ACG AAC CCG           792
Phe Ile Ser Asp Gly Ser Ala Ala Ala Leu Ser Gln Val Thr Asn Pro
            195             200             205

GAT GGG TCA ACA ACG AAT CTG ATT TTT GAC GTG CAC AAA TAC TTG GAC           840
Asp Gly Ser Thr Thr Asn Leu Ile Phe Asp Val His Lys Tyr Leu Asp
            210             215             220

TCA GAC AAC TCC GGT ACT CAC GCC GAA TGT ACT ACA AAT AAC ATT GAC           888
Ser Asp Asn Ser Gly Thr His Ala Glu Cys Thr Thr Asn Asn Ile Asp
            225             230             235

GGC GCC TTT TCT CCG CTT GCC ACT TGG CTC CGA CAG AAC AAT CGC CAG           936
Gly Ala Phe Ser Pro Leu Ala Thr Trp Leu Arg Gln Asn Asn Arg Gln
240             245             250

GCT ATC CTG ACA GAA ACC GGT GGT GGC AAC GTT CAG TCC TGC ATA CAA           984
Ala Ile Leu Thr Glu Thr Gly Gly Gly Asn Val Gln Ser Cys Ile Gln
255             260             265             270

GAC ATG TGC CAG CAA ATC CAA TAT CTC AAC CAG AAC TCA GAT GTC TAT          1032
Asp Met Cys Gln Gln Ile Gln Tyr Leu Asn Gln Asn Ser Asp Val Tyr
            275             280             285

CTT GGC TAT GTT GGT TGG GGT GCC GGA TCA TTT GAT AGC ACG TAT GTC          1080
Leu Gly Tyr Val Gly Trp Gly Ala Gly Ser Phe Asp Ser Thr Tyr Val
            290             295             300

CTG ACG GAA ACA CCG ACT AGC AGT GGT AAC TCA TGG ACG GAC ACA TCC          1128
Leu Thr Glu Thr Pro Thr Ser Ser Gly Asn Ser Trp Thr Asp Thr Ser
            305             310             315

TTG GTC AGC TCG TGT CTC GCA AGA AAG                                      1155
```

```
Leu  Val  Ser  Ser  Cys  Leu  Ala  Arg  Lys
320                 325
```

( 2 ) INFORMATION FOR SEQ ID NO:16:

( i ) SEQUENCE CHARACTERISTICS:
        ( A ) LENGTH: 327 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Gly  Val  Arg  Phe  Ala  Gly  Val  Asn  Ile  Ala  Gly  Phe  Asp  Phe  Gly  Cys
 1              5                   10                  15
Thr  Thr  Asp  Gly  Thr  Cys  Val  Thr  Ser  Lys  Val  Tyr  Pro  Pro  Leu  Lys
          20                  25                       30
Asn  Phe  Thr  Gly  Ser  Asn  Asn  Tyr  Pro  Asp  Gly  Ile  Gly  Gln  Met  Gln
          35                  40                  45
His  Phe  Val  Asn  Glu  Asp  Gly  Met  Thr  Ile  Phe  Arg  Leu  Pro  Val  Gly
     50                  55                       60
Trp  Gln  Tyr  Leu  Val  Asn  Asn  Leu  Gly  Gly  Asn  Leu  Asp  Ser  Thr
65                       70                  75                            80
Ser  Ile  Ser  Lys  Tyr  Asp  Gln  Leu  Val  Gln  Gly  Cys  Leu  Ser  Leu  Gly
               85                       90                       95
Ala  Tyr  Cys  Ile  Val  Asp  Ile  His  Asn  Tyr  Ala  Arg  Trp  Asn  Gly  Gly
               100                 105                      110
Ile  Ile  Gly  Gln  Gly  Gly  Pro  Thr  Asn  Ala  Gln  Phe  Thr  Ser  Leu  Trp
          115                      120                 125
Ser  Gln  Leu  Ala  Ser  Lys  Tyr  Ala  Ser  Gln  Ser  Arg  Val  Trp  Phe  Gly
     130                      135                      140
Ile  Met  Asn  Glu  Pro  His  Asp  Val  Asn  Ile  Asn  Thr  Trp  Ala  Ala  Thr
145                      150                 155                           160
Val  Gln  Glu  Val  Val  Thr  Ala  Ile  Arg  Asn  Ala  Gly  Ala  Thr  Ser  Gln
                    165                 170                      175
Phe  Ile  Ser  Leu  Pro  Gly  Asn  Asp  Trp  Gln  Ser  Ala  Gly  Ala  Phe  Ile
               180                      185                      190
Ser  Asp  Gly  Ser  Ala  Ala  Ala  Leu  Ser  Gln  Val  Thr  Asn  Pro  Asp  Gly
          195                      200                 205
Ser  Thr  Thr  Asn  Leu  Ile  Phe  Asp  Val  His  Lys  Tyr  Leu  Asp  Ser  Asp
     210                      215                 220
Asn  Ser  Gly  Thr  His  Ala  Glu  Cys  Thr  Thr  Asn  Asn  Ile  Asp  Gly  Ala
225                      230                 235                           240
Phe  Ser  Pro  Leu  Ala  Thr  Trp  Leu  Arg  Gln  Asn  Asn  Arg  Gln  Ala  Ile
                    245                      250                 255
Leu  Thr  Glu  Thr  Gly  Gly  Gly  Asn  Val  Gln  Ser  Cys  Ile  Gln  Asp  Met
               260                      265                 270
Cys  Gln  Gln  Ile  Gln  Tyr  Leu  Asn  Gln  Asn  Ser  Asp  Val  Tyr  Leu  Gly
          275                      280                 285
Tyr  Val  Gly  Trp  Gly  Ala  Gly  Ser  Phe  Asp  Ser  Thr  Tyr  Val  Leu  Thr
     290                      295                 300
Glu  Thr  Pro  Thr  Ser  Ser  Gly  Asn  Ser  Trp  Thr  Asp  Thr  Ser  Leu  Val
305                      310                      315                      320
Ser  Ser  Cys  Leu  Ala  Arg  Lys
                    325
```

( 2 ) INFORMATION FOR SEQ ID NO:17:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..72

( x i ) SEQUENCE DESCRIPTION: SEQ ID NO:17:

| CGT | GGC | ACC | ACC | ACC | ACC | CGC | CGC | CCA | GCC | ACT | ACC | ACT | GGA | AGC | TCT | 48 |
|---|---|---|---|---|---|---|---|---|---|---|---|---|---|---|---|---|
| Arg | Gly | Thr | Thr | Thr | Thr | Arg | Arg | Pro | Ala | Thr | Thr | Thr | Gly | Ser | Ser | |
| 1 | | | | 5 | | | | | 10 | | | | | 15 | | |

| CCC | GGA | CCT | ACC | CAG | TCT | CAC | TAC | 72 |
|---|---|---|---|---|---|---|---|---|
| Pro | Gly | Pro | Thr | Gln | Ser | His | Tyr | |
| | | 20 | | | | | | |

( 2 ) INFORMATION FOR SEQ ID NO:18:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

Arg  Gly  Thr  Thr  Thr  Thr  Arg  Arg  Pro  Ala  Thr  Thr  Thr  Gly  Ser  Ser
 1                    5                        10                       15

Pro  Gly  Pro  Thr  Gln  Ser  His  Tyr
                20

( 2 ) INFORMATION FOR SEQ ID NO:19:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..129

( x i ) SEQUENCE DESCRIPTION: SEQ ID NO:19:

| GGC | GCT | GCA | AGC | TCA | AGC | TCG | TCC | ACG | CGC | GCC | GCG | TCG | ACG | ACT | TCT | 48 |
|---|---|---|---|---|---|---|---|---|---|---|---|---|---|---|---|---|
| Gly | Ala | Ala | Ser | Ser | Ser | Ser | Ser | Thr | Arg | Ala | Ala | Ser | Thr | Thr | Ser | |
| 1 | | | | 5 | | | | | 10 | | | | | 15 | | |

| CGA | GTA | TCC | CCC | ACA | ACA | TCC | CGG | TCG | AGC | TCC | GCG | ACG | CCT | CCA | CCT | 96 |
|---|---|---|---|---|---|---|---|---|---|---|---|---|---|---|---|---|
| Arg | Val | Ser | Pro | Thr | Thr | Ser | Arg | Ser | Ser | Ser | Ala | Thr | Pro | Pro | Pro | |
| | | | 20 | | | | | 25 | | | | 30 | | | | |

| GGT | TCT | ACT | ACT | ACC | AGA | GTA | CCT | CCA | GTC | GGA | 129 |
|---|---|---|---|---|---|---|---|---|---|---|---|
| Gly | Ser | Thr | Thr | Thr | Arg | Val | Pro | Pro | Val | Gly | |
| | | 35 | | | | | 40 | | | | |

( 2 ) INFORMATION FOR SEQ ID NO:20:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| Gly | Ala | Ala | Ser | Ser | Ser | Ser | Ser | Thr | Arg | Ala | Ala | Ser | Thr | Thr | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Val | Ser | Pro | Thr | Thr | Ser | Arg | Ser | Ser | Ser | Ala | Thr | Pro | Pro | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Ser | Thr | Thr | Thr | Arg | Val | Pro | Pro | Val | Gly |
|-----|-----|-----|-----|-----|-----|-----|-----|-----|-----|-----|
|     |     | 35  |     |     |     |     | 40  |     |     |     |

( 2 ) INFORMATION FOR SEQ ID NO:21:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..81

( x i ) SEQUENCE DESCRIPTION: SEQ ID NO:21:

| CCC | CCG | CCT | GCG | TCC | AGC | ACG | ACG | TTT | TCG | ACT | ACA | CCG | AGG | AGC | TCG | 48 |
|-----|-----|-----|-----|-----|-----|-----|-----|-----|-----|-----|-----|-----|-----|-----|-----|----|
| Pro | Pro | Pro | Ala | Ser | Ser | Thr | Thr | Phe | Ser | Thr | Thr | Pro | Arg | Ser | Ser |    |
| 1   |     |     |     | 5   |     |     |     |     | 10  |     |     |     |     | 15  |     |    |

| ACG | ACT | TCG | AGC | AGC | CCG | AGC | TGC | ACG | CAG | ACT | 81 |
|-----|-----|-----|-----|-----|-----|-----|-----|-----|-----|-----|----|
| Thr | Thr | Ser | Ser | Ser | Pro | Ser | Cys | Thr | Gln | Thr |    |
|     |     |     | 20  |     |     |     |     | 25  |     |     |    |

( 2 ) INFORMATION FOR SEQ ID NO:22:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

| Pro | Pro | Pro | Ala | Ser | Ser | Thr | Thr | Phe | Ser | Thr | Thr | Pro | Arg | Ser | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Thr | Ser | Ser | Ser | Pro | Ser | Cys | Thr | Gln | Thr |
|-----|-----|-----|-----|-----|-----|-----|-----|-----|-----|-----|
|     |     |     | 20  |     |     |     |     | 25  |     |     |

( 2 ) INFORMATION FOR SEQ ID NO:23:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..102

( x i ) SEQUENCE DESCRIPTION: SEQ ID NO:23:

| CCG | GGA | GCC | ACT | ACT | ATC | ACC | ACT | TCG | ACC | CGG | CCA | CCA | TCC | GGT | CCA | 48 |
|-----|-----|-----|-----|-----|-----|-----|-----|-----|-----|-----|-----|-----|-----|-----|-----|----|
| Pro | Gly | Ala | Thr | Thr | Ile | Thr | Thr | Ser | Thr | Arg | Pro | Pro | Ser | Gly | Pro |    |
| 1   |     |     |     | 5   |     |     |     |     | 10  |     |     |     |     | 15  |     |    |

| ACC | ACC | ACC | ACC | AGG | GCT | ACC | TCA | ACA | AGC | TCA | TCA | ACT | CCA | CCC | ACG | 96 |
|-----|-----|-----|-----|-----|-----|-----|-----|-----|-----|-----|-----|-----|-----|-----|-----|----|
| Thr | Thr | Thr | Thr | Arg | Ala | Thr | Ser | Thr | Ser | Ser | Ser | Thr | Pro | Pro | Thr |    |
|     |     |     | 20  |     |     |     |     | 25  |     |     |     |     | 30  |     |     |    |

| AGC | TCT | 102 |
|-----|-----|-----|

Ser  Ser ( 2 ) INFORMATION FOR SEQ ID NO:24:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Pro  Gly  Ala  Thr  Thr  Ile  Thr  Thr  Ser  Thr  Arg  Pro  Pro  Ser  Gly  Pro
 1              5                        10                       15
Thr  Thr  Thr  Thr  Arg  Ala  Thr  Ser  Thr  Ser  Ser  Ser  Thr  Pro  Pro  Thr
              20                        25                       30
Ser  Ser
```

( 2 ) INFORMATION FOR SEQ ID NO:25:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..51

( x i ) SEQUENCE DESCRIPTION: SEQ ID NO:25:

```
ATG  TAT  CGG  AAG  TTG  GCC  GTC  ATC  TCG  GCC  TTC  TTG  GCC  ACA  GCT  CGT    48
Met  Tyr  Arg  Lys  Leu  Ala  Val  Ile  Ser  Ala  Phe  Leu  Ala  Thr  Ala  Arg
 1              5                        10                       15

GCT                                                                               51
Ala
```

( 2 ) INFORMATION FOR SEQ ID NO:26:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met  Tyr  Arg  Lys  Leu  Ala  Val  Ile  Ser  Ala  Phe  Leu  Ala  Thr  Ala  Arg
 1              5                        10                       15
Ala
```

( 2 ) INFORMATION FOR SEQ ID NO:27:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..72

( x i ) SEQUENCE DESCRIPTION: SEQ ID NO:27:

| ATG | ATT | GTC | GGC | ATT | CTC | ACC | ACG | CTG | GCT | ACG | CTG | GCC | ACA | CTC | GCA | 48 |
| Met | Ile | Val | Gly | Ile | Leu | Thr | Thr | Leu | Ala | Thr | Leu | Ala | Thr | Leu | Ala | |
| 1 | | | | 5 | | | | | 10 | | | | | 15 | | |

| GCT | AGT | GTG | CCT | CTA | GAG | GAG | CGG | 72 |
| Ala | Ser | Val | Pro | Leu | Glu | Glu | Arg | |
| | | | 20 | | | | | |

( 2 ) INFORMATION FOR SEQ ID NO:28:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| Met | Ile | Val | Gly | Ile | Leu | Thr | Thr | Leu | Ala | Thr | Leu | Ala | Thr | Leu | Ala |
| 1 | | | | 5 | | | | | 10 | | | | | 15 | |

| Ala | Ser | Val | Pro | Leu | Glu | Glu | Arg |
| | | | 20 | | | | |

( 2 ) INFORMATION FOR SEQ ID NO:29:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..66

( x i ) SEQUENCE DESCRIPTION: SEQ ID NO:29:

| ATG | GCG | CCC | TCA | GTT | ACA | CTG | CCG | TTG | ACC | ACG | GCC | ATC | CTG | GCC | ATT | 48 |
| Met | Ala | Pro | Ser | Val | Thr | Leu | Pro | Leu | Thr | Thr | Ala | Ile | Leu | Ala | Ile | |
| 1 | | | | 5 | | | | | 10 | | | | | 15 | | |

| GCC | CGG | CTC | GTC | GCC | GCC | 66 |
| Ala | Arg | Leu | Val | Ala | Ala | |
| | | | 20 | | | |

( 2 ) INFORMATION FOR SEQ ID NO:30:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| Met | Ala | Pro | Ser | Val | Thr | Leu | Pro | Leu | Thr | Thr | Ala | Ile | Leu | Ala | Ile |
| 1 | | | | 5 | | | | | 10 | | | | | 15 | |

| Ala | Arg | Leu | Val | Ala | Ala |
| | | | 20 | | |

( 2 ) INFORMATION FOR SEQ ID NO:31:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
  ( A ) NAME/KEY: CDS
  ( B ) LOCATION: 1..63

( x i ) SEQUENCE DESCRIPTION: SEQ ID NO:31:

| ATG | AAC | AAG | TCC | GTG | GCT | CCA | TTG | CTG | CTT | GCA | GCG | TCC | ATA | CTA | TAT | 48 |
| Met | Asn | Lys | Ser | Val | Ala | Pro | Leu | Leu | Leu | Ala | Ala | Ser | Ile | Leu | Tyr | |
| 1 | | | | 5 | | | | | 10 | | | | | 15 | | |

| GGC | GGC | GCC | GTC | GCA | 63 |
| Gly | Gly | Ala | Val | Ala | |
| | | 20 | | | |

( 2 ) INFORMATION FOR SEQ ID NO:32:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: protein ( x i ) SEQUENCE DESCRIPTION: SEQ ID NO:32:

| Met | Asn | Lys | Ser | Val | Ala | Pro | Leu | Leu | Leu | Ala | Ala | Ser | Ile | Leu | Tyr |
| 1 | | | | 5 | | | | | 10 | | | | | 15 | |

| Gly | Gly | Ala | Val | Ala |
| | | 20 | | |

( 2 ) INFORMATION FOR SEQ ID NO:33:

( i ) SEQUENCE CHARACTERISTICS:
    ( A ) LENGTH: 777 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:33:

| AAACCAGCTG | TGACCAGTGG | GCAACCTTCA | CTGGCAACGG | CTACACAGTC | AGCAACAACC | 60 |
| TTTGGGGAGC | ATCAGCCGGC | TCTGGATTTG | GCTGCGTGAC | GGCGGTATCG | CTCAGCGGCG | 120 |
| GGGCCTCCTG | GCACGCAGAC | TGGCAGTGGT | CCGGCGGCCA | GAACAACGTC | AAGTCGTACC | 180 |
| AGAACTCTCA | GATTGCCATT | CCCCAGAAGA | GGACCGTCAA | CAGCATCAGC | AGCATGCCCA | 240 |
| CCACTGCCAG | CTGGAGCTAC | AGCGGGAGCA | ACATCCGCGC | TAATGTTGCG | TATGACTTGT | 300 |
| TCACCGCAGC | CAACCCGAAT | CATGTCACGT | ACTCGGGAGA | CTACGAACTC | ATGATCTGGT | 360 |
| AAGCCATAAG | AAGTGACCCT | CCTTGATAGT | TTCGACTAAC | AACATGTCTT | GAGGCTTGGC | 420 |
| AAATACGGCG | ATATTGGGCC | GATTGGGTCC | TCACAGGGAA | CAGTCAACGT | CGGTGGCCAG | 480 |
| AGCTGGACGC | TCTACTATGG | CTACAACGGA | GCCATGCAAG | TCTATTCCTT | TGTGGCCCAG | 540 |
| ACCAACACTA | CCAACTACAG | CGGAGATGTC | AAGAACTTCT | TCAATTATCT | CCGAGACAAT | 600 |
| AAAGGATACA | ACGCTGCAGG | CCAATATGTT | CTTAGTAAGT | CACCCTCACT | GTGACTGGGC | 660 |
| TGAGTTTGTT | GCAACGTTTG | CTAACAAAAC | CTTCGTATAG | GCTACCAATT | TGGTACCGAG | 720 |
| CCCTTCACGG | GCAGTGGAAC | TCTGAACGTC | GCATCCTGGA | CCGCATCTAT | CAACTAA | 777 |

( 2 ) INFORMATION FOR SEQ ID NO:34:

( i ) SEQUENCE CHARACTERISTICS:
    ( A ) LENGTH: 218 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:34:

| Gln | Thr | Ser | Cys | Asp | Gln | Trp | Ala | Thr | Phe | Thr | Gly | Asn | Gly | Tyr | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Val | Ser | Asn | Asn | Leu | Trp | Gly | Ala | Ser | Ala | Gly | Ser | Gly | Phe | Gly | Cys |
|     |     |     | 20  |     |     |     |     | 25  |     |     |     |     | 30  |     |     |
| Val | Thr | Ala | Val | Ser | Leu | Ser | Gly | Gly | Ala | Ser | Trp | His | Ala | Asp | Trp |
|     |     | 35  |     |     |     |     | 40  |     |     |     |     | 45  |     |     |     |
| Gln | Trp | Ser | Gly | Gly | Gln | Asn | Asn | Val | Lys | Ser | Tyr | Gln | Asn | Ser | Gln |
|     | 50  |     |     |     |     | 55  |     |     |     |     | 60  |     |     |     |     |
| Ile | Ala | Ile | Pro | Gln | Lys | Arg | Thr | Val | Asn | Ser | Ile | Ser | Ser | Met | Pro |
| 65  |     |     |     |     | 70  |     |     |     |     | 75  |     |     |     |     | 80  |
| Thr | Thr | Ala | Ser | Trp | Ser | Tyr | Ser | Gly | Ser | Asn | Ile | Arg | Ala | Asn | Val |
|     |     |     |     | 85  |     |     |     |     | 90  |     |     |     |     | 95  |     |
| Ala | Tyr | Asp | Leu | Phe | Thr | Ala | Ala | Asn | Pro | Asn | His | Val | Thr | Tyr | Ser |
|     |     |     | 100 |     |     |     |     | 105 |     |     |     |     | 110 |     |     |
| Gly | Asp | Tyr | Glu | Leu | Met | Ile | Trp | Leu | Gly | Lys | Tyr | Gly | Asp | Ile | Gly |
|     |     | 115 |     |     |     |     | 120 |     |     |     |     | 125 |     |     |     |
| Pro | Ile | Gly | Ser | Ser | Gln | Gly | Thr | Val | Asn | Val | Gly | Gly | Gln | Ser | Trp |
|     | 130 |     |     |     |     | 135 |     |     |     |     | 140 |     |     |     |     |
| Thr | Leu | Tyr | Tyr | Gly | Tyr | Asn | Gly | Ala | Met | Gln | Val | Tyr | Ser | Phe | Val |
| 145 |     |     |     |     | 150 |     |     |     |     | 155 |     |     |     |     | 160 |
| Ala | Gln | Thr | Asn | Thr | Thr | Asn | Tyr | Ser | Gly | Asp | Val | Lys | Asn | Phe | Phe |
|     |     |     |     | 165 |     |     |     |     | 170 |     |     |     |     | 175 |     |
| Asn | Tyr | Leu | Arg | Asp | Asn | Lys | Gly | Tyr | Asn | Ala | Ala | Gly | Gln | Tyr | Val |
|     |     |     | 180 |     |     |     |     | 185 |     |     |     |     | 190 |     |     |
| Leu | Ser | Tyr | Gln | Phe | Gly | Thr | Glu | Pro | Phe | Thr | Gly | Ser | Gly | Thr | Leu |
|     |     | 195 |     |     |     |     | 200 |     |     |     |     | 205 |     |     |     |
| Asn | Val | Ala | Ser | Trp | Thr | Ala | Ser | Ile | Asn |     |     |     |     |     |     |
|     | 210 |     |     |     |     | 215 |     |     |     |     |     |     |     |     |     |

( 2 ) INFORMATION FOR SEQ ID NO:35:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

ATGAAGTTCC TTCAAGTCCT CCCTGCCCTC ATACCGGCCG CCCTGGCC     48

( 2 ) INFORMATION FOR SEQ ID NO:36:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

| Met | Lys | Phe | Leu | Gln | Val | Leu | Pro | Ala | Leu | Ile | Pro | Ala | Ala | Leu | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

( 2 ) INFORMATION FOR SEQ ID NO:37:

( i ) SEQUENCE CHARACTERISTICS:
    ( A ) LENGTH: 57 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:37:

AGCTCGTAGA GCGTTGACTT GCCTGTGGTC TGTCCAGACG GGGACGATA GAATGCG 57

( 2 ) INFORMATION FOR SEQ ID NO:38:

( i ) SEQUENCE CHARACTERISTICS:
    ( A ) LENGTH: 48 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:38:

GTCACCTTCT CCAACATCAA GTTCGGACCC ATTGGCAGCA CCGGCTAA 48

( 2 ) INFORMATION FOR SEQ ID NO:39:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:39:

GGGGTTTAAA CCCGCGGGGA TT 22

( 2 ) INFORMATION FOR SEQ ID NO:40:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:40:

TGAGCCGAGG CCTCC 15

( 2 ) INFORMATION FOR SEQ ID NO:41:

( i ) SEQUENCE CHARACTERISTICS:
    ( A ) LENGTH: 18 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:41:

AGCTTGAGAT CTGAAGCT 18

( 2 ) INFORMATION FOR SEQ ID NO:42:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:42:

GATCGC 6

( 2 ) INFORMATION FOR SEQ ID NO:43:

( i ) SEQUENCE CHARACTERISTICS:
    ( A ) LENGTH: 16 base pairs ( B ) TYPE: nucleic acid
( C ) STRANDEDNESS: double
( D ) TOPOLOGY: linear ( x i ) SEQUENCE DESCRIPTION: SEQ ID NO:43:

TTATTAGTAA TATGCA 16

( 2 ) INFORMATION FOR SEQ ID NO:44:

( i ) SEQUENCE CHARACTERISTICS:
( A ) LENGTH: 26 base pairs
( B ) TYPE: nucleic acid
( C ) STRANDEDNESS: double
( D ) TOPOLOGY: linear ( x i ) SEQUENCE DESCRIPTION: SEQ ID NO:44:

CTAGAGGAGC GGTCGGGAAC CGCTAC 26

( 2 ) INFORMATION FOR SEQ ID NO:45:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:45:

Leu Glu Glu Arg Ser Gly Thr Ala Thr
1               5

( 2 ) INFORMATION FOR SEQ ID NO:46:

( i ) SEQUENCE CHARACTERISTICS:
( A ) LENGTH: 39 base pairs
( B ) TYPE: nucleic acid
( C ) STRANDEDNESS: double
( D ) TOPOLOGY: linear ( x i ) SEQUENCE DESCRIPTION: SEQ ID NO:46:

AAACCCGGG TGATTTATTT TTTTTGTATC TACTTCTGA 39

( 2 ) INFORMATION FOR SEQ ID NO:47:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:47:

Lys Pro Arg Val Ile Tyr Phe Phe Cys Ile Tyr Phe
1               5                   10

( 2 ) INFORMATION FOR SEQ ID NO:48:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:48:

Cys Gly Gly Gln Asn Val Ser Gly Pro Thr Cys Cys Ala Ser Gly Ser

-continued

| 1 | 5 | 10 | 15 |
|---|---|----|----|
| Thr Cys | | | |

CELLULASE ENZYMES AND SYSTEMS FOR THEIR EXPRESSIONS

This is Divisional of U.S. Ser. No. 08/169,948 filed Dec. 17, 1993, now pending.

FIELD OF THE INVENTION

The present invention relates to a process for producing high levels of novel truncated cellulase proteins in the filamentous fungus *Trichoderma longibrachiatum*; to fungal transformants produced from *Trichoderma longibrachiatum* by genetic engineering techniques; and to novel cellulase proteins produced by such transformants.

BACKGROUND OF THE INVENTION

Cellulases are enzymes which hydrolyze cellulose (β-1, 4-D-glucan linkages) and produce as primary products glucose, cellobiose, cellooligosaccharides, and the like. Cellulases are produced by a number of microorganisms and comprise several different enzyme classifications including those identified as exo-cellobiohydrolases (CBH), endoglucanases (EG) and β-glucosidases (BG) (Schulein, M, 1988 Methods in Enzymology 160: 235–242). Moreover, the enzymes within these classifications can be separated into individual components. For example, the cellulase produced by the filamentous fungus, *Trichoderma longibrachiatum*, hereafter *T. longibrachiatum*, consists of at least two CBH components, i.e., CBHI and CBHII, and at least four EG components, i.e., EGI, EGII, EGIII and EGV (Saloheimo, A. et al 1993 in Proceedings of the second TRICEL symposium on *Trichoderma reesei* Cellulases and Other Hydrolases, Espoo, Finland, ed by P. Suominen & T. Reinikainen. Foundation for Biotechnical and Industrial Fermentation Research 8: 139–146) components, and at least one β-glucosidase. The genes encoding these components are namely cbh1, cbh2, egI1, egI2, egI3, and egI5 respectively.

The complete cellulase system comprising CBH, EG and BG components synergistically act to convert crystalline cellulose to glucose. The two exo-cellobiohyrolases and the four presently known endoglucanases act together to hydrolyze cellulose to small cello-oligosaccharides. The oligosaccharides (mainly cellobioses) are subsequently hydrolyzed to glucose by a major β-glucosidase (with possible additional hydrolysis from minor β-glucosidase components).

Protein analysis of the cellobiohydrolases (CBHI and CBHII) and major endoglucanases (EGI and EGI) of *T. longibrachiatum* have shown that a bifunctional organization exists in the form of a catalytic core domain and a smaller cellulose binding domain separated by a linker or flexible hinge stretch of amino acids rich in proline and hydroxyamino acids. Genes for the two cellobiohydrolases, CBHI and CBHII (Shoemaker, S. et al 1983 Bio/Technology 1, 691–696, Teeri, T. et al 1983, Bio/Technology 1, 696–699 and Teeri, T. et al, 1987, Gene 51, 43–52) and two major endoglucansases, EGI and EGII (Penttila, M. et al 1986, Gene 45, 253–263, Van Arsdell, J. N./et al 1987 Bio/Technology 5, 60–64 and Saloheimo, M. et al 1988, Gene 63, 11–21) have been isolated from *T. longibrachiatum* and the protein domain structure has been confirmed.

A similar bifunctional organization of cellulase enzymes is found in bacterial cellulases. The cellulose binding domain (CBD) and catalytic core of *Cellulomonas fimi* endoglucanase A (*C. fimi* Cen A) has been studied extensively (Ong E. et al 1989, Trends Biotechnol. 7:239–243, Pilz et al 1990, Biochem J. 271:277–280 and Warren et al 1987, Proteins 1:335–341). Gene fragments encoding the CBD and the CBD with the linker have been cloned, expressed in *E. coli* and shown to possess novel activities on cellulose fibers (Gilkes, N. R. et al 1991, Microbiol Rev. 55:305–315 and Din, N. et al 1991, Bio/Technology 9:1096–1099). For example, isolated CBD from *C. fimi* Cen A genetically expressed in *E. coli* disrupts the structure of cellulose fibers and releases small particles but have no detectable hydrolytic activity. CBD further possess a wide application in protein purification and enzyme immobilization. On the other hand, the catalytic domain of *C. fimi* Cen A isolated from protease cleaved cellulase does not disrupt the fibril structure of cellulose and instead smooths the surface of the fiber.

These novel activities have potential uses in textile, food and animal feed, detergents and the pulp and paper industries. However, for industrial application, highly efficient expression systems must be procured that produce higher yields of truncated cellulase proteins than are currently available to be of any commercial value. For example, *Trichoderma longibrachiatum* CBHI core domains have been separated proteolytically and purified but only milligram quantities are isolated by this biochemical procedure (Offord D., et al 1991, Applied Biochem. and Biotech. 28/29:377–386). Similar studies were done in an analysis of the core and binding domains of CBHI, CBHII, EGI and EGII isolated from *T. longibrachiatum* after biochemical proteolysis, however, only enough protein was recovered for structural and functional analysis (Tomme, P. et al, 1988, Eur. J. Biochem 170:575–581 and Ajo, S., 1991 FEBS 291:45–49).

In order to obtain strains which express higher levels of truncated cellulase proteins than previously realized, applicants chose *T. longibrachiatum* as the microorganism most preferred for expression since it is well known for its capacity to secrete whole cellulases in large quantities. Thus, applicants set out to genetically engineer strains of the above filamentous fungus to express high levels of bioengineered novel protein truncated cellulases.

It remained unknown before Applicants invention whether the DNA encoding truncated cellulase binding and core domain proteins could be transformed into Trichoderma in such a manner as to overexpress novel truncated cellulase genes into functional proteins without deterioration in the host cell and obtained secretion to facilitate identification and purification of the engineered product. Recently, Nakari and Penttila have shown that it is possible to genetically engineer a Trichoderma host to express a truncated form of the Trichoderma EGI cellulase, specifically the catalytic core domain, however the level of expression of EGI core domain was low (Nakari, T. et al, Abstract P1/63 1st European Conference on Fungal Genetics, Nottingham, England, Aug. 20–23, 1992). Moreover, it was unknown whether a Trichoderma cellobiohydrolase catalytic core domain or any Trichoderma cellobiohydrolase or endoglucanase cellulose binding domain could be produced by recombinant genetic methods.

Accordingly, it is an object of the present invention to introduce DNA gene fragments into strains of the fungus, *Trichoderma longibrachiatum* to produce transformant strains that express high levels of novel truncated protein (grams/liter level) engineered cellulases from the binding and core domains of Trichoderma cellulases. The truncated proteins are correctly processed and secreted extracellularly in an active form. The present invention further relates to the novel truncated proteins isolated from these transformants.

SUMMARY OF THE INVENTION

Methods involving recombinant DNA technology and compositions are provided for the production and isolation of novel truncated cellulase proteins, derivatives thereof or covalently linked truncated cellulase domain derivatives derived from the filamentous fungus, Trichoderma sp. The truncated cellulase comprises at least a core or binding domain of a cellobiohydrolases or endoglucanase from the species Trichoderma. Derivatives of truncated cellulases include substitutions, deletions, or additions of one or more amino acids at various sites throughout the core or binding domain of the novel truncated cellulase whereby either the cellulose binding or cellulase catalytic core activity is retained. Covalently linked truncated cellulase domain derivatives comprise truncated cellulases or derivatives thereof that are further attached to each other, and/or enzymes, or domains and/or proteins, and/or chemicals heterologous or homologous to Trichoderma sp.

The present invention also includes the preparation of novel truncated cellulases, derivatives and covalently linked truncated cellulase domain derivatives by transforming into a host cell a DNA construct comprising a DNA fragment or variant thereof encoding the above novel cellulase(s) functionally attached to regulatory sequences that permit the transcription and translation of the structural gene and growing the host cell to express the truncated gene of interest.

The present invention further includes DNA fragments and variants thereof encoding novel truncated cellulases, derivatives and covalently linked truncated cellulase domain derivatives. The present invention also encompasses expression vectors comprising the above DNA fragments or variants thereof and Trichoderma host cells transformed with the above expression vectors.

BRIEF DETAILED DESCRIPTION OF THE DRAWINGS

FIG. 1 depicts the genomic DNA and amino acid sequence of CBHI derived from *Trichoderma longibrachiatum*. The signal sequence begins at base pair 210 and ends at base pair 260 (Seq ID No. 25). The catalytic core domain begins at base pair 261 through base pair 671 of the first exon, base pair 739 through base pair 1434 of the second exon, and base pair 1498 through base pair 713 of the third exon (Seq ID No. 9). The linker sequence begins at base pair 714 and ends at base pair 1785 (Seq ID No. 17). The cellulase binding domain begins at base pair 1786 and ends at base pair 1888 (Seq ID No. 1). Seq ID Nos. 26, 10, 18 and 2 represent the amino acid sequence of the CBHI signal sequence, catalytic core domain, linker region and binding domain, respectively.

FIG. 2 depicts the genomic DNA and amino acid sequence of CBHII derived from *Trichoderma longibrachiatum*. The signal sequence begins at base pair 614 and ends at base pair 685 (Seq ID No. 27). The cellulose binding domain begins at base pair 686 through base pair 707 of exon one, and base pair 755 through base pair 851 of exon two (Seq ID No. 3). The linker sequence begins at base pair 852 and ends at base pair 980 (Seq ID No. 19). The catalytic core begins at base pair 981 through base pair 1141 of exon two, base pair 1199 through base pair 1445 of exon three and base pair 1536 through base pair 2221 of exon four (Seq ID No. 11). Seq ID Nos. 28, 4, 20 and 12 represent the amino acid sequence of the CBHII signal sequence, binding domain, linker region and catalytic core domain, respectively.

FIG. 3 depicts the genomic DNA and amino acid sequence of EGI. The signal sequence begins at base pair 113 and ends at base pair 178 (Seq ID No. 29). The catalytic core domain begins at base pair 179 through 882 of exon one, and base pair 963 through base pair 1379 of the second exon (Seq ID No. 13). The linker region begins at base pair 1380 and ends at base pair 1460 (Seq ID No. 21). The cellulose binding domain begins at base pair 1461 and ends at base pair 1616 (Seq ID No. 5). Seq ID Nos. 30, 14, 22 and 6 represent the amino acid sequence of EGI signal sequence, catalytic core domain, linker region and binding domain, respectively.

FIG. 4 depicts the genomic DNA and amino acid sequence of EGII. The signal sequence begins at base pair 262 and ends at base pair 324 (Seq ID No. 31). The cellulose binding domain begins at base pair 325 and ends at base pair 432 (Seq ID No. 7). The linker region begins at base pair 433 and ends at base pair 534 (Seq No. 23). The catalytic core domain begins at base pair 535 through base pair 590 in exon one, and base pair 765 through base pair 1689 in exon two (Seq ID No. 15). Seq ID Nos. 32, 8, 24 and 16 represent the amino acid sequence of EGII signal sequence, binding domain, linker region and catalytic core domain, respectively.

FIG. 5 depicts the genomic DNA and amino acid sequence of EGIII. The signal sequence begins at base pair 151 and ends at base pair 198 (SEQ ID No. 35). The catalytic core domain begins at base pair 199 through base pair 557 in exon one, base pair 613 through base pair 833 in exon two and base pair 900 through base pair 973 in exon three (Seq ID No. 33). Seq ID Nos. 36 and 34 represent the amino acid sequence of EGIII signal sequence and catalytic core domain, respectively.

FIG. 6 illustrates the construction of EGI core domain expression vector (Seq ID No. 37).

FIG. 7 depicts the construction of the expression plasmid pTEX (Seq ID Nos. 39–41).

FIG. 8 is an illustration of the construction of CBHI core domain expression vector (Seq ID No. 38).

FIG. 9 is an illustration of the construction of CBHII cellulase binding domain expression vector (Seq ID Nos. 42 and 43).

DETAILED DESCRIPTION

As noted above, the present invention generally relates to the cloning and expression of novel truncated cellulase proteins at high levels in the filamentous fungus, *T. longibrachiatum*. Further aspects of the present invention will be discussed in further detail following a definition of the terms employed herein.

The term "Trichoderma" or "Trichoderma sp." refers to any fungal strains which have previously been classified as Trichoderma or which are currently classified as Trichoderma. Preferably the species are *Trichoderma longibrachiatum, Trichoderma reesei* or *Trichoderma viride*.

The terms "cellulolytic enzymes" or "cellulase enzymes" refer to fungal exoglucanases or exocellobiohydrolases (CBH), endoglucanses (EG) and β-glucosidases (BG). These three different types of cellulase enzymes act synergistically to convert crystalline cellulose to glucose. Analysis of the genes coding for CBHI, CBHII and EGI and EGII show a domain structure comprising a catalytic core region (CCD), a hinge or linker region (used interchangeably herein) and cellulose binding region (CBD).

The term "truncated cellulases", as used herein, refers to the core or binding domains of the cellobiohydrolases and endoglucanases, for example, EGI, EGII, EGIII, EGV, CBHI and CBHII, or derivatives of either of the truncated cellulase domains.

A "derivative" of the truncated cellulases encompasses the core or binding domains of the cellobiohydrolases, for example, CBHI or CBHII, and the endoglucanases, for example, EGI, EGII, EGIII and EGV from Trichoderma sp, wherein there may be an addition of one or more amino acids to either or both of the C- and N-terminal ends of the truncated cellulase, a substitution of one or more amino acids at one or more sites throughout the truncated cellulase, a deletion of one or more amino acids within or at either or both ends of the truncated cellulase protein, or an insertion of one or more amino acids at one or more sites in the truncated cellulase protein such that exoglucanase and endoglucanase activities are retained in the derivatized CBH and EG catalytic core truncated proteins and/or the cellulose binding activity is retained in the derivatized CBH and EG binding domain truncated proteins. It is also intended by the term "derivative of a truncated cellulase" to include core or binding domains of the exoglucanase or endoglucanase enzymes that have attached thereto one or more amino acids from the linker region.

A truncated cellulase protein derivative further refers to a protein substantially similar in structure and biological activity to a cellulase core or binding domain which comprises the cellulolytic enzymes found in nature, but which has been engineered to contain a modified amino acid sequence. Thus, provided that the two proteins possess a similar activity, they are considered "derivatives" as that term is used herein even if the primary structure of one protein does not possess the identical amino acid sequence to that found in the other.

The term "cellulase catalytic core domain activity" refers herein to an amino acid sequence of the truncated cellulase comprising the core domain of the cellobiohydrolases and endoglucanases, for example, EGI, EGII, EGIII, EGV, CBHI or CBHII or a derivative thereof that is capable of enzymatically cleaving a cellulosic polymers such as pulp or phosphoric acid swollen cellulose.

The activity of the truncated catalytic core proteins or derivatives thereof as defined herein may be determined by methods well known in the art. (See Wood, T. M. et al in Methods in Enzymology, Vol. 160, Editors: Wood, W. A. and Kellogg, S. T., Academic Press, pp. 87–116, 1988) For example, such activities can be determined by hydrolysis of phosphoric acid-swollen cellulose and/or soluble oligosaccharides followed by quantification of the reducing sugars released. In this case the soluble sugar products, released by the action of CBH or EG catalytic domains or derivatives thereof, can be detected by HPLC analysis or by use of colorimetric assays for measuring reducing sugars. It is expected that these catalytic domains or derivatives thereof will retain at least 10% of the activity exhibited by the intact enzyme when each is assayed under similar conditions and dosed based on similar amounts of catalytic domain protein.

The term "cellulose binding domain activity" refers herein to an amino acid sequence of the cellulase comprising the binding domain of cellobiohydrolases and endoglucanases, for example, EGI, EGII, CBHI or CHBII or a derivative thereof that non-covalently binds to a polysaccharide such as cellulose. It is believed that cellulose binding domains (CBDs) function independently from the catalytic core of the cellulase enzyme to attach the protein to cellulose.

The performance (or activity) of the truncated binding domain or derivatives thereof as described in the present invention may be determined by cellulose binding assays using a cellulosic substrates such as avicel, pulp or cotton, for example. It is expected that these novel truncated binding domains or derivatives thereof will retain at least 10% of the binding affinity compared to that exhibited by the intact enzyme when each is assayed under similar conditions and dosed based on similar amounts of binding domain protein. The amount of non-bound binding domain may be quantified by direct protein analysis, by chromatographic methods, or possibly by immunological methods.

Other methods well known in the art that measure cellulase catalytic and/or binding activity via the physical or chemical properties of particular treated substrates may also be suitable in the present invention. For example, for methods that measure physical properties of a treated substrate, the substrate is analyzed for modification of shape, texture, surface, or structional properties, modification of the "wet" ability, e.g. substrates ability to absorb water, or modification of swelling. Other parameters which may determine activity include the measuring of the change in the chemical properties of treated solid substrates. For example, the diffusion properties of dyes or chemicals may be examined after treatment of solid substrate with the truncated cellulase binding protein or derivatives thereof described in the present invention. Appropriate substrates for evaluating activity include Avicel, rayon, pulp fibers, cotton or ramie fibers, paper, kraft or ground wood pulp, for example. (See also Wood, T. M. et al in "Methods in Enzymology", Vol. 160, Editors: Wood, W. A. and Kellogg, S. T., Academic Press, pp. 87–116, 1988)

The term "linker or hinge region" refers to the short peptide region that links together the two distinct functional domains of the fungal cellulases, i.e., the core domain and the binding domain. These domains in *T. longibrachiatum* cellulases are linked by a peptide rich in Ser Thr and Pro.

A "signal sequence" refers to any sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

The term "variant" refers to a DNA fragment encoding the CBH or EG core or binding domain that may further contain an addition of one or more nucleotides internally or at the 5' or 3' end of the DNA fragment, a deletion of one or more nucleotides internally or at the 5' or 3' end of the DNA fragment or a substitution of one or more nucleotides internally or at the 5' or 3' end of the DNA fragment wherein the functional activity of the binding and core domains that encode for a truncated cellulase is retained.

A variant DNA fragment comprising the core or binding domain is further intended to indicate that a linker or hinge DNA sequence or portion thereof may be attached to the core or binding domain DNA sequence at either the 5' or 3' end wherein the functional activity of the encoded truncated binding or core domain protein (derivative) is retained.

The term "host cell" means both the cells and protoplasts created from the cells of Trichoderma sp.

The term "DNA construct or vector" (used interchangeably herein) refers to a vector which comprises one or more DNA fragments or DNA variant fragments encoding any one of the novel truncated cellulases or derivatives described above.

The term "functionally attached to" means that a regulatory region, such as a promoter, terminator, secretion signal or enhancer region is attached to a structural gene and controls the expression of that gene.

The present invention relates to truncated cellulases, derivatives of truncated cellulases and covalently linked truncated cellulase domain derivatives that are prepared by recombinant methods by transforming into a host cell, a DNA construct comprising at least a fragment of DNA encoding a portion or all of the binding or core region of the cellobiohydrolases or endoglucanases, for example, EGI, EGII, EGIII; EGV, CBHI or CBHII functionally attached to a promoter, growing the host cell to express the truncated cellulase, derivative truncated cellulase or covalently linked truncated cellulase domain derivatives of interest and subsequently purifying the truncated cellulase, or derivative thereof to substantial homogeneity.

It is further contemplated by the present invention that one may generate novel derivatives of cellulase enzymes which, for instance, combine a core region derived from a truncated endoglucanase or exocellobiohydrolase of the present invention with a cellulose-binding domain derived from another cellulase enzyme from multiple microbial sources such as fungal and bacterial. Alternatively, it may be possible to combine a core region derived from another cellulase enzyme with a cellulose-binding domains derived from a truncated endoglucanase or exocellobiohydralase of the present invention. In a particular embodiment, the core region may be derived from a cellulase enzyme which does not in nature comprise a cellulose-binding domain, for example, EGIII (FIG. 5 and SEQ ID Nos. 33 and 34), and which is N- or C-terminally extended with a truncated cellulase or derivative thereof comprising a cellulose-binding domain described herein. In this way, it may be possible to construct novel cellulase enzymes with altered cellulose binding properties compared to natural intact cellulases.

In yet another aspect of the present invention, it is contemplated that truncated cellulases or derivatives thereof of the present invention may be further attached to each other and/or to intact proteins and/or enzymes and/or portions thereof, for example, hemicellulases, immunoglobulins, and/or binding or core domains from non Trichoderma cellulases, and/or from non-cellulase enzymes using the recombinant methods described herein to form novel covalently linked truncated cellulase domain derivatives. These covalently linked truncated cellulase domain derivatives constructed in this manner may provide even further benefits over the truncated cellulases or derivatives thereof disclosed in the present invention. It is contemplated that these covalently linked truncated cellulase domain derivatives which contain other enzymes, proteins or portions thereof may exhibit bifunctional activity and/or bifunctional binding.

In yet a further aspect, the present invention relates to a method of producing a truncated cellulase or derivative thereof which method comprises cultivating a host cell as described above under conditions such that production of the truncated cellulase or derivative thereof is effected and recovering the truncated cellulase or derivative from the cells or culture medium.

Highly enriched truncated cellulases are prepared in the present invention by genetically modifying microorganisms described in further detail below. Transformed microorganism cultures are grown to stationary phase, filtered to remove the cells and the remaining supernatant is concentrated by ultrafiltration to obtain a truncated cellulase or a derivative thereof.

In a particular aspect of the above method, the medium used to cultivate the transformed host cells may be any medium suitable for cellulase production in Trichoderma. The truncated cellulases or derivatives thereof are recovered from the medium by conventional techniques including separations of the cells from the medium by centrifugation, or filtration, precipitation of the proteins in the supernatant or filtrate with salt, for example, ammonium sulphate, followed by chromatography procedures such as ion exchange chromatography, affinity chromatography and the like.

Alternatively, the final protein product may be isolated and purified by binding to a polysaccharide substrate or antibody matrix. The antibodies (polyclonal or monoclonal) may be raised against cellulase core or binding domain peptides, or synthetic peptides may be prepared from portions of the core domain or binding domain and used to raise polyclonal antibodies.

In a general embodiment of the present method, one or more functionally active truncated cellulases or derivatives thereof is expressed in a Trichoderma host cell transformed with a DNA vector comprising one or more DNA fragments or variant fragments encoding truncated cellulases, derivatives thereof or covalently linked truncated cellulase domain derivative proteins. The Trichoderma host cell may or may not have been previously manipulated through genetic engineering to remove any host genes that encode intact cellulases.

In a particular embodiment, truncated cellulases, derivatives thereof or covalently linked truncated cellulase domain derivatives are expressed in transformed Trichoderma cells in which genes have not been deleted therefrom. The truncated proteins listed above are recovered and separated from intact cellulases expressed simultaneously in the host cells by conventional procedures discussed above including sizing chromatography. Confirmation of expression of truncated cellulases or derivatives is determined by SDS polyacrylamide gel electrophoresis and Western immunoblot analysis to distinguish truncated from intact cellulase proteins.

In a preferred embodiment, the present invention relates to a method for transforming a Trichoderma sp host cell that is missing one or more cellulase activities and treating the cell using recombinant DNA techniques well known in the art with one or more DNA fragments encoding a truncated cellulase, derivative thereof or covalently linked truncated cellulase domain derivatives. It is contemplated that the DNA fragment encoding a derivative truncated cellulase core or binding domain may be altered such as by deletions, insertions or substitutions within the gene to produce a variant DNA that encodes for an active truncated cellulase derivative.

It is further contemplated by the present invention that the DNA fragment or DNA variant fragment encoding the truncated cellulase or derivative may be functionally attached to a fungal promoter sequence, for example, the promoter of the cbh1 or egI1 gene. Also contemplated by the present invention is manipulation of the Trichoderma sp. strain via transformation such that a DNA fragment encoding a truncated cellulase or derivative thereof is inserted within the genome. It is also contemplated that more than one copy of a truncated cellulase DNA fragment or DNA variant fragment may be recombined into the strain.

A selectable marker must first be chosen so as to enable detection of the transformed fungus. Any selectable marker gene which is expressed in Trichoderma sp. can be used in the present invention so that its presence in the transformants will not materially affect the properties thereof. The selectable marker can be a gene which encodes an assayable product. The selectable marker may be a functional copy of a Trichoderma sp gene which if lacking in the host strain results in the host strain displaying an auxotrophic phenotype.

The host strains used could be derivatives of Trichoderma sp which lack or have a nonfunctional gene or genes corresponding to the selectable marker chosen. For example, if the selectable marker of pyr4 is chosen, then a specific pyr derivative strain is used as a recipient in the transformation procedure. Other examples of selectable markers that can be used in the present invention include the Trichoderma sp. genes equivalent to the *Aspergillus nidulans* genes argB, trpC, niaD and the like. The corresponding recipient strain must therefore be a derivative strain such as argB⁻, trpC⁻, niaD⁻, and the like.

The strain is derived from a starting host strain which is any Trichoderma sp. strain. However, it is preferable to use a *T. longibrachiatum* cellulase over-producing strain such as RL-P37, described by Sheir-Neiss et al. in Appl. Microbiol. Biotechnology, 20 (1984) pp. 46–53, since this strain secretes elevated amounts of cellulase enzymes. This strain is then used to produce the derivative strains used in the transformation process.

The derivative strain of Trichoderma sp. can be prepared by a number of techniques known in the art. An example is the production of pyr4⁻ derivative strains by subjecting the strains to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4⁻ derivative strains which lack a functional orotidine monophosphate decarboxylase enzyme and require uridine for growth by selecting for FOA resistance. Using the FOA selection technique it is also possible to obtain uridine requiring strains which lack a functional orotate pyrophosphoribosyl transferase. It is possible to transform these cells with a functional copy of the gene encoding this enzyme (Berges and Barreau, 1991, Curr. Genet. 19 pp359–365). Since it is easy to select derivative strains using the FOA resistance technique in the present invention, it is preferable to use the pyr4 gene as a selectable marker.

In a preferred embodiment of the present invention, Trichoderma host cell strains have been deleted of one or more cellulase genes prior to introduction of a DNA construct or plasmid containing the DNA fragment encoding the truncated cellulase protein of interest. It is preferable to express a truncated cellulase, derivative thereof or covalently linked truncated cellulase domain derivatives in a host that is missing one or more cellulase genes in order to simplify the identification and subsequent purification procedures. Any gene from Trichoderma sp. which has been cloned can be deleted such as cbh1, cbh2, egl1, egl3, and the like. The plasmid for gene deletion is selected such that unique restriction enzyme sites are present therein to enable the fragment of homologous Trichoderma sp. DNA to be removed as a single linear piece.

The desired gene that is to be deleted from the transformant is inserted into the plasmid by methods known in the art. The plasmid containing the gene to be deleted or disrupted is then cut at appropriate restriction enzyme site(s), internal to the coding region, the gene coding sequence or part thereof may be removed therefrom and the selectable marker inserted. Flanking DNA sequences from the locus of the gene to be deleted or disrupted, preferably between about 0.5 to 2.0 kb, remain on either side of the selectable marker gene.

A single DNA fragment containing the deletion construct is then isolated from the plasmid and used to transform the appropriate pyr⁻ Trichoderma host. Transformants are selected based on their ability to express the pyr4 gene product and thus compliment the uridine auxotrophy of the host strain. Southern blot analysis is then carried out on the resultant transformants to identify and confirm a double cross over integration event which replaces part or all of the coding region of the gene to be deleted with the pyr4 selectable markers.

Although specific plasmid vectors are described above, the present invention is not limited to the production of these vectors. Various genes can be deleted and replaced in the Trichoderma sp. strain using the above techniques. Any available selectable markers can be used, as discussed above. Potentially any Trichoderma sp. gene which has been cloned, and thus identified, can be deleted from the genome using the above-described strategy. All of these variations are included within the present invention.

The expression vector of the present invention carrying the inserted DNA fragment or variant DNA fragment encoding the truncated cellulase or derivative thereof of the present invention may be any vector which is capable of replicating autonomously in a given host organism, typically a plasmid. In preferred embodiments two types of expression vectors for obtaining expression of genes or truncations thereof are contemplated. The first contains DNA sequences in which the promoter, gene coding region, and terminator sequence all originate from the gene to be expressed. The gene truncation is obtained by deleting away the undesired DNA sequences (coding for unwanted domains) to leave the domain to be expressed under control of its own transcriptional and translational regulatory sequences. A selectable marker is also contained on the vector allowing the selection for integration into the host of multiple copies of the novel gene sequences.

For example, pEGIΔ3' pyr contains the EGI cellulase core domain under the control of the EGI promoter, terminator, and signal sequences. The 3' end on the EGI coding region containing the cellulose binding domain has been deleted. The plasmid also contains the pyr4 gene for the purpose of selection.

The second type of expression vector is preassembled and contains sequences required for high level transcription and a selectable marker. It is contemplated that the coding region for a gene or part thereof can be inserted into this general purpose expression vector such that it is under the transcriptional control of the expression cassettes promoter and terminator sequences.

For example, pTEX is such a general purpose expression vector. Genes or part thereof can be inserted downstream of the strong CBHI promoter. The Examples disclosed herein are included in which cellulase catalytic core and binding domains are shown to be expressed using this system.

In the vector, the DNA sequence encoding the truncated cellulase or other novel proteins of the present invention should be operably linked to transcriptional and translational sequences, i.e., a suitable promoter sequence and signal sequence in reading frame to the structural gene. The promoter may be any DNA sequence which shows transcriptional activity in the host cell and may be derived from genes encoding proteins either homologous or heterologous to the host cell. The signal peptide provides for extracellular expression of the truncated cellulase or derivatives thereof. The DNA signal sequence is preferably the signal sequence naturally associated with the truncated gene to be expressed, however the signal sequence from any cellobiohydrolases or endoglucanase is contemplated in the present invention.

The procedures used to ligate the DNA sequences coding for the truncated cellulases, derivatives thereof or other novel cellulases of the present invention with the promoter, and insertion into suitable vectors containing the necessary information for replication in the host cell are well known in the art.

The DNA vector or construct described above may be introduced in the host cell in accordance with known techniques such as transformation, transfection, microinjection, microporation, biolistic bombardment and the like.

In the preferred transformation technique, it must be taken into account that since the permeability of the cell wall in Trichoderma sp. is very low, uptake of the desired DNA sequence, gene or gene fragment is at best minimal. There are a number of methods to increase the permeability of the Trichoderma sp. cell wall in the derivative strain (i.e., lacking a functional gene corresponding to the used selectable marker) prior to the transformation process.

The preferred method in the present invention to prepare Trichoderma sp. for transformation involves the preparation of protoplasts from fungal mycelium. The mycelium can be obtained from germinated vegetative spores. The mycelium is treated with an enzyme which digests the cell wall resulting in protoplasts.

The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8M to 1.2M. It is preferable to use about a 1.2M solution of sorbitol in the suspension medium.

Uptake of the DNA into the host Trichoderma sp. strain is dependent upon the calcium ion concentration. Generally between about 10 Mm $CaCl_2$ and 50 Mm $CaCl_2$ is used in an uptake solution. Besides the need for the calcium ion in the uptake solution, other items generally included are a buffering system such as TE buffer (10 Mm Tris, Ph 7.4; 1 Mm EDTA) or 10 Mm MOPS, Ph 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the Trichoderma sp. strain and the plasmid DNA is transferred to the nucleus. This fusion frequently leaves multiple copies of the plasmid DNA tandemly integrated into the host chromosome.

Usually a suspension containing the Trichoderma sp. protoplasts or cells that have been subjected to a permeability treatment at a density of $10^8$ to $10^9$/ml, preferably $2 \times 10^8$/ml are used in transformation. These protoplasts or cells are added to the uptake solution, along with the desired linearized selectable marker having substantially homologous flanking regions on either side of said marker to form a transformation mixture. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if $Pyr^+$ transformants are being selected it is preferable to use a growth medium that contains no uridine. The subsequent colonies are transferred and purified on a growth medium depleted of uridine.

At this stage, stable transformants were distinguished from unstable transformants by their faster growth rate and the formation of circular colonies with a smooth, rather than ragged outline on solid culture medium lacking uridine. Additionally, in some cases a further test of stability was made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the truncated cellulases or derivatives thereof are recovered in active form from the host cell either as a result of the appropriate post translational processing of the novel truncated cellulase or derivative thereof.

The present invention further relates to DNA gene fragments or variant DNA fragments derived from Trichoderma sp. that code for the truncated cellulase proteins or truncated cellulase protein derivatives, respectively. The DNA gene fragment or variant DNA fragment of the present invention codes for the core or binding domains of a Trichoderma sp. cellulase or derivative thereof that additionally retains the functional activity of the truncated core or binding domain, respectively. Moreover, the DNA fragment or variant thereof comprising the sequence of the core or binding domain regions may additionally have attached thereto a linker, or hinge region DNA sequence or portion thereof wherein the encoded truncated cellulase still retains either cellulase core or binding domain activity, respectively. Furthermore, it is contemplated that additional DNA sequences that encode other proteins or enzymes of interest may be attached to the truncated DNA gene fragment or variant DNA fragment such that by following the above method of construction of vectors and expression of proteins, truncated cellulases or derivatives thereof fused to intact enzymes or proteins may be recovered. The expressed truncated cellulase fused to enzyme or protein would still retain active cellulase binding or core activity, depending on the truncated cellulase chosen to complex with the enzyme/protein.

The use of the cellulose binding domains and cellulase catalytic core domains or derivatives thereof versus using the intact cellulase enzyme may be of benefit in multiple applications. Therefore, a further aspect of the present invention is to provide methods that employ novel truncated cellulases or derivatives of truncated cellulases which provide additional benefits to the applied substrate as compared to intact cellulases. Such applications include stonewashing or biopolishing where it is contemplated that dye/colorant/ pigment backstraining or redeposition can be reduced or eliminated by employing novel truncated cellulase enzymes which have been modified so as to be devoid of a cellulose binding domain or to possess a binding domain with significantly lower affinity for cellulose, for example. In addition, it is contemplated that activity on certain substrates of interest in the textile, detergent, pulp & paper, animal feed, food, biomass industries, for example, can be significantly enhanced or diminished if the binding domain is removed or modified so as to reduce the binding affinity of the enzyme for cellulose. Also, the use of a truncated cellulase or derivative thereof described in the present invention which comprises a functional binding domain fragment, devoid of a catalytic domain or a functioning catalytic domain, may be of benefit in applications where only selected modification of the cellulosic substrate is desired. Properties which could be modified include, for example, hydration, swelling, dye diffusion and uptake, hand, friction, softness, cleaning, and/or surface or structural modification.

It is further contemplated that expression and use of some catalytic domains of cellulase enzymes would provide improved recoverability of enzyme, selectivity where lower activity on more crystalline substrate is desired or selectivity where high activity on amorphous/soluble substrate is desired.

Furthermore, catalytic domains of cellulase enzymes may be useful to enhance synergy with other cellulase components, cellulase or non-cellulase domains, and/or other enzymes or portions thereof on cellulosics cellulose containing materials in applications such as biomass conversion, cleaning, stonewashing, biopolishing of textiles, softening, pulp/paper processing, animal feed utilization, plant protection and pest control, starch processing, or production of pharmaceutical intermediates, disaccharides, or oligosaccharides.

Moreover, uses of cellulase catalytic core domains or derivatives thereof may reduce some of the detrimental properties associated with the intact enzyme on cellulosics such as pulps, cotton or other fibers, or paper. Properties of interest include fiber/fabric strength loss, fiber/fabric weight loss, lint generation, and fibrillation damage.

It is further contemplated that cellulase catalytic core domains may exhibit less fiber roughing or reduced colorant redeposition/backstaining. Furthermore, these truncated catalytic core cellulases or derivatives thereof may offer an option for improved recovery/recycling of these novel cellulases.

Additionally, it is contemplated that the cellulase catalytic core domains or derivatives thereof in the present invention may contain selective activity advantages where hydrolysis of the soluble or more amorphous cellulosic regions of the substrate is desired but hydrolysis of the more crystalline region is not. This may be of importance in applications such as bioconversion where selective modification of the grain/fibers/plant materials is of interest.

Yet another aspect for applying the novel cellulase catalytic core domains or derivatives is in the generation of microcrystalline cellulose (MCC). Furthermore, it is contemplated that the MCC will contain less bound enzyme or that the bound enzyme may be more easibly removed.

It is further contemplated that novel covalently linked truncated cellulase domain derivatives described above may have application in controlling the access of an enzyme or modified enzyme to a substrate. This may include controlling the access of proteases to wool or other materials which contain protease substrates, or controlling the access of cellulose to cellulosics, for example.

Finally, it is contemplated that novel truncated cellulases or derivatives thereof may be applied in unique mono-, dual, or multienzyme systems. As examples this may include linking cellulase domains with each other and/or with one or more protease, cellulase, lipase, and/or amylase enzymes. The enzymes or cellulase domains may be fused with a linker region in between. This linker region may be a peptide of no functional benefit or may contain the cellulose binding domain peptide or a peptide with high affinity for other substrates or substances, such as wool, xylan, mannan, resins, lignins, dyes, colorants, pigments, waxes, plastics, carbohydrate polymers, lipids, amino acid polymers, synthetic polymers, for example.

It is contemplated that novel cellulase domains or derivatives thereof of the present invention may provide some performance properties similar to or in excess of the intact enzyme. The novel truncated cellulases may provide these properties alone or may show synergistic benefits with cellulases or cellulase cores, other enzymes (for example, lipases, proteases, amylases, xylanases, peroxidases, reductases, esterases), other proteins or chemicals. These properties may include roughening or smoothening of the cellulosic surface, modification of the cellulosics for improved response to other enzymes such as in cleaning or pulp processing, animal feed utilization or for improved biochemical/chemical uptake by cellulosics (including plant cell walls).

It is yet further contemplated that truncated cellulase binding domains, derivatives thereof or truncated covalently linked cellulase domain derivatives in the present invention may provide enhanced or synergistic activity on cellulosics with endoglucanases and/or exocellobiohydrolases, modified cellulases or complete cellulase systems. They may also provide adhesive properties in linking cellulosic materials.

Moreover, it is contemplated that novel truncated cellulase binding domains or derivatives or the covalently linked truncated cellulase domain derivatives thereof may find application as new ligands for purification purposes, as reagents or ligands for modification of cellulosics, or other polymers, for example, linking colorants, dyes, inks, finishers, resins, chemicals, biochemicals or proteins to cellulosics. These materials can be removed at any stage, if desired, with proteases or other chemical methods. In addition, it is contemplated that the novel truncated cellulase binding domains or covalently linked truncated cellulose domain derivatives may be used in detection and analysis of trace levels of substances, for example, the truncated domains and derivatives as well as the covalently linked truncated cellulase domain derivatives may contain proteins or chemicals which react with or bind to a substance causing it visualization e.g., dye.

Finally, it is contemplated that novel truncated binding or core domain cellulases or derivatives thereof may be complexed or fused to intact cellulases, other cellulase core or binding domains or other enzymes/proteins to improve stability, or other performance properties such as modification of pH or temperature activity profiles.

All publications and patent applications mentioned in this specification are herein incorporated by reference.

In order to further illustrate the present invention and advantages thereof, the following specific examples are given with the understanding that they are being offered to illustrate the present invention and should not be construed in any way as limiting its scope.

EXAMPLES

Example 1

Preparation of a Uridine Auxotroph Quad Deleted Strain (A) Selection for pyr4 derivatives of *Trichoderma reesei*

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 derivative strains using FOA. In practice, spores of *T. longibrachiatum* strain RL-P37 (Sheir-Neiss, G. and Montenecourt, B. S., *Appl. Microbiol. Biotechnol.* 20, p. 46–53 (1984)) were spread on the surface of a solidified medium containing 2 mg/ml uridine and 1.2 mg/ml FOA. Spontaneous FOA-resistant colonies appeared within three to four days and it was possible to subsequently identify those FOA-resistant derivatives which required uridine for growth. In order to identify those derivatives which specifically had a defective pyr4 gene, protoplasts were generated and transformed with a plasmid containing a wild-type pyr4 gene (see Examples 3 and 4). Following transformation, protoplasts were plated on medium lacking uridine. Subsequent growth of transformed colonies demonstrated complementation of a defective pyr4 gene by the plasmid-borne pyr4 gene. In this way, strain GC69 was identified as a pyr4⁻ derivative of strain RL-P37.

(B) Preparation of CBHI Deletion Vector

A cbh1 gene encoding the CBHI protein was cloned from the genomic DNA of *T. longibrachiatum* strain RL-P37 by hybridization with an oligonucleotide probe designed on the basis of the published sequence for this gene using known probe synthesis methods (Shoemaker et al., 1983b). The cbh1 gene resides on a 6.5 kb PstI fragment and was inserted into PstI cut pUC4K (purchased from Pharmacia Inc., Piscataway, N.J.) replacing the Kan gene of this vector using techniques known in the art, which techniques are set forth in Maniatis et al., (1989) and incorporated herein by reference. The resulting plasmid, pUC4K::cbh1 was then cut with HindIII and the larger fragment of about 6 kb was isolated and relegated to give pUC4K::cbh1ΔH/H (see FIG. 1). This procedure removes the entire cbh1 coding sequence and approximately 1.2 kb upstream and 1.5 kb downstream of flanking sequences. Approximately, 1 kb of flanking DNA from either end of the original PstI fragment remains.

The *T. longibrachiatum* pyr4 gene was cloned as a 6.5 kb HindIII fragment of genomic DNA in pUC18 to form pTpyr2 (Smith et al., 1991) following the methods of Maniatis et al., supra. The plasmid pUC4K::cbhlΔH/H was cut with HindIII and the ends were dephosphorylated with calf intestinal alkaline phosphatase. This end dephosphorylated DNA was ligated with the 6.5 kb HindIII fragment containing the *T. longibrachiatum* pyr4 gene to give pΔCBHIpyr4. FIG. 1 illustrates the construction of this plasmid.

(C) Isolation of Protoplasts

Mycelium was obtained by inoculating 100 ml of YEG (0.5% yeast extract, 2% glucose) in a 500 ml flask with about 5×10⁷ *T. longibrachiatum* GC69 spores (the pyr4⁻ derivative strain). The flask was then incubated at 37° C. with shaking for about 16 hours. The mycelium was harvested by centrifugation at 2,750×g. The harvested mycelium was further washed in a 1.2M sorbitol solution and resuspended in 40 ml of a solution containing 5 mg/ml Novozym® 234 solution (which is the tradename for a multicomponent enzyme system containing 1,3-alpha-glucanase, 1,3-beta-glucanase, laminarinase, xylanase, chitinase and protease from Novo Biolabs, Danbury, Conn.); 5 mg/ml MgSO₄.7H₂O; 0.5 mg/ml bovine serum albumin; 1.2M sorbitol. The protoplasts were removed from the cellular debris by filtration through Miracloth (Calbiochem Corp., La Jolla, Calif.) and collected by centrifugation at 2,000×g. The protoplasts were washed three times in 1.2M sorbitol and once in 1.2M sorbitol, 50 mM CaCl₂, centrifuged and resuspended at a density of approximately 2×10⁸ protoplasts per ml of 1.2M sorbitol, 50 mM CaCl₂.

(D) Transformation of Fungal Protoplasts with pΔCBHIpyr4

200 μl of the protoplast suspension prepared in Example 3 was added to 20 μl of EcoRI digested pΔCBHIpyr4 (prepared in Example 2) in TE buffer (10 mM Tris, pH 7.4; 1 mM EDTA) and 50 μl of a polyethylene glycol (PEG) solution containing 25% PEG 4000, 0.6M KCl and 50 mM CaCl₂. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2M sorbitol and 50 mM CaCl₂ was added thereto and this solution was further mixed. The protoplast solution was then immediately added to molten aliquots of Vogel's Medium N (3 grams sodium citrate, 5 grams KH₂PO₄, 2 grams NH₄NO₃, 0.2 grams MgSO₄.7H₂O, 0.1 gram CaCl₂.2H₂O, 5 μg α-biotin, 5 mg citric acid, 5 mg ZnSO₄.7H₂O, 1 mg Fe(NH₄)₂.6H₂O, 0.25 mg CuSO₄.5H₂O, 50 μg MnSO4.4H₂O per liter) containing an additional 1% glucose, 1.2M sorbitol and 1% agarose. The protoplast/medium mixture was then poured onto a solid medium containing the same Vogel's medium as stated above. No uridine was present in the medium and therefore only transformed colonies were able to grow as a result of complementation of the pyr4 mutation of strain GC69 by the wild type pyr4 gene insert in pACBHIpyr4. These colonies were subsequently transferred and purified on a solid Vogel's medium N containing as an additive, 1% glucose and stable transformants were chosen for further analysis.

At this stage stable transformants were distinguished from unstable transformants by their faster growth rate and formation of circular colonies with a smooth, rather than ragged outline on solid culture medium lacking uridine. In some cases a further test of stability was made by growing the transformants on solid non-selective medium (i.e. containing uridine), harvesting spores from this medium and determining the percentage of these spores which will subsequently germinate and grow on selective medium lacking uridine.

(E) Analysis of the Transformants

DNA was isolated from the transformants obtained in Example 4 after they were grown in liquid Vogel's medium N containing 1% glucose. These transformant DNA samples were further cut with a PstI restriction enzyme and subjected to agarose gel electrophoresis. The gel was then blotted onto a Nytran membrane filter and hybridized with a ³²P labeled pΔCBHIpyr4 probe. The probe was selected to identify the native cbh1 gene as a 6.5 kb PstI fragment, the native pyr4 gene and any DNA sequences derived from the transforming DNA fragment.

The radioactive bands from the hybridization were visualized by autoradiography. The autoradiograph is seen in FIG. 3. Five samples were run as described above, hence samples A, B, C, D, and E. Lane E is the untransformed strain GC69 and was used as a control in the present analysis. Lanes A–D represent transformants obtained by the methods described above. The numbers on the side of the autoradiograph represent the sizes of molecular weight markers. As can be seen from this autoradiograph, lane D does not contain the 6.5 kb CBHI band, indicating that this gene has been totally deleted in the transformant by integration of the DNA fragment at the cbh1 gene. The cbh1 deleted strain is called P37PΔCBHI. FIG. 2 outlines the deletion of the *T. longibrachiatum* cbh1 gene by integration through a double cross-over event of the larger EcoRI fragment from pΔCBHIpyr4 at the cbh1 locus on one of the *T. longibrachiatum* chromosomes. The other transformants analyzed appear identical to the untransformed control strain.

(F) Analysis of the Transformants with pIntCBHI

The same procedure was used in this example as in Example 5, except that the probe used was changed to a $^{32}$P labeled pIntCBHI probe. This probe is a pUC-type plasmid containing a 2 kb BgIII fragment from the cbh1 locus within the region that was deleted in pUC4K::cbh1ΔH/H. Two samples were run in this example including a control, sample A, which is the untransformed strain GC69 and the transformant P37PΔCBHI, sample B. As can be seen in FIG. 4, sample A contained the cbh1 gene, as indicated by the band at 6.5 kb; however the transformant, sample B, does not contain this 6.5 kb band and therefore does not contain the cbh1 gene and does not contain any sequences derived from the pUC plasmid.

(G) Protein Secretion by Strain P37PΔCBHI

Spores from the produced P37PΔCBHI strain were inoculated into 50 ml of a Trichoderma basal medium containing 1% glucose, 0.14% $(NH_4)_2SO_4$, 0.2% $KH_2PO_4$, 0.03% $MgSO_4$, 0.03% urea, 0.75% bactotryptone, 0.05% Tween 80, 0.000016% $CuSO_4.5H_2O$, 0.001% $FeSO_4.7H_2O$, 0.000128% $ZnSO_4.7H_2O$, 0.0000054% $Na_2MoO_4.2H_2O$, 0.0000007% $MnCl.4H_2O$). The medium was incubated with shaking in a 250 ml flask at 37° C. for about 48 hours. The resulting mycelium was collected by filtering through Miracloth (Calbiochem Corp.) and washed two or three times with 17 mM potassium phosphate. The mycelium was finally suspended in 17 mM potassium phosphate with 1 mM sophorose and further incubated for 24 hours at 30° C. with shaking. The supernatant was then collected from these cultures and the mycelium was discarded. Samples of the culture supernatant were analyzed by isoelectric focusing using a Pharmacia Phastgel system and pH 3–9 precast gels according to the manufacturer's instructions. The gel was stained with silver stain to visualize the protein bands. The band corresponding to the cbh1 protein was absent from the sample derived from the strain P37PΔCBHI, as shown in FIG. 5. This isoelectric focusing gel shows various proteins in different supernatant cultures of *T. longibrachiatum*. Lane A is partially purified CBHI; Lane B is the supernatant from an untransformed *T. longibrachiatum* culture; Lane C is the supernatant from strain P37PΔCBHI produced according to the methods of the present invention. The position of various cellulase components are labeled CBHI, CBHII, EGI, EGII, and EGIII. Since CBHI constitutes 50% of the total extracellular protein, it is the major secreted protein and hence is the darkest band on the gel. This isoelectric focusing gel clearly shows depletion of the CBHI protein in the P37PΔCBHI strain.

(H) Preparation of pPΔCBHII

The cbh2 gene of *T. longibrachiatum*, encoding the CBHII protein, has been cloned as a 4.1 kb EcoRI fragment of genomic DNA which is shown diagrammatically in FIG. 6A (Chen et al., 1987, *Biotechnology*, 5:274–278). This 4.1 kb fragment was inserted between the EcoRI sites of pUC4XL. The latter plasmid is a pUC derivative (constructed by R. M. Berka, Genencor International Inc.) which contains a multiple cloning site with a symmetrical pattern of restriction endonuclease sites arranged in the order shown here: EcoRI, BamHI, SacI, SmaI, HindIII, XhoI, BgIII, ClaI, BgIII, XhoI, HindIII, SmaI, SacI, BamHI, EcoRI. Using methods known in the art, a plasmid, pPΔCBHII (FIG. 6B), has been constructed in which a 1.7 kb central region of this gene between a HindIII sit (at 74 bp 3') of the CBHII translation initiation site) and a ClaI site (at 265 bp 3' of the last codon of CBHII) has been removed and replaced by a 1.6 kb HindIII-ClaI DNA fragment containing the *T. longibrachiatum* pyr4 gene.

The *T. longibrachiatum* pyr4 gene was excised from pTpyr2 (see Example 2) on a 1.6 kb NheI-SphI fragment and inserted between the SphI and XbaI sites of pUC219 (see Example 16) to create p219M (Smith et al., 1991, *Curr. Genet* 19 p. 27–33). The pyr4 gene was then removed as a HindIII-ClaI fragment having seven bp of DNA at one end and six bp of DNA at the other end derived from the pUC219 multiple cloning site and inserted into the HindIII and ClaI sites of the cbh2 gene to form the plasmid pPΔCBHII (see FIG. 6B).

Digestion of this plasmid with EcoRI will liberate a fragment having 0.7 kb of flanking DNA from the cbh2 locus at one end, 1.7 kb of flanking DNA from the cbh2 locus at the other end and the *T. longibrachiatum* pyr4 gene in the middle.

(I) Deletion of the cbh2 gene in *T. longibrachiatum* strain GC69

Protoplasts of strain CG69 will be generated and transformed with EcoRI digested pPΔCBHII according to the methods outlined in Examples 3 and 4. DNA from the transformants will be digested with EcoRI and Asp718, and subjected to agarose gel electrophoresis. The DNA from the gel will be blotted to a membrane filter and hybridized with $^{32}$P labeled pPΔCBHII according to the methods in Example 11. Transformants will be identified which have a single copy of the EcoRI fragment from pPΔCBHII integrated precisely at the cbh2 locus. The transformants will also be grown in shaker flasks as in Example 7 and the protein in the culture supernatants examined by isoelectric focusing. In this manner *T. longibrachiatum* GC69 transformants which do not produce the CBHII protein will be generated.

(J) Generation of a pyr4⁻ Derivative of P37PΔCBHI

Spores of the transformant (P37PΔCBHI) which was deleted for the cbh1 gene were spread onto medium containing FOA. A pyr4⁻ derivative of this transformant was subsequently obtained using the methods of Example 1. This pyr4⁻ strain was designated P37PΔCBHIPyr⁻26.

(K) Deletion of the cbh2 gene in a strain previously deleted for cbh1

Protoplasts of strain P37PΔCBHIPyr⁻26 were generated and transformed with EcoRI digested pPΔCBHII according to the methods outlined in Examples 3 and 4.

Purified stable transformants were cultured in shaker flasks as in Example 7 and the protein in the culture supernatants was examined by isoelectric focusing. One transformant (designated P37PΔΔCBH67) was identified which did not produce any CBHII protein. Lane D of FIG. 5 shows the supernatant from a transformant deleted for both the cbh1 and cbh2 genes produced according to the methods of the present invention.

DNA was extracted from strain P37PΔΔCBH67, digested with EcoRI and Asp718, and subjected to agarose gel electrophoresis. The DNA from this gel was blotted to a membrane filter and hybridized with $^{32}$P labeled pPΔCBHII (FIG. 7). Lane A of FIG. 7 shows the hybridization pattern observed for DNA from an untransformed *T. longibrachiatum* strain. The 4.1 kb EcoRI fragment containing the wild-type cbh2 gene was observed. Lane B shows the hybridization pattern observed for strain P37PΔΔCBH67. The single 4.1 kb band has been eliminated and replaced by two bands of approximately 0.9 and 3.1 kb. This is the expected pattern if a single copy of the EcoRI fragment from pPΔCBHII had integrated precisely at the cbh2 locus.

The same DNA sample were also digested with EcoRI and Southern blot analysis was performed as above. In this Example, the probe was $^{32}$P labeled pIntCBHII. This plasmid contains a portion of the cbh2 gene coding sequence from within that segment of the cbh2 gene which was deleted in plasmid pPΔCBHII. No hybridization was seen with DNA from strain P37PΔΔCBH67 showing that the cbh2 gene was deleted and that no sequences derived from the pUC plasmid were present in this strain.

(L) Construction of pEGIpyr4

*T. longibrachiatum* egI1 gene, which encodes EGI, has been cloned as a 4.2 kb HindIII fragment of genomic DNA from strain RL-P37 by hybridization with oligonucleotides synthesized according to the published sequence (Penttila et al., 1986, Gene 45:253–263; van Arsdell et al., 1987, *Bio/Technology* 5:60–64). A 3.6 kb HindIII-BamHI fragment was taken from this clone and ligated with a 1.6 kb HindIII-BamHI fragment containing the *T. longibrachiatum* pyr4 gene obtained from pTpyr2 (see Example 2) and pUC218 (identical to pUC219, see Example 16, but with the multiple cloning site in the opposite orientation) cut with HindIII to give the plasmid pEGIpyr4 (FIG. 8). Digestion of pEGIpyr4 with HindIII would liberate a fragment of DNA containing only *T. longibrachiatum* genomic DNA (the egI1 and pyr4 genes) except for 24 bp of sequenced, synthetic DNA between the two genes and 6 bp of sequenced, synthetic DNA at one end (see FIG. 8).

(M) Transformants of *Trichoderma reesei* Containing the plasmid pEGIpyr4

A pyr4 defective derivative of *T. longibrachiatum* strain RutC30 (Sheir-Neiss and Montenecourt, (1984), *Appl. Microbiol. Biotechnol.* 20:46–53) was obtained by the method outlined in Example 1. Protoplasts of this strain were transformed by the methods of Examples 3 and 4 with undigested pEGIpyr4 and stable transformants were purified.

Five of these transformants (designated EP2, EP4, EP5, EP6, EP11), as well as untransformed RutC30 were inoculated into 50 ml of YEG medium (yeast extract, 5 g/l; glucose, 20 g/l) in 250 ml shake flasks and cultured with shaking for two days at 28° C. The resulting mycelium was washed with sterile water and added to 50 ml of TSF medium (0.05M citrate-phosphate buffer, pH 5.0; Avicel microcrystalline cellulose, 10 g/l; KH$_2$PO$_4$, 2.0 g/l; (NH$_4$)$_2$SO$_4$, 1.4 g/l; proteose peptone, 1.0 g/l; Urea, 0.3 g/l; MgSO$_4$.7H$_2$O, 0.3 g/l; CaCl$_2$, 0.3 g/l; FeSO$_4$.7H$_2$O, 5.0 mg/l; MnSO$_4$.H$_2$O, 1.6 mg/l; ZnSO$_4$, 1.4 mg/l; CoCl$_2$, 2.0 mg/l; 0.1% Tween 80). These cultures were incubated with shaking for a further four days at 28° C. Samples of the supernatant were taken from these cultures an assays designed to measure the total amount of protein and of endoglucanase activity were performed as described below.

The endoglucanase assay relied on the release of soluble, dyed oligosaccharides from Remazol Brilliant Blue-carboxymethylcellulose (RBB-CMC, obtained from MegaZyme, North Rocks, NSW, Australia). The substrate was prepared by adding 2 g of dry RBB-CMC to 80 ml of just boiled deionized water with vigorous stirring. When cooled to room temperature, 5 ml of 2M sodium acetate buffer (pH 4.8) was added and the pH adjusted to 4.5. The volume was finally adjusted to 100 ml with deionized water and sodium azide added to a final concentration of 0.02%. Aliquots of *T. longibrachiatum* control culture, pEGIpyr4 transformant culture supernatant or 0.1M sodium acetate as a blank (10–20 μl) were placed in tubes, 250 μl of substrate was added and the tubes were incubated for 30 minutes at 37° C. The tubes were placed on ice for 10 minutes and 1 ml of cold precipitant (3.3% sodium acetate, 0.4% zinc acetate, pH 5 with HCl, 76% ethanol) was then added. The tubes were vortexed and allowed to sit for five minutes before centrifuging for three minutes at approximately 13,000×g. The optical density was measured spectrophotometrically at a wavelength of 590–600 nm.

The protein assay used was the BCA (bicinchoninic acid) assay using reagents obtained from Pierce, Rockford, Ill., U.S.A. The standard was bovine serum albumin (BSA). BCA reagent was made by mixing 1 part of reagent B with 50 parts of reagent A. One ml of the BCA reagent was mixed with 50 μl of appropriately diluted BSA or test culture supernatant. Incubation was for 30 minutes at 37° C. and the optical density was finally measured spectrophotometrically at a wavelength of 562 nm.

The results of the assays described above are shown in Table 1. It is clear that some of the transformants produced increased amounts of endoglucanase activity compared to untransformed strain RutC30. It is thought that the endoglucanases and exo-cellobiohydrolases produced by untransformed *T. longibrachiatum* constitute approximately 20 and 70 percent respectively of the total amount of protein secreted. Therefore a transformant such as EP5, which produces approximately four-fold more endoglucanase than strain RutC30, would be expected to secrete approximately equal amounts of endoglucanase-type and exo-cellobiohydrolase-type proteins.

The transformants described in this Example were obtained using intact pEGIpyr4 and will contain DNA sequences integrated in the genome which were derived from the pUC plasmid. Prior to transformation it would be possible to digest pEGIpyr4 with HindIII and isolate the larger DNA fragment containing only *T. longibrachiatum* DNA. Transformation of *T. longibrachiatum* with this isolated fragment of DNA would allow isolation of transformants which overproduced EGI and contained no heterologous DNA sequences except for the two short pieces of synthetic DNA shown in FIG. 8. It would also be possible to use pEGIpyr4 to transform a strain which was deleted for either the cbh1 gene, or the cbh2 gene, or for both genes. In this way a strain could be constructed which would overproduce EGI and produce either a limited range of, or no, exo-cellobiohydrolases.

The methods of Example 13 could be used to produce *T. longibrachiatum* strains which would over-produce any of the other cellulase components, xylanase components or other proteins normally produced by *T. longibrachiatum*.

TABLE 1

Secreted Endoglucanase Activity of
*T. longibrachiatum* Transformants

| STRAIN | A<br>ENDOGLUCANASE<br>ACTIVITY<br>(O.D. AT 590 nm) | B<br>PROTEIN<br>(mg/ml) | A/B |
|---|---|---|---|
| RutC30 | 0.32 | 4.1 | 0.078 |
| EP2 | 0.70 | 3.7 | 0.189 |
| EP4 | 0.76 | 3.65 | 0.208 |
| EP5 | 1.24 | 4.1 | 0.302 |
| EP6 | 0.52 | 2.93 | 0.177 |
| EP11 | 0.99 | 4.11 | 0.241 |

The above results are presented for the purpose of demonstrating the overproduction of the EGI component relative to total protein and not for the purpose of demonstrating the extent of overproduction. In this regard, the extent of overproduction is expected to vary with each experiment.

(N) Construction of pEGII::P-1

The egl3 gene, encoding EGII (previously referred to as EGIII by others), has been cloned from *T. longibrachiatum* and the DNA sequence published (Saloheimo et al., 1988, Gene 63:11–21). We have obtained the gene from strain RL-P37 as an approximately 4 kb PstI-XhoI fragment of genomic DNA inserted between the PstI and XhoI sites of pUC219. The latter vector, pUC219, is derived from pUC119 (described in Wilson et al., 1989, Gene 77:69–78) by expanding the multiple cloning site to include restriction sites for BglII, ClaI and XhoI. Using methods known in the art the *T. longibrachiatum* pyr4 gene, present on a 2.7 kb SalI fragment of genomic DNA, was inserted into a SalI site within the EGII coding sequence to create plasmid pEGII::P-1 (FIG. 12). This resulted in disruption of the EGII coding sequence but without deletion of any sequences. The plasmid, pEGII::P-1 can be digested with HindIII and BamHI to yield a linear fragment of DNA derived exclusively from *T. longibrachiatum* except for 5 bp on one end and 16 bp on the other end, both of which are derived from the multiple cloning site of pUC219.

(O) Transformation of *T. longibrachiatum* GC69 with pEGII::P-1 to create a strain unable to produce EGII

*T. longibrachiatum* strain GC69 will be transformed with pEGII::P-1 which had been previously digested with HindIII and BamHI and stable transformants will be selected. Total DNA will be isolated from the transformants and Southern blot analysis used to identify those transformants in which the fragment of DNA containing the pyr4 and egl3 genes had integrated at the egl3 locus and consequently disrupted the EGII coding sequence. The transformants will be unable to produce EGII. It would also be possible to use pEGII::P-1 to transform a strain which was deleted for either or all of the cbh1, cbh2, or egl1 genes. In this way a strain could be constructed which would only produce certain cellulase components and no EGII component.

(P) Transformation of *T. longibrachiatum* with pEGII::P-1 to create a strain unable to produce CBHI, CBHII and EGII A pyr4 deficient derivative of strain P37PΔΔCBH67 (from Example 11) was obtained by the method outlined in Example 1. This strain P37PΔΔ67P$^-$1 was transformed with pEGII::P-1 which had been previously digested with HindIII and BamHI and stable transformants were selected. Total DNA was isolated from transformants and Southern blot analysis used to identify strains in which the fragment of DNA containing the pyr4 and egl3 genes had integrated at the egl3 locus and consequently disrupted the EGII coding sequence. The Southern blot illustrated in FIG. 13 was probed with an approximately 4 kb PstI fragment of *T. longibrachiatum* DNA containing the egl3 gene which had been cloned into the PstI site of pUC18 and subsequently re-isolated. When the DNA isolated from strain P37PΔΔ67P$^-$1 was digested with PstI for Southern blot analysis the egl3 locus was subsequently visualized as a single 4 kb band on the autoradiograph (FIG. 13, lane E). However, for a transformant disrupted for the egl3 gene this band was lost and was replaced by two new bands as expected (FIG. 13, Lane F). If the DNA was digested with EcoRV or BglII the size of the band corresponding to the egl3 gene increased in size by approximately 2.7 kb (the size of the inserted pyr4 fragment) between the untransformed P37PΔΔ67P$^-$1 strain (Lanes A and C) and the transformant disrupted for egl3 (FIG. 13, Lanes B and D). The transformant containing the disrupted egl3 gene illustrated in FIG. 13 (Lanes B, D and F) was named A22. The transformant identified in FIG. 13 is unable to produce CBHI, CBHII or EGII. A second transformant, labeled B31, which is unable to produce CBHI, CBHII, and EGII, was also identified by this method. Further Southern Blot analysis confirmed that the pUC DNA fragment of pEGII:P-1 was not incorporated into the transformant strain B31.

(Q) Construction of pPΔEGI-1

The egl1 gene of *T. longibrachiatum* strain RL-P37 was obtained, as described in Example 12, as a 4.2 kb HindIII fragment of genomic DNA. This fragment was inserted at the HindIII site of pUC100 (a derivative of pUC18; Yanisch-Perron et al., 1985, Gene 33:103–119, with an oligonucleotide inserted into the multiple cloning site adding restriction sites for BglII, ClaI and XhoI). Using methodology known in the art an approximately 1 kb EcoRV fragment extending from a position close to the middle of the EGI coding sequence to a position beyond the 3' end of the coding sequence was removed and replaced by a 3.5 kb ScaI fragment of *T. longibrachiatum* DNA containing the pyr4 gene. The resulting plasmid was called pPΔEGI-1 (see FIG. 14).

The plasmid pPΔEGI-1 can be digested with HindIII to release a DNA fragment comprising only *T. longibrachiatum* genomic DNA having a segment of the egl1 gene at either end and the pyr4 gene replacing part of the EGI coding sequence, in the center.

Transformation of a suitable *T. longibrachiatum* pyr4 deficient strain with the pPΔEGI-1 digested with HindIII will lead to integration of this DNA fragment at the egl1 locus in some proportion of the transformants. In this manner a strain unable to produce EGI will be obtained.

(R) Construction of PΔEGIpyr-3 and Transformation of a pyr4 deficient strain of *T. longibrachiatum*

The expectation that the EGI gene could be inactivated using the method outlined in Example 21 is strengthened by this experiment. In this case a plasmid, pΔEGIpyr-3, was constructed which was similar to pPΔEGI-1 except that the *Aspergillus niger* pyr4 gene replaced the *T. longibrachiatum* pyr4 gene as selectable marker. In this case the egl1 gene was again present as a 4.2 kb HindIII fragment inserted at the HindIII site of pUC100. The same internal 1 kb EcoRV fragment was removed as during the construction of pPΔEGI-1 (see Example 21) but in this case it was replaced by a 2.2 kb fragment containing the cloned *A. niger* pyrG gene (Wilson et al., 1988, *Nucl. Acids Res.* 16 p.2339). Transformation of a pyr4 deficient strain of *T. longibrachiatum* (strain GC69) with pΔEGIpyr-3, after it had been digested with HindIII to release the fragment containing the pyrG gene with flanking regions from the egl1 locus at either end, led to transformants in which the egI1 gene was disrupted. These transformants were recognized by Southern blot analysis of transformant DNA digested with HindIII and probed with radiolabelled pΔEGIpyr-3. In the untransformed strain of *T. longibrachiatum* the egI1 gene was present on a 4.2 kb HindIII fragment of DNA and this pattern of hybridization is represented by FIG. 15, lane C. However, following deletion of the egI1 gene by integration of the desired fragment from pΔEGIpyr-3 this 4.2 kb fragment disappeared and was replaced by a fragment approximately 1.2 kb larger in size, FIG. 15, lane A. Also shown in FIG. 15, lane B is an example of a transformant in which integration of a single copy of pPΔEGIpyr-3 has occurred at a site in the genome other than the egI1 locus.

(S) Transformation of Quad Deleted Uridine Auxotroph *T. longibrachiatum* with pPΔEGI-1 to create a strain unable to produce CBHI, CBHII, EGI and EGII A pyr4 deficient derivative of strain A22 (from Example 20) will be obtained by the method outlined in Example 1. This strain will be transformed with pPΔEGI-1 which had been previously digested with HindIII to release a DNA fragment comprising only *T. longibrachiatum* genomic DNA having a segment of the egI1 gene at either end with part of the EGI coding sequence replaced by the pyr4 gene.

Stable pyr4+ transformants will be selected and total DNA isolated from the transformants. The DNA will be probed with $^{32}$P labeled pPΔEGI-1 after Southern blot analysis in order to identify transformants in which the fragment of DNA containing the pyr4 gene and egI1 sequences has integrated at the egI1 locus and consequently disrupted the EGI coding sequence. The transformants identified will be unable to produce CBHI, CBHII, EGI and EGII and are referred to as 1A52 pyr13.

Example 2

Cloning and Expression of EG1 Core Domain Using its Own Promoter, Terminator and Signal Sequence Part 1. Cloning The complete egI1 gene used in the construction of the EGI core domain expression plasmid, PEG1Δ3'pyr, was obtained from the plasmid PUC218::EG1. (See FIG.6.) The 3' terminator region of egI1 was ligated into PUC218 (Korman, D. et al Curr Genet 17:203–212, 1990) as a 300 bp BsmI-EcoRI fragment along with a synthetic linker designed to replace the 3' intron and cellulose binding domain with a stop codon and continue with the egI1 terminator sequences. The resultant plasmid, PEG1T, was digested with HindIII and BsmI and the vector fragment was isolated from the digest by agarose gel electrophoresis followed by electroelution. The egI1 gene promoter sequence and core domain of egI1 were isolated from PUC218::EG1 as a 2.3 kb HindIII-SstI fragment and ligated with the same synthetic linker fragment and the HindIII-BsmI digested PEG1T to form PEG1Δ3'

The net result of these operations is to replace the 3' intron and cellulose binding domain of egI1 with synthetic oligonucleotides of 53 and 55bp. These place a TAG stop codon after serine 415 and thereafter continued with the egI1 terminator up to the BsmI site.

Next, the *T. longibrachiatum* selectable marker, pyr4, was obtained from a previous clone p219M (Smith et al 1991), as an isolated 1.6 kb EcoRI-HindIII fragment. This was incorporated into the final expression plasmid, PEG1Δ3'pyr, in a three way ligation with PUC18 plasmid digested with EcoRI and dephosphorylated using calf alkaline phosphatase and a HindIII-EcoRI fragment containing the egI1 core domain from PEG1Δ3'.

Part 2. Transformation and Expression

A large scale DNA prep was made of PEG1Δ3'pyr and from this the EcoRI fragment containing the egI1 core domain and pyr4 gene was isolated by preparative gel electrophoresis. The isolated fragment was transformed into the uridine auxotroph version of the quad deleted strain, 1A52 pyr13 and stable transformants were identified.

To select which transformants expressed egI1 core domain the transformants were grown up in shake flasks under conditions that favored induction of the cellulase genes (Vogels+1% lactose). After 4–5 days of growth, protein from the supernatants was concentrated and either 1) run on SDS polyacrylamide gels prior to detection of the egI1 core domain by Western analysis using EGI polyclonal antibodies or 2) the concentrated supernatants were assayed directly using RBB carboxy methyl cellulose as an endoglucanase specific substrate and the results compared to the parental strain 1A52 as a control. Transformant candidates were identified as possibly producing a truncated EGI core domain protein. Genomic DNA and total MRNA was isolated from these strains following growth on Vogels+1% lactose and Southern and Northern blot experiments performed using an isolated DNA fragment containing only the egI1 core domain. These experiments demonstrated that transformants could be isolated having a copy of the egI1 core domain expression cassette integrated into the genome of 1A52 and that these same transformants produced egI1 core domain MRNA.

One transformant was then grown using media suitable for cellulase production in Trichoderma well known in the art that was supplemented with lactose (Warzymoda, M. et al 1984 French Patent No. 2555603) in a 14 L fermentor. The resultant broth was concentrated and the proteins contained therein were separated by SDS polyacrylamide gel electrophoresis and the EgI1 core domain protein identified by Western analysis. (See Example 3 below). It was subsequently estimated that the protein concentration of the fermentation supernatant was about 5–6 g/L of which approximately 1.7–4.4 g/L was EGI core domain based on CMCase activity. This value is based on an average of several EGI core fermentations that were performed.

In a similar manner, any other cellulase domain or derivative thereof may be produced by procedures similar to those discussed above.

Example 3

Purification of EGI and EGII catalytic cores

Part 1. EGI catalytic core

The EGI core was purified in the following manner. The concentrated (UF) broth was filtered using diatomaceous earth and ammonium sulfate was added to the broth to a final concentration of 1M (NH4)2SO4. This was then loaded onto a hydrophobic column (phenyl-sepharose fast flow, Pharmacia, cat # 17-0965-02) and eluted with a salt gradient from 1M to OM (NH4)$_2$SO4. The fractions which contained the EGI core were then pooled and exchanged into 10 mM TES pH 7.5. This solution was then loaded onto an anion exchange column (Q-sepharose fast flow, Pharmacia Cat # 17-0510-01) and eluted in a gradient from 0 to 1M NaCl in 10 mM TES pH 7.5. The most pure fractions were desalted into 10 mM TES pH 7.5 and loaded onto a MONO Q column. The EGI core elution was carried out with a gradient from 0 to 1M NaCl. The resulting fractions were greater than 85% pure. The most pure fraction was sequence verified to be the EGI core.

Part 2. EGII catalytic core

It is contemplated that the purification of the EGII catalytic core is similar to that of EGII cellulase because of its similar biochemical properties. The theoretical pI of the EGII core is less than a half a pH unit lower than that of EGII. Also, EGII core is approximately 80% of the molecular weight of EGII. Therefore, the following purification protocol is based on the purification of EGII. The method may involve filtering the UF concentrated broth through diatomaceous earth and adding (NH4)2S04 to bring the solution to 1M (NH4)2S04. This solution may then be loaded onto a hydrophobic column (phenyl-sepharose fast flow, Pharmacia, cat #17-0965-02) and the EGII may be step eluted with 0.15M (NH4)2S04. The fractions containing the EGII core may then be buffer exchanged into citrate-phosphate pH 7, 0.18 mOhm. This material may then be loaded onto a anion exchange column (Q-sepharose fast flow, Pharmacia, cat. #17-0510-01) equilibrated in the above citrate-phosphate buffer. It is expected that EGII core will not bind to the column and thus be collected in the flow through.

Example 4

Cloning and Expression of CBHII Core Domain Using the CBHI Promoter, Terminator and Signal Sequence from CBHII Part 1. Construction of the *T. longibrachiatum* general-purpose expression plasmid-PTEX The plasmid, PTEX was constructed following the methods of Sambrook et al. (1989), supra, and is illustrated in FIG. 7. This plasmid has been designed as a multi-purpose expression vector for use in the filamentous fungus *Trichoderma longibrachiatum*. The expression cassette has several unique features that make it useful for this function. Transcription is regulated using the strong CBH I gene promoter and terminator sequences for *T. longibrachiatum*. Between the CBHI promoter and terminator there are unique PmeI and SstI restriction sites that are used to insert the gene to be expressed. The *T. longibrachiatum* pyr4 selectable marker gene has been inserted into the CBHI terminator and the whole expression cassette (CBHI promoter-insertion sites-CBHI terminator-pyr4 gene-CBHI terminator) can be excised utilizing the unique NotI restriction site or the unique NotI and NheI restriction sites.

This vector is based on the bacterial vector, pSL1180 (Pharmacia Inc., Piscataway, N.J.), which is a PUC-type vector with an extended multiple cloning site. One skilled in the art would be able to construct this vector based on the flow diagram illustrated in FIG. 7.

It would be possible to construct plasmids similar to PTEX-truncated cellulases or derivatives thereof described in the present invention containing any other piece of DNA sequence replacing the truncated cellulase gene.

Part 2. Cloning

The complete cbh2 gene used in the construction of the CBHII core domain expression plasmid, PTEX CBHII core, was obtained from the plasmid PUC219::CBHII (Korman, D. et al, 1990, Curr Genet 17:203–212). The cellulose binding domain, positioned at the 5' end of the cbh2 gene, is conveniently located between an XbaI and SnaBI restriction sites. In order to utilize the XbaI site an additional XbaI site in the polylinker was destroyed. PUC219::CBHII was partially digested with XbaI such that the majority of the product was linear. The XbaI overhangs were filled in using T4 DNA polymerase and ligated together under conditions favoring self ligation of the plasmid. This has the effect of destroying the blunted site which, in 50% of the plasmids, was the XbaI site in the polylinker. Such a plasmid was identified and digested with XbaI and SnaBI to release the cellulose binding domain. The vector-CBHII core domain was isolated and ligated with the following synthetic oligonucleotides designed to join the XbaI site with the SnaBI site at the signal peptidase cleavage site and papain cleavage point in the linker domain.

```
    XbaI                                        SnaBI
5'  CTA   GAG CGG TCG GGA ACC GCT AC    3' (Seq ID No: 44)
3'        TC CTC GCC AGC CCT TGG CGA TG  5'
    Leu Glu Glu Arg Ser Gly Thr Ala Thr      (Seq ID No: 45)
```

The resultant plasmid, pUCΔCBD CBHII, was digested with NheI and the ends blunted by incubation with T4 DNA polymerase and dNTPs. After which the linear blunted plasmid DNA was digested with BglII and the Nhe (blunt) BglII fragment containing the CBHII signal sequence and core domain was isolated.

The final expression plasmid was engineered by digesting the general purpose expression plasmid, pTEX, with SstII and PmeI and ligating the CBHII NheI (blunt)-BglII fragment downstream of the cbh1 promoter using a synthetic oligonucleotide having the sequence CGCTAG to fill in the BglII overhang with the SstII overhang.

The pTEX-CBHI core expression plasmid was prepared in a similar manner as pTEX-CBHII core described in the above example. Its construction is exemplified in FIG. 8.

Part 3. Transformation and Expression

A large scale DNA prep was made of pTEX CBHIIcore and from this the NotI fragment containing the CBHII core domain under the control of the cbh1 transcriptional elements and pyr4 gene was isolated by preparative gel electrophoresis. The isolated fragment was transformed into the uridine auxotroph version of the quad deleted strain, 1A52 pyr13, and stable transformants were identified.

To select which transformants expressed cbh2 core domain genomic DNA was isolated from strains following growth on Vogels+1% glucose and Southern blot experiments performed using an isolated DNA fragment containing only the cbh2 core domain. Transformants were isolated having a copy of the cbh2 core domain expression cassette integrated into the genome of 1A52. Total mRNA was isolated from the two strains following growth for 1 day on Vogels+1% lactose. The MRNA was subjected to Northern analysis using the cbh2 coding region as a probe. Transformants expressing cbh2 core domain MRNA were identified.

Two transformants were grown under the same conditions as previously described in Example 1 in 14 L fermentors. The resultant broth was concentrated and the proteins contained therein were separated by SDS polyacrylamide gel electrophoresis and the CBHII core domain protein identified by Western analysis. One transformant, # 15, produced a protein of the correct size and reactivity to CBHII polyclonal antibodies.

It was subsequently estimated that the protein concentration of the fermentation supernatant after purification was 10 g/L of which 30–50% was CBHII core domain (See Example 4).

One may obtain any other novel truncated cellulase-core domain protein or derivative thereof by employing the methods described above.

Example 5

Purification of CBHI and CBHII catalytic cores

Part 1. CBHI catalytic core

The CBHI core was purified from broth obtained from *T. longibrachiatum* harboring pTEX-CBHI core expression vector in the following manner. The CBHI core ultrafiltered (UF) broth was filtered using diatomaceous earth and diluted in 10 mM TES pH 6.8 to a conductivity of 1.5 mOhm. The diluted CBHI core was then loaded onto an anion exchange column (Q-Sepharose fast flow, Pharmacia cat # 17-0510-01) equilibrated in 10 mM TES pH 6.8 The CBHI core was separated from the majority of the other proteins in the broth using a gradient elution in 10 mM TES pH 6.8 from 0 to 1M NaCl. The fractions containing the CBHI core were then concentrated on an Amicon stirred cell concentrator with a PM 10 membrane (diaflo ultra filtration membranes, Amicon Cat # 13132MEM 5468A). This step concentrated the core as well as separated it from lower molecular weight proteins.

```
5' TAT TAC TAA 3'
3' ACGT ATA ATG ATT 5'
  NsiI            *** *** Stop codons
```

When the final expression plasmid, pTEX CBHII CBD, was sequenced across the linker junctions it was discovered that the sticky NsiI site had ligated directly to the blunt PmeI site in pTEX. This means that the reading frame of the CBHII CBD continues on through the PmeI linker and into the cbh1 terminator for a further 12 amino acids as follows;

```
5' AAA CCC CGG GTG ATT TAT TTT TTT TGT ATC TAC TTC TGA 3'
3' TTT GGG GCC CAC TAA ATA AAA AAA ACA TAG ATG AAG ACT 5'
                                                    (Seq ID No: 46)
Lys Pro Arg Val Ile Tyr Phe Phe Cys Ile Tyr Phe
                                                    (Seq ID No: 47)
```

The resulting fractions were greater than 85% pure CBHI core. The purest fraction was sequence verified to be the CBHI core.

Part 2. CBHII catalytic core sIt is predicted that CBHII catalytic core will purify in a manner similar to that of CBHII cellulase because of its similar biochemical properties. The theoretical pI of the CBHII core is less than half a pH unit lower than that of CBHII. Additionally, CBHII catalytic core is approximately 80% of the molecular weight of CBHII. Therefore, the following proposed purification protocol is based on the purification method used for CBHII. The diatomaceous earth treated, ultra filtered (UF) CBHII core broth is diluted into 10 mM TES pH 6.8 to a conductivity of <0.7 mOhm. The diluted CBHII core is then loaded onto an anion exchange column (Q-Sepharose fast flow, Pharmacia, cat # 17 0510-01) equilibrated in 10 mM TES pH 6.8. A salt gradient from 0 to 1M NaCl in 10 mM TES pH 6.8 is used to elute the CBHII core off the column. The fractions which contain the CBHII core is then buffer exchanged into 2 mM sodium succinate buffer and loaded onto a cation exchange column (SP-sephadex C-50). The CBHII core is next eluted from the column with a salt gradient from 0 to 100 mM NaCl.

Example 6

Cloning and Expression of CBHII Cellulose Binding Domain Using the CBHI Promoter Part 1. Cloning The complete cbh2 gene used in the construction of the CBHII core domain expression plasmid, pTEX CBHIIcore, was obtained from the plasmid pUC219::CBHII. The cellulose binding domain, positioned at the 5' end of the cbh2 gene, was obtained by digestion of PUC219::CBHII with BglII and NsiI and isolating the 450 bp BglII-NsiI restriction fragment. The final expression plasmid, PTEX CBHII CBD was engineered by digesting the general purpose expression plasmid, PTEX, with SstII and PmeI and ligating the CBHII CBD BglII-NsiI fragment downstream of the cbh1 promoter using a synthetic oligonucleotide having the sequence 3' CGCTAG 5' to fill in the BglII overhang with the SstII overhang and the following synthetic linker to link the NsiI site with the blunt PmeI site of pTEX. (See FIG. 9).

However, the addition of these additional amino acids is not thought to significantly change the properties of the cellulose binding domain.

In a similar fashion, it is contemplated that any one of the other known binding domains may be substituted in the above pTEX construct to provide expression of the substituted binding domains by following the general format disclosed above.

Part 2. Transformation and Expression

A large scale DNA prep was made of pTEX CBHII CBD and from this the NotI fragment containing the CBHII core domain under the control of the cbh1 transcriptional elements and pyr4 gene was isolated by preparative gel electrophoresis. The isolated fragment was transformed into the uridine auxotroph version of the quad deleted strain, 1A52 pyr13, and stable transformants were identified.

To select which transformants expressed cbh2 cellulose binding domain, genomic DNA was isolated from all stably transformant strains following growth on Vogels+1% glucose and Southern blot experiments performed using an isolated DNA fragment containing the cbh1 gene to identify the transformants containing the CBHII CBD PTEX expression vector. Total MRNA was isolated from the transformed strains following growth for 1 day on Vogels+1% lactose. The MRNA was subjected to Northern analysis using the cbh2 coding region as a probe. Most of the transformants expressed cbh2 CBD MRNA at high levels. One transformant was selected and grown under conditions previously described in a 14 L fermentor. The resultant broth was concentrated and the proteins contained therein were separated by SDS polyacrylamide gel electrophoresis and the CBHII CBD protein subjected to Western analysis. A protein of the expected size was identified by reactivity to CBHII CBD polyclonal antibodies raised against the synthetic CBHII CBD peptide having the sequence;

NH2 C-G-G-Q-N-V-S-G-P-T-C-C-A-S-G-S-T-C-COOH (Seq ID No: 48B)

Example 7

Purification of Cellulose Binding Domains

The binding domain can ben purified by methods similar to those reported in the literature (Ong, E., et al 1989 Bio/Technology 7: 604–607). In the case of affinity chromatography, the filtered binding domain broth can be contacted with a cellulosic substance, such as avicel or pulp/paper. The cellulosic solids may be separated by centrifugation or filtration. Alternatively, the filtered broth may be passed over a cellulosic-type column. The bound binding domains may then be eluted by treatment with distilled water, guanidinium HCl/other denaturants, surfactants, or other appropriate elution chemicals. Use of temperature modification may also be an option. Affinity chromatography using antibodies generated against the CBD or CBD derivative may also be employed. A particular purification procedure may require several fractionation steps depending upon the sample matrix and upon the chemical properties of the binding domains and modified domains of the present invention. In some cases the modified domains may contain additional charged functional groups which may allow for the use of other methods such as ionic exchange.

While the invention has been described in terms of various preferred embodiments, the skilled artisan will appreciate that various modifications, substitutions, omissions, and changes may be made without departing from the scope and spirit thereof. Accordingly, it is intended that the scope of the present invention be limited solely by the scope of the following claims, including equivalents thereof.

---

We claim:

1. A truncated fungal cellulase protein derived from Trichoderma comprising an endoglucanase I ("EGI") catalytic core protein or derivative thereof which exhibit endoglucanase activity, wherein said protein lacks cellulose binding activity from an EGI binding domain, said cellulase being produced by a method comprising the steps of:

(a) transforming into a suitable host cell a DNA construct which encodes said EGI catalytic core which is functionally attached to regulatory sequences which permit the transcription and translation of said DNA;

(b) growing said host cell under conditions suitable to express said EGI catalytic core.

2. A truncated fungal cellulase protein according to claim 1 wherein said Trichoderma is *Trichoderma longibrachiatum*.

3. The truncated fungal cellulase of claim 1 wherein said EGI catalytic core consists of the amino acid sequence set forth in SEQ ID NO:14.

* * * * *